(12) United States Patent
Yan et al.

(10) Patent No.: US 7,888,291 B2
(45) Date of Patent: *Feb. 15, 2011

(54) SUBSTRATES AND ASSAYS FOR β-SECRETASE

(75) Inventors: Riqiang Yan, Pepper Pike, OH (US); Alfredo G. Tomasselli, Wildwood, MO (US); Mark E. Gurney, Grand Rapids, MI (US); Thomas L. Emmons, Wentzville, MO (US); Michael Jerome Bienkowski, Ballwin, MO (US); Robert L. Heinrikson, Plainwell, MI (US)

(73) Assignee: Elan Pharmaceuticals, Inc., South San Francisco, CA (US)

( * ) Notice: Subject to any disclaimer, the term of this patent is extended or adjusted under 35 U.S.C. 154(b) by 287 days.

This patent is subject to a terminal disclaimer.

(21) Appl. No.: 10/801,509

(22) Filed: Mar. 16, 2004

(65) Prior Publication Data

US 2004/0254341 A1    Dec. 16, 2004

Related U.S. Application Data

(62) Division of application No. 09/908,943, filed on Jul. 19, 2001.

(60) Provisional application No. 60/219,795, filed on Jul. 19, 2000, provisional application No. 60/275,251, filed on Mar. 12, 2001.

(51) Int. Cl.
*C40B 40/00* (2006.01)

(52) U.S. Cl. .............................. 506/7; 506/13; 506/23

(58) Field of Classification Search ........................ None
See application file for complete search history.

(56) References Cited

FOREIGN PATENT DOCUMENTS

| EP | 0 855 444 | 7/1998 |
|---|---|---|
| WO | WO 92/07068 | 4/1992 |
| WO | WO 00/17369 | 3/2000 |
| WO | WO 00/47618 | 8/2000 |
| WO | WO 00/58479 | 10/2000 |
| WO | WO 02/094985 | 11/2002 |

OTHER PUBLICATIONS

Gruninger-Leitch et al., J. Biol. Chem. 277(7):4687-4693 (2002).*
Majer et al., Protein Science 6:1458-1466 (1997).*
Sauder et al., J. Mol. Biol. 300:241-248 (2000).*
Shi et al. ("Shi"), J. Alzheimer's Disease 7:139-148 (2005).*
Tomasselli et al., J. Neurochemistry 84:1006-1017 (2003).*
Haass et al., "Processing of β-Amyloid Precursor Protein in Microglia and Astrocytes Favors an Internal Localization over Constitutive Secretion"; *The Journal of Neuroscience*, 11(12):3783-3793.
Kang et al., "The precursor of Alzheimer's disease amyloid A4 protein resembles a cell-surface receptor", *Nature*, 325:733-736 (1987).
Kitaguchi et al., "Novel precursor of Alzheimer's disease amyloid protein shows protease inhibitory activity", *Nature*, 331:530-532 (1988).
Lin et al., "Inhibition of Cathepsin D by Synthetic Oligonucleotides", *The Journal of Biological Chemistry*, 254:11875-11883 (1979).
Lin et al., "Human aspartic protease memapsin 2 cleaves the β-secretase site of β-amyloid precursor protein", *PNAS*, 97:1456-1460 (2000).
Ponte et al., "A new A4 amyloid mRNA contains a domain homologous to serine proteinase inhibitors", *Nature*, 331:525-527 (1988).
Schechter et al., "On the Active Site of Proteases, III. Mapping the Active Site of Papain; Specific Peptide Inhibitors of Papain", *Biochemical and Biophysical Research Communications*, 32:898-902 (1968).
Schechter et al., "On the Size of the Active Site in Proteases, I. Papain", *Biochemical and Biophysical Research Communications*, 27:157-162 (1967).
Sinha et al., "Cellular mechanisms of β-amyloid production and secretion", *Proc. Nat'l. Acad. Sci.* (*USA*), 96:11049-11053 (1999).
Tanzi et al., "Protease inhibitor domain encoded by an amyloid protein precursor mRNA associated with Alzheimer's disease", *Nature*, 331:528-530 (1988).
Vassar et al., "β-Secretase Cleavage of Alzheimer's Amyloid Precursor Protein by the Transmembrane Aspartic Protease BACE", *Science*, 286:735-741 (1999(.
Yan et al., "Membrane-anchored aspartyl protease with Alzheimer's disease β-secretase activity.", *Nature*, 402:533-537 (1999).
Younkin, "Processing of the Alzheimer's Disease β A4 Amyloid Protein Precursor (APP)", *Brain Pathology*, 1:253-262 (1991).
Bailey et al., Pro. Science, 3:2129-2143 (1994).
International Search Report; PCT/US00/17661; mailed Apr. 24, 2002.
Majer et al., Pro. Science, 6:1458-1466 (1997).
Martson et al., *Methods in Enzymology*, 182:264-276 (1990).
Oefner et al., *Chem. and Biol.*, 6(3):127-131 (1999).
Sinha et al., *Nature*, 402:537-540(1999).
Yang et al., *Acta Cryst.*, D55:625-630 (1999).

* cited by examiner

*Primary Examiner*—Jeffrey S. Lundgren
(74) *Attorney, Agent, or Firm*—Marshall, Gerstein & Borun LLP

(57) ABSTRACT

The present invention is directed to novel substrates for Hu-Asp. More particularly, the invention provides peptide substrates and fusion polypeptide substrates comprising a β-secretase cleavage site. Methods and compositions for making and using the peptides are disclosed.

24 Claims, 6 Drawing Sheets

FIG. 1A

```
ATGCTGCTGCTGCTGCTGCTGGCCTGGGCCTGAGGCTACAGCTCTCCCTGGCATCATCCA
 M  L  L  L  L  L  L  G  L  R  L  Q  L  S  L  G  I  I  P
GTTGAGGAGGAGAACCCGGACTTCTGGAACCGCGAGGCAGCCGAGGCCCTGGGTGCCGCC
 V  E  E  E  N  P  D  F  W  N  R  E  A  A  E  A  L  G  A  A
AAGAAGCTGCAGCCTGCACAGACAGCCGCCAAGAACCTCATCATCTTCCTGGGCGATGGG
 K  K  L  Q  P  A  Q  T  A  A  K  N  L  I  I  F  L  G  D  G
ATGGGGGTGTCTACGGTGACAGCTGCCAGGATCCTAAAGGGCAGAAGGACAAACTG
 M  G  V  S  T  V  T  A  A  R  I  L  K  G  Q  K  K  D  K  L
GGGCCTGAGATACCCCTGGCCATGGACCGCTTCCCATATGTGGCTCTGTCCAAGACATAC
 G  P  E  I  P  L  A  M  D  R  F  P  Y  V  A  L  S  K  T  Y
AATGTAGACAAACATGTGCCAGACAGTGGAGCCACAGCCACGGCCTACCTGTGCGGGGTC
 N  V  D  K  H  V  P  D  S  G  A  T  A  Y  L  C  G  V
AAGGGCAACTTCCAGACCATTGGCTTGAGTGCAGCCGCGCTTTAACCAGTGCAACACG
 K  G  N  F  Q  T  I  G  L  S  A  A  A  R  F  N  Q  C  N  T
ACACGCGGCAACGAGGTCATCTCCGTGATGAATCGGGCCAAGAAAGCAGGAAGTCAGTG
 T  R  G  N  E  V  I  S  V  M  N  R  A  K  K  A  G  K  S  V
```

FIG. 1B

```
GGAGTGGTAACCACCACGAGTGCAGCACGCCCTCGCCAGCCGGCACTTACGCCCACACG
 G  V  V  T  T  T  R  V  Q  H  A  S  P  A  G  T  Y  A  H  T

GTGAACCGCAACTGGTACTCGGACGCCGACGTGCCTGCCTCGGCCCGCCAGGAGGGGTGC
 V  N  R  N  W  Y  S  D  A  D  V  P  A  S  A  R  Q  E  G  C

CAGGACATCGCTACGCAGCTCATCTCCAACATGGACATTGACGTGATCCTAGGTGGAGGC
 Q  D  I  A  T  Q  L  I  S  N  M  D  I  D  V  I  L  G  G  G

CGAAAGTACATGTTTCCCATGGGAACCCCAGAGTACCCAGATGACTACAGCCAA
 R  K  Y  M  F  P  M  G  T  P  D  D  P  E  Y  P  D  D  Y  S  Q

GGTGGGACCAGGCTGGACGGGAAGAATCTGGTGCAGGAATGGCTGGCGAAGCGCCAGGGT
 G  G  T  R  L  D  G  K  N  L  V  Q  E  W  L  A  K  R  Q  G

GCCCGGTATGTGTGGAACCGCACTGAGCTCATGCAGGCTTCCCTGGACCCGTCTGTGACC
 A  R  Y  V  W  N  R  T  E  L  M  Q  A  S  L  D  P  S  V  T

CATCTCATGGGTCTCTTTGAGCCTGGAGACATGAAATACGAGATCCACCGAGACTCCACA
 H  L  M  G  L  F  E  P  G  D  M  K  Y  E  I  H  R  D  S  T
```

FIG. 1C

```
CTGGACCCCCTCCCTGATGGAGATGACAGAGGCTGCCCTGCGCCTGCTGAGCAGGAACCCC
 L  D  P  S  L  M  E  M  T  E  A  A  L  R  L  L  S  R  N  P

CGCGGGCTTCTCCTCTTCGTGGAGGGTGTCGCATCGACCATGGTCATCATGAAAGCAGG
 R  G  F  F  L  F  V  E  G  G  R  I  D  H  G  H  H  E  S  R

GCTTACCGGGCACTGACTGAGACGATCATGTTCGACGACGCCATTGAGAGGGCGGGCCAG
 A  Y  R  A  L  T  E  T  I  M  F  D  D  A  I  E  R  A  G  Q

CTCACCAGCGAGGAGGACACGCTGAGCCTGGTCACTGCCGACCACTCCCACGTCTTCTCC
 L  T  S  E  E  D  T  L  S  L  V  T  A  D  H  S  H  V  F  S

TTCGGAGGCTACCCCCTGCGAGGGAGCTCCATCTTCGGGCTGGCCCCTGGCAAGGCCCGG
 F  G  G  Y  P  L  R  G  S  S  I  F  G  L  A  P  G  K  A  R

GACAGGAAGGCCTACACGGTCCTCCTCTATACGGAAAACGGTCCAGGCTATGTGCTCAAGGAC
 D  R  K  A  Y  T  V  L  L  Y  G  N  G  P  G  Y  V  L  K  D

GGCGCCCGGCCGGATGTTACCGAGAGCGGGAGCCCCGAGTATCGGCAGCAGTCA
 G  A  R  P  D  V  T  E  S  E  S  G  S  P  E  Y  R  Q  Q  S
```

FIG. 1D

```
GCAGTGCCCCTGGACGAAGAGACCCACGCAGGCGAGGACGTGGCGGTGTTCGCGCGGC
 A  V  P  L  D  E  E  T  H  A  G  E  D  V  A  V  F  A  R  G

CCGCAGGCGCACCTGGTTCACGGCGTGCAGGAGCAGACCTTCATAGCGCACGTCATGGCC
 P  Q  A  H  L  V  H  G  V  Q  E  Q  T  F  I  A  H  V  M  A

TTCGCCGCCTGCCTGGAGCCCTACACCGCCTGCGACCTGGCGCCCCCGGCCACCACC
 F  A  A  C  L  E  P  Y  T  A  C  D  L  A  P  P  A  G  T  T

GACGCCGCGCACCCAGGTAACTATGAAGTTGAATTCCGAAGAGCACTCTACGTAGAGGGT
 D  A  A  H  P  G  N  Y  E  V  E  P  R  R  A  L  Y  V  E  G

GAAAGAGGATTCTTCTACACTCCAAAGGCACTCTACCTCGTAGAGGGTGAAAGAGGATTC
 E  R  G  F  F  Y  T  P  K  A  L  Y  L  V  E  G  E  R  G  F

TTCTACACTAGTCTCATGACCATAGCCTATGTCATGGCTGCCATCTGCGCCCTCTTCATG
 F  Y  T  S  L  M  T  I  A  Y  V  M  A  A  I  C  A  L  F  M

CTGCCACTCTGCCTCATGGTGGACTACAAGGATGATGATGACAAGTAG
 L  P  L  C  L  M  V  D  Y  K  D  D  D  D  K  *
```

SUBSTRATES AND ASSAYS FOR β-SECRETASE

The present application is a divisional application of U. S. Patent Application No. 09/908,943, which claims priority benefit of U. S. Provisional Application No. 60/219,795, filed Jul. 19, 2000, and to U. S. Provisional Application No. 60/275,251 filed Mar. 12, 2001. Each of these applications is specifically incorporated herein by reference in its entirety.

FIELD OF THE INVENTION

The present invention relates to methods and compositions for identification of modulators of β-secretase activity. More particularly, the present invention provides novel substrates for monitoring the β-secretase activity of human Asp2 protease and methods of using the same. Such methods and compositions will be useful in the identification of agents that modulate β-secretase activity and thus may be used in the therapeutic intervention of disorders characterized by the presence of amyloid plaques.

BACKGROUND OF THE INVENTION

Alzheimer's disease (AD) causes progressive dementia with consequent formation of amyloid plaques, neurofibrillary tangles, gliosis and neuronal loss. The disease occurs in both genetic and sporadic forms whose clinical course and pathological features are quite similar. Three genes have been discovered to date which, when mutated, cause an autosomal-dominant form of Alzheimer's disease. These encode the amyloid protein precursor (APP) and two proteins, presenilin-1 (PS1) and presenilin-2 (PS2), which are structurally and functionally related. Mutations in any of the three proteins have been observed to enhance proteolytic processing of APP via an intracellular pathway that produces amyloid beta peptide (Aβ peptide, sometimes referred to as Abeta), a 40-42 amino acid peptide that is the primary component of amyloid plaque in AD (Younkin, *Brain Pathol.* 1(4):253-62, 1991; Haass, *J. Neurosci.* 11(12):3783-93, 1991).

Dysregulation of intracellular pathways for proteolytic processing may be central to the pathophysiology of AD. In the case of plaque formation, mutations in APP, PS1 or PS2 consistently alter the proteolytic processing of APP so as to enhance formation of Aβ 1-42, a form of the Aβ peptide which seems to be particularly amyloidogenic, and thus very important in AD. APP localizes to the secretory membrane structure including the cell surface, and has a single C-terminal transmembrane domain. Examples of specific isotypes of APP which are currently known to exist in humans include the 695-amino acid polypeptide described by Kang et. al. (1987), *Nature* 325: 733-736 which is designated as the "normal" APP; the 751 amino acid polypeptide described by Ponte et al. (1988), *Nature* 331: 525-527 (1988) and Tanzi et al. (1988), *Nature* 331: 528-530; and the 770 amino acid polypeptide described by Kitaguchi et. al., *Nature* 331: 530-532 (1988).

The Aβ peptide is derived from a region of APP adjacent to and containing a portion of the transmembrane domain. Normally, processing of APP at the α-secretase site cleaves the midregion of the Aβ sequence adjacent to the membrane and releases the soluble, extracellular domain of APP from the cell surface. This α-secretase APP processing creates soluble APP-α, which is not thought to contribute to AD. However, pathological processing of APP at the β- and γ-secretase sites, which are located N-terminal and C-terminal to the α-secretase site, releases the Aβ peptide. Processing at the β- and γ-secretase sites can occur in both the endoplasmic reticulum (in neurons) and in the endosomal/lysosomal pathway after re-internalization of cell surface APP (in all cells). The β-secretase cleavage site is located 28 residues from the plasma membrane luminal surface and the γ-secretase cleavage site is located in the transmembrane region. The in vivo processing of the β-secretase site is thought to be the rate limiting step in Aβ production (Sinha and Lieberburg, *Proc. Nat'l. Acad. Sci., USA* 96(4), 11049-11053, 1999) and as such is a favored target therapeutic target.

Recently, several groups of investigators have reported that a human aspartyl protease (Hu-Asp2) has an activity responsible for the processing of APP at the β-secretase cleavage site. Hu-Asp2 is a membrane-bound aspartyl protease (Yan et al., *Nature* 402:533-536, 1999; Lin et al., *Proc. Nat'l Acad. Sci., USA* 97(4): 1456-1460, 2000; Vassar et al., *Science*, 286:735-741, 1999). Aspartyl proteases such cathepsin D, Pepsin, renin, and viral aspartyl proteases comprise signature catalytic triplets . . . Asp-Thr-Gly . . . and . . . Asp-Ser-Gly . . . . In Hu-Asp2, these signature catalytic triplets are harbored opposite to each other in the bilobed structure of Hu-Asp2. An important feature of Hu-Asp2 that is absent from other known mammalian aspartyl proteases is a stretch of 27 amino acids located near the C-terminus that anchors Hu-Asp2 to the membrane and is essential for the enzyme function in cells.

To date, in vitro assays with recombinant Hu-Asp2 or Hu-Asp2 purified from brain have relied on peptide substrates comprising the β-secretase recognition sequence of the β-amyloid precursor sequence (i.e., APP sequence), such as the APP Swedish mutation sequence . . . EVNL-DAEFR . . . (SEQ ID NO:113) in which the hyphen denotes the point at which the peptide is cleaved by the β-secretase. The same approach has been used for β-secretase assays in cell lines expressing Hu-Asp2.

There presently exists a need to identify compounds that may act as surrogates for the APP substrate of Hu-Asp2. Identifying such substrates facilitates new in vitro and model in vivo assays for identifying therapeutic agents that affect APP processing at the β-secretase site. Ultimately, the identification of such substrates and assays will lead to advances in the identification of therapeutic compounds for the beneficial intervention of Alzheimer's Disease.

SUMMARY OF THE INVENTION

The present invention provides novel substrates, assays and methods for conducting aspartyl protease assays. More particularly, one aspect of the present invention provides an isolated peptide comprising a sequence of at least four amino acids defined by formula $P_2P_1$--$P_1'P_2'$ wherein $P_2$ is a charged amino acid, a polar amino acid, or an aliphatic amino acid but is not an aromatic amino acid; $P_1$ is an aromatic amino acid or an aliphatic amino acid but not a polar amino acid or a charged amino acid; $P_1'$ is a charged amino acid, or aliphatic amino acid, or a polar amino acid but is not an aromatic amino acid; and $P_2'$ is an uncharged aliphatic polar amino acid or an aromatic amino acid but not a charged amino acid; wherein the peptide is cleaved between $P_1$ and $P_1'$ by a human aspartyl protease encoded by the nucleic acid sequence of SEQ ID NO:1 or SEQ ID NO:3 and the peptide does not comprise the corresponding $P_2P_1$-$P_1'P_2'$ portion of amino acid sequences depicted in SEQ ID NO:19; SEQ ID NO:20; SEQ ID NO:21; SEQ ID NO:26; SEQ ID NO:27; SEQ ID NO:28; SEQ ID NO:31; SEQ ID NO:32; SEQ ID NO:33; SEQ ID NO:34; SEQ ID NO:35; SEQ ID NO:36; SEQ ID NO:37; SEQ ID NO:38; SEQ ID NO:39; or SEQ ID NO:40.

In certain embodiments, the isolated peptide comprises an amino acid sequence defined by formula $P_2P_1$--$P_1'P_2'P_3'$, wherein $P_3'$ is any amino acid, and wherein said peptide does not comprise the corresponding $P_2P_1$--$P_1'P_2'P_3'$ portion of amino acid sequences depicted in SEQ ID NO:19; SEQ ID NO:20; SEQ ID NO:21; SEQ ID NO:26; SEQ ID NO:27; SEQ ID NO:28; SEQ ID NO:31; SEQ ID NO:32; SEQ ID NO:33; SEQ ID NO:34; SEQ ID NO:35; SEQ ID NO:36; SEQ ID NO:37; SEQ ID NO:38; SEQ ID NO:39; or SEQ ID NO:40.

In more specific embodiments, the isolated peptide comprises an amino acid sequence defined by formula $P_3P_2P_1$--$P_1'P_2'P_3'$, wherein $P_3$ is an uncharged polar amino acid, an uncharged aliphatic amino acid, or an aromatic amino acid, and wherein the the peptide does not comprise the corresponding $P_3P_2P_1$--$P_1'P_2'P_3'$ portion of amino acid sequences depicted in SEQ ID NO:19; SEQ ID NO:20; SEQ ID NO:21; SEQ ID NO:26; SEQ ID NO:27; SEQ ID NO:28; SEQ ID NO:31; SEQ ID NO:32; SEQ ID NO:33; SEQ ID NO:34; SEQ ID NO:35; SEQ ID NO:36; SEQ ID NO:37; SEQ ID NO:38; SEQ ID NO:39; or SEQ ID NO:40. In other embodiments, the isolated peptide comprises an amino acid sequence defined by formula $P_4P_3P_2P_1$--$P_1'P_2'P_3'$ wherein the $P_4$ is a charged amino acid, a polar amino acid or an aliphatic amino acid but not an aromatic amino acid and the peptide does not comprise the corresponding $P_4P_3P_2P_1$--$P_1'P_2'P_3'$ portion of amino acid sequences depicted in SEQ ID NO:19; SEQ ID NO:20; SEQ ID NO:21; SEQ ID NO:26; SEQ ID NO:27; SEQ ID NO:28; SEQ ID NO:31; SEQ ID NO:32; SEQ ID NO:33; SEQ ID NO:34; SEQ ID NO:35; SEQ ID NO:36; SEQ ID NO:37; SEQ ID NO:38; SEQ ID NO:39; or SEQ ID NO:40. In other particular embodiments, the peptide further comprises an amino acid at position $P_4'$ immediately to the carboxy-terminal position of $P_3'$, wherein the $P_4'$ is any amino acid and wherein the peptide does not comprise the corresponding $P_3P_2P_1$--$P_1'P_2'P_3'P_4'$ portion of amino acid sequences depicted in SEQ ID NO:19; SEQ ID NO:20; SEQ ID NO:21; SEQ ID NO:26; SEQ ID NO:27; SEQ ID NO:28; SEQ ID NO:31; SEQ ID NO:32; SEQ ID NO:33; SEQ ID NO:34; SEQ ID NO:35; SEQ ID NO:36; SEQ ID NO:37; SEQ ID NO:38; SEQ ID NO:39; or SEQ ID NO:40.

In particularly preferred embodiments, $P_2$ is an amino acid selected from the group consisting of N, L, K, S, G, T, D, A, Q and E.

In preferred embodiments, $P_1$ is an amino acid selected from the group consisting of Y, L, M, Nle, F, and H.

In preferred embodiments, define $P_1'$ as an amino acid selected from the group consisting of E, A, D, M, Q, S and G.

In preferred embodiments, $P_2'$ is an amino acid selected from the group consisting of V, A, N, T, L, F, and S.

In preferred embodiments, $P_3'$ is an amino acid selected from the group consisting of E, G, F, H, cysteic acid and S.

In preferred embodiments, $P_3$ is an amino acid selected from the group consisting of A, V, I, S, H, Y, T and F.

In preferred embodiments, $P_4$ is an amino acid selected from the group consisting of E, G, I, D, T, cysteic acid and S.

In preferred embodiments $P_4'$ is an amino acid selected from the group consisting of F, W, G, A, H, P, G, N, S, and E. Many highly preferred residues will be apparent from the detailed description.

In preferred embodiments of the invention, the isolated peptide further comprises a first label. In specific embodiments, the peptide comprises a cysteic acid comprising a covalently attached label. Other preferred embodiments contemplate that the peptide further comprises a second label. In this aspect of the invention, it is contemplated that the label may be any label commonly employed for the detection and/ or quantification of a peptide. In specific embodiments, the peptide of the instant invention may comprise a detectable label and a quenching moiety that quenches a detectable property of the label when the label and quenching moiety are in close proximity. More specifically, the quenching moiety and label are selected such that cleavage of the peptide between $P_1$ and $P_1'$ will separate the quenching moiety to permit detection of the label. Thus, in a preferred embodiment, the quenching moiety and label are attached to the peptides on opposite sides of the $P_1$-$P_1'$ cleavage site.

In preferred embodiments of the present invention, the invention provides a genus of peptides that are cleaved by the human aspartyl protease Hu-Asp2 at a rate greater than the rate of cleavage of a polypeptide comprising the human APP β-secretase cleavage sequence: SEVKM-DAEFR (SEQ ID NO:20). Still more preferred embodiments provide a genus of peptides cleaved by the human aspartyl protease at a rate greater than the rate of cleavage of a polypeptide comprising the human APP Swedish KM→NL mutation, β-secretase cleavage sequence SEVNL-DAEFR (SEQ ID NO:19).

Particularly preferred peptides of the present invention include but are not limited to those comprising any one of the sequences set forth in SEQ ID NO:5; SEQ ID NO:6; SEQ ID NO:7; SEQ ID NO:8; SEQ ID NO:9; SEQ ID NO:10; SEQ ID NO:11; SEQ ID NO:12; SEQ ID NO:13; SEQ ID NO:14; SEQ ID NO:15; SEQ ID NO:16; SEQ ID NO:17, SEQ ID NO:18; SEQ ID NO:120; SEQ ID NO:133; SEQ ID NO:134; SEQ ID NO:135; SEQ ID NO:136; SEQ ID NO:137; SEQ ID NO:138; SEQ ID NO:141; SEQ ID NO:143; SEQ ID NO:144; SEQ ID NO:145; SEQ ID NO:147; SEQ ID NO:148; SEQ ID NO:149; SEQ ID NO:150; SEQ ID NO:151; SEQ ID NO:152; SEQ ID NO:153; SEQ ID NO:154; SEQ ID NO:155; SEQ ID NO:156; SEQ ID NO:157; SEQ ID NO:158; SEQ ID NO:159; SEQ ID NO:160; SEQ ID NO:161; SEQ ID NO:162; SEQ ID NO:163; SEQ ID NO:164; SEQ ID NO:165; SEQ ID NO:166; SEQ ID NO:167; SEQ ID NO:168; SEQ ID NO:169; SEQ ID NO:190; SEQ ID NO:191; SEQ ID NO:192 and SEQ ID NO:193.

An additional aspect of the present invention relates to fusion polypeptides comprising the amino acid sequence of a novel β-secretase cleavage site described by one of the peptides of the instant invention and an additional amino acid sequence. More particularly, the invention contemplates a polypeptide comprising a peptide of the instant invention and further comprising a transmembrane domain amino acid sequence. In specific embodiments, the peptide containing the β-secretase cleavage site is N-terminal to the transmembrane domain, but C-terminal also is contemplated. In certain embodiments, the peptide and the transmembrane domain may be separated by a linker. More specifically, the linker may be a peptide linker comprising about 20 to about 40 amino acids. In particularly preferred embodiments, the transmembrane domain anchors the polypeptide to an intracellular membrane selected from the group consisting of the Golgi or the endoplasmic reticulum. As such, the transmembrane domain comprises the transmembrane domain amino acid sequence of a protein that is anchored to the Golgi or ER membrane of cells that express such a protein. In preferred embodiments, the fusion polypeptide comprises a transmembrane domain selected from the group consisting of the transmembrane domain of galactosyltransferase, the transmembrane domain of sialyly transferase; the transmembrane domain of human aspartyl transferase 1; the transmembrane domain of human aspartyl transferase 2; the transmembrane domain of syntaxin 6; the transmembrane domain of acetyl glucosaminyl transferase; and the transmembrane domain of APP.

In preferred embodiments of the invention the fusion protein may further comprise a reporter protein amino acid sequence in addition to the peptide sequence and the transmembrane sequence. The reporter sequence preferably provides a detectable and quantifiable characteristic (e.g. an optical characteristic) or is an enzyme that catalyzes a substrate into a product, wherein the substrate or product provides a detectable and quantifiable characteristic. Also contemplated are, fusion polypeptides comprising a reporter protein amino acid sequence and a β-secretase cleavage site containing peptide sequence of the present invention. In preferred aspects of the invention, the reporter protein is selected from the group consisting of luciferase; alkaline phosphatase; β-galactosidase; β-glucorimidase; green fluorescent protein; and chloramphenical acetyl transferase.

In certain aspects, the present invention contemplates a mutant or derivative APP molecule in which the natural β-secretase cleavage site of wild-type APP has been modified to contain a b-secretase cleavage site of one of the substrates of the present invention. Such a mutant or derivative APP may be generated by site directed mutagenesis or by peptide synthesis as described herein.

Additional aspects of the invention contemplate a polynucleotide comprising a nucleotide sequences that encodes a fusion polypeptide of the present invention. Other embodiments contemplate a polynucleotide comprising a nucleotide sequence that encodes a peptide substrate of the present invention. Also contemplated herein is a vector comprising any of the polynucleotides of the present invention. In preferred embodiments, the vector comprises a polynucleotide encoding a peptide or a fusion polypeptide of the present invention, wherein the polynucleotide is operably linked to a promoter to promote expression of the fusion protein encoded by the polynucleotide in a host cell. Other embodiments contemplate a host cell transformed or transfected with a polynucleotide or vector described by the present invention. In a preferred embodiment, the host cell is co-transfected with the polynucleotide/vector and a polynucleotide/vector encoding Hu-Asp2.

Also described herein is a method of producing a substrate for a β-secretase assay comprising growing a host cell transformed or transfected with a vector of the present invention in a manner that permits the expression of the polypeptide. Additional embodiments of this aspect of the invention may further comprise purifying the polypeptide. In preferred embodiments, the host cell is selected from the group consisting of a mammalian host cell, a bacterial host cell and a yeast host cell.

Also contemplated herein are transgenic animals comprising an APP mutant having as β-secretase cleavage one of the peptides of the present invention.

In a further aspect, the present invention provides a method for assaying for modulators of β-secretase activity, comprising the steps of contacting a first composition with a second composition both in the presence and in the absence of a putative modulator compound, wherein the first composition comprises a mammalian β-secretase polypeptide or biologically active fragment thereof, and wherein the second composition comprises a substrate, wherein the substrate comprises a peptide or a fusion polypeptide of the present invention. In preferred embodiments, the method further comprises measuring cleavage of the substrate peptide in the presence and in the absence of the putative modulator compound; and identifying modulators of β-secretase activity from a difference in cleavage in the presence versus in the absence of the putative modulator compound, wherein a modulator that is a β-secretase antagonist reduces such cleavage and a modulator that is a β-secretase agonist increases such cleavage. In specific embodiments, the first composition may comprise a purified human Asp2 polypeptide. In other embodiments, the first composition may comprise a soluble fragment of a human Asp2 polypeptide that retains Asp2 β-secretase activity. More particularly, the soluble fragment may be a fragment lacking an Asp2 transmembrane domain. In preferred embodiments, the β-secretase polypeptide of the first composition comprises a polypeptide purified and isolated from a cell transformed or transfected with a polynucleotide comprising a nucleotide sequence that encodes the β-secretase polypeptide.

In other specific embodiments, the first composition comprises in a cell transformed or transfected with a polynucleotide comprising a nucleotide sequence that encodes the β-secretase polypeptide, and the measuring step comprises measuring APP processing activity of the cell.

Further aspects of the invention contemplate treating Alzheimer's Disease with an agent identified as an inhibitor of Hu-Asp2 according to the methods of the present invention. Preferred aspects further contemplate a β-secretase modulator identified according to the methods of the present invention. Specifically contemplated are methods of inhibiting β-secretase activity in vivo comprising a step of administering a modulator identified by the present invention, wherein the modulator is a β-secretase antagonist, to a mammal in an amount effective to inhibit β-secretase in cells of the mammal.

Also described herein is a pharmaceutical composition comprising a β-secretase modulator identified by the present invention and a pharmaceutically acceptable carrier. Further aspects of the invention describe a method of treating a disease or condition characterized by an abnormal β-secretase activity comprising administering to a subject in need of treatment a pharmaceutical composition as described above. Other embodiments describe the use of a modulator identified according to the present invention in the manufacture of a medicament for the treatment of Alzheimer's Disease.

In a related aspect, the invention provides a container containing a composition comprising a modulator identified according to the present invention, the container containing a label describing the indication of the modulator for treating Alzheimer's Disease. Preferably, the composition further comprises a pharmaceutical carrier. Most preferably, the composition is a unit dose formulation.

Additional methods are described for identifying agents that inhibit the activity of human Asp2 aspartyl protease (Hu-Asp2), comprising the steps of contacting a peptide or a fusion polypeptide of the invention and a composition comprising an Hu-Asp2 activity in the presence and absence of a test agent; determining the cleavage of the peptide or polypeptide between the $P_1$ and $P_1'$ by the Hu-Asp2 in the presence and absence of the test agent; and comparing the cleavage activity of the Hu-Asp2 in the presence of the test agent to the activity in the absence of the test agent to identify an agent that inhibits the cleavage by the Hu-Asp2, wherein reduced activity in the presence of the test agent identifies an agent that inhibits Hu-Asp2 activity. In preferred embodiments, the Hu-Asp2 is a recombinant Hu-Asp2 purified and isolated from a cell transformed or transfected with a polynucleotide comprising a nucleotide sequence that encodes Hu-Asp2. In other embodiments, the Hu-Asp2 is expressed in a cell, wherein the contacting comprises growing the cell in the presence and absence of the test agent, and the determining step comprises measuring cleavage of the peptide or fusion protein. In specific embodiments, the cell further comprises a polynucleotide encoding the polypeptide, and wherein the contacting step comprises growing the cell under conditions in which the cell expresses the polypeptide. In preferred embodiments, the cell is a human embryonic kidney cell line 293 cell and a mouse Neuro-2a neuroblastoma cell line. In other preferred embodiments, the nucleotide sequence is selected from the group consisting of a nucleotide sequence encoding the Hu-Asp2(a) amino acid sequence set forth in SEQ ID NO: 2; a nucleotide sequence encoding the Hu-Asp2(b) amino acid sequence set forth in SEQ ID NO: 4; a nucleotide sequence encoding a fragment of Hu-Asp2(a) (SEQ ID NO: 2) or Hu-Asp2(b) (SEQ ID NO: 4), wherein the fragment exhibits aspartyl protease activity characteristic of Hu-Asp2(a) or Hu-Asp2(b); and a nucleotide sequence of a polynucleotide that hybridizes under stringent hybridization conditions to a Hu-Asp2-encoding polynucleotide selected from the group consisting of SEQ ID NO: 1 and SEQ ID NO: 3.

An additional aspect describes a method for identifying agents that modulate the activity of Asp2 aspartyl protease, comprising the steps of contacting an Asp2 aspartyl protease and a peptide or fusion polypeptide of the present invention in the presence and absence of a test agent, wherein the Asp2 aspartyl protease is encoded by a nucleic acid molecule that hybridizes under stringent hybridization conditions to a Hu-Asp2-encoding polynucleotide selected from the group consisting of SEQ ID NO: 1 and SEQ ID NO: 3; determining the cleavage of the peptide or fusion protein between the $P_1$ and the $P_1'$ site by the Asp2 in the presence and absence of the test agent; and comparing the cleavage activity of the Asp2 in the presence of the test agent to the cleavage activity in the absence of the agent to identify agents that modulate the activity of the polypeptide, wherein a modulator that is an Asp2 inhibitor reduces the cleavage and a modulator that is an Asp2 agonist increases the cleavage. In preferred embodiments, the method further comprises the step of treating Alzheimer's Disease with an agent identified as an inhibitor of Hu-Asp2 according to the instant invention.

Also described is a method for identifying agents that inhibit the activity of human Asp2 aspartyl protease (Hu-Asp2), comprising the steps of growing a cell in the presence and absence of a test agent, wherein the cell expresses a Hu-Asp2 or mouse Asp2 and expresses a protein comprising a peptide or fusion polypeptide of the present invention; determining the cleavage of the protein at the site between the $P_1$ and $P_1'$ in the cell in the presence and absence of the test agent; and comparing the cleavage activity in the presence of the test agent to the cleavage activity in the absence of the test agent to identify an agent that inhibits the activity of Hu-Asp2, wherein reduced cleavage activity in the presence of the test agent identifies an agent that inhibits Hu-Asp2 activity. In preferred embodiments, the host cell either expresses endogenous Asp2 or has been transformed or transfected with a polynucleotide comprising a nucleotide sequence that encodes a Hu-Asp2, wherein the nucleotide sequence is selected from the group consisting of a nucleotide sequence encoding the Hu-Asp2(a) amino acid sequence set forth in SEQ ID NO: 2; a nucleotide sequence encoding the Hu-Asp2 (b) amino acid sequence set forth in SEQ ID NO: 4; a nucleotide sequence encoding a fragment of Hu-Asp2(a) (SEQ ID NO: 2) or Hu-Asp2(b) (SEQ ID NO: 4), wherein the fragment exhibits aspartyl protease activity characteristic of Hu-Asp2 (a) or Hu-Asp2(b); and a nucleotide sequence of a polynucleotide that hybridizes under stringent hybridization conditions to a Hu-Asp2-encoding polynucleotide selected from the group consisting of SEQ ID NO: 1 and SEQ ID NO: 3. The invention also contemplates the use of an agent identified as an inhibitor of Hu-Asp2 according the present invention in the manufacture of a medicament for the treatment of Alzheimer's Disease.

The preceding paragraphs describe methods for identifying modulators of aspartyl protease activity using peptide substrates of the invention, or using polypeptides comprising the peptides. With respect to each of those methods, a preferred embodiment includes an additional step of synthesizing more of a modulator that-has been identified as an aspartyl protease inhibitor. In a preferred variation, the method further comprises synthesizing a composition comprising the modulator in a pharmaceutically acceptable diluent, adjuvant, or carrier. The methods optionally comprise still a further step of administering the composition to a mammal to inhibit aspartyl protease activity in the mammal.

Additionally, the invention contemplates kits for performing a β-secretase assay comprising a β-secretase substrate peptide of the present invention packaged with a β-secretase enzyme. In specific embodiments, the β-secretase substrate may be a fusion polypeptide of the present invention. Further embodiments contemplate that the kits may comprise reagents for detecting the cleavage of the peptide or fusion protein. The invention also describes other preferred peptides which comprise a sequence of at least 10 amino acids having the sequence SEISY-EVEFR (SEQ ID NO:152). Also contemplated are peptides which comprise 3, 4, 5, 10, 12, 15, 20, 25, 30, 35, 40, 45, 50, 55, 60, 65, 70, 75, 80, 85, 90, 95, or 100 amino acids immediately to the carboxy-terminal of SEISY-EVEFR (SEQ ID NO:152) and/or immediately to the amino-terminal of SEISY-EVEFR (SEQ ID NO:152). Preferred peptides may be 10, 13, 15, 16, 20, 25, 30, 35, 40, 45, 50, 55, 60, 65, 70, 75, 80, 85, 100, 110, 120, 130, 140, 150, 160, 170, 180, 190, 200 amino acids or longer.

Additional features and variations of the invention will be apparent to those skilled in the art from the entirety of this application, including the drawing and detailed description, and all such features are intended as aspects of the invention. Likewise, features of the invention described herein can be re-combined into additional embodiments that also are intended as aspects of the invention, irrespective of whether the combination of features is specifically mentioned above as an aspect or embodiment of the invention. Also, only such limitations which are described herein as critical to the invention should be viewed as such; variations of the invention lacking limitations which have not been described herein as critical are intended as aspects of the invention.

In addition to the foregoing, the invention includes, as an additional aspect, all embodiments of the invention narrower in scope in any way than the variations specifically mentioned above. Although the applicant(s) invented the full scope of the claims appended hereto, the claims appended hereto are not intended to encompass within their scope the prior art work of others. Therefore, in the event that statutory prior art within the scope of a claim is brought to the attention of the applicants by a Patent Office or other entity or individual, the applicant(s) reserve the right to exercise amendment rights under applicable patent laws to redefine the subject matter of such a claim to specifically exclude such statutory prior art or obvious variations of statutory prior art from the scope of such a claim. Variations of the invention defined by such amended claims also are intended as aspects of the invention. The detailed description presented below, while providing preferred embodiments of the invention, is intended to be illustrative only since changes and modification within the scope of the invention will be possible whilst still providing an embodiment that is within the spirit of the invention as a whole.

BRIEF DESCRIPTION OF THE DRAWINGS

The following drawing forms part of the present specification and is included to further demonstrate aspects of the present invention. The invention may be better understood by reference to the drawing in combination with the detailed description of the specific embodiments presented herein.

FIG. 1A through FIG. 1D depicts a contiguous, complete sequence of an exemplified fusion polypeptide (SEQ ID NO:128) of the present invention and the nucleotide sequence encoding the polypeptide (SEQ ID NO:127). The entire coding sequence for secreted alkaline phosphatase from MLLL (SEQ ID NO:44) . . . to DAAHPG (SEQ ID NO:45) is shown in normal font. Sequences derived from insulin β-chain with the modified β-secretase cleavage site are italicized. The transmembrane domain from Asp2 454-477 is underlined. DYKDDDK (SEQ ID NO:114) is a flag tag sequence.

DETAILED DESCRIPTION OF THE PREFERRED EMBODIMENTS

Figure 2:
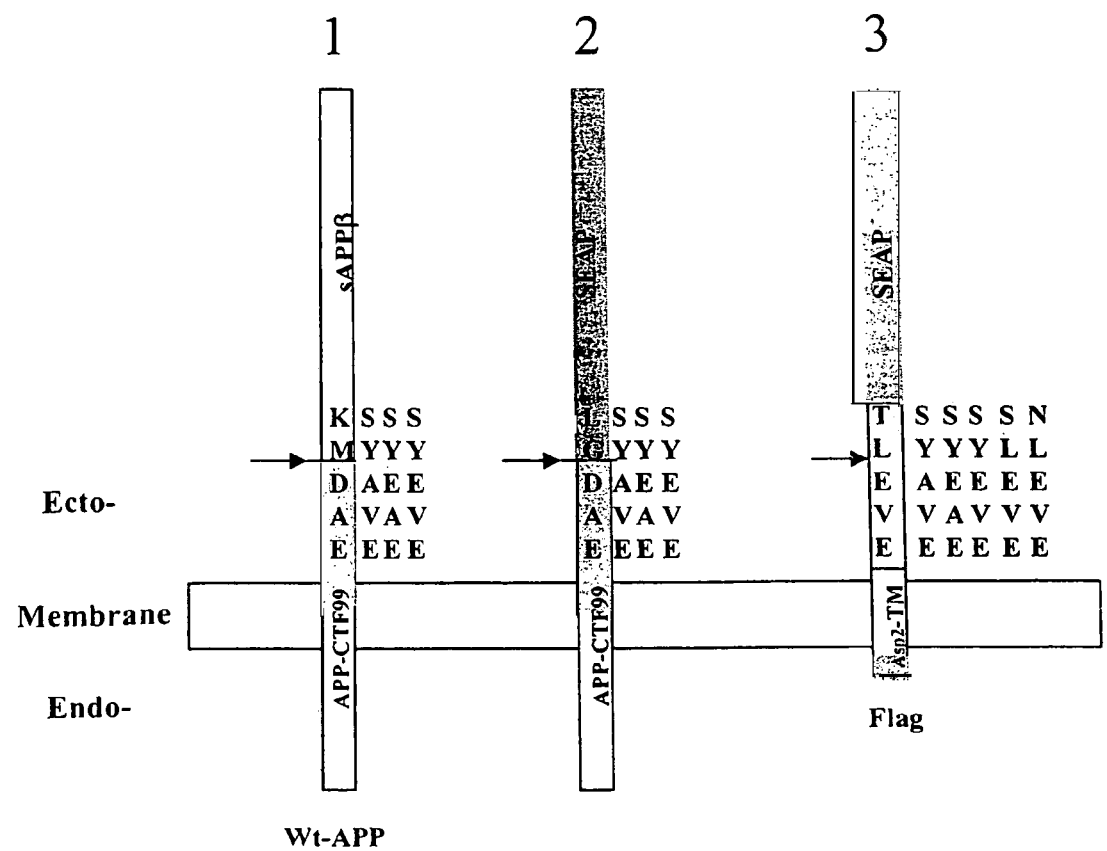
FIG. 2 depicts proposed chimeras as substrates for Asp2 in cell based assays. The portion designated "ecto" refers to ectodomain, the portion designated "endo" refers to endodomain and the portion designated "memb" refers to the membrane domain of the chimeric protein respectively.

Alzheimer's disease is a leading age-related disorder associated with progressive dementia and pathology characterized by cortical atrophy and deposition of senile plaques and neurofibrillary tangles. A primary component of the plaques is the 40-42 amino acid long peptide, Aβ derived from a region of APP adjacent to and containing a portion of the transmembrane domain of the full length APP. This pathogenic peptide is generated as a result of sequential processing due to β- and γ-secretases activities. While there has been extensive hunt for the identity of these enzymes, the exact identity of the protein has remained elusive. Recently, however, significant evidence has accumulated to suggest that Hu-Asp2 may be a likely candidate for the β-secretase activity. There present invention provides compounds, molecules or substrates that may be cleaved by Hu-Asp2 and act as surrogates for the APP substrate. Methods and compositions for making and using these compounds are provided in further detail below.

I. Novel Peptide Substrates for Hu-Asp2

The present invention provides substrates for Hu-Asp2. Initially, a number of peptides were tested as potential substrates of Hu-Asp2. The peptides:

| | |
|---|---|
| AcGSESMDSGISL-DNKW, | (SEQ ID NO: 115) |
| WKKGAIIGL-MVGGVVKK, | (SEQ ID NO: 116) |
| ANL-STFAQPRR, | (SEQ ID NO: 117) |
| YRYQSHDYAF-SSVEKLLHLGGC, | (SEQ ID NO: 118) |
| YRYQSHDY-AFSSVEKLLHLGGC | (SEQ ID NO: 119) | are cleaved between the two amino acids separated by a hyphen.

Also $(His)_6$Ubiquitin and the fusion protein $(His)_6$Ubiquitin-CTAPIII are cleaved at the C-terminal side of a Leu residue in the sequence

...KTITL-EVEPS....        (SEQ ID NO: 120)

However, all these substrates are cleaved less efficiently than the peptide, corresponding to the Swedish mutant form of APP: SEVNL-DAEFR (SEQ ID NO:19). Interestingly, the oxidized insulin B chain is a substrate of Asp2 and is cleaved at a rate comparable to SEVNL-DAEFR (SEQ ID NO:19). The cleavage site for the insulin B chain is between Tyr and Leu in the sequence VEALY-LVC(SO$_3$)GER (SEQ ID NO:121). An additional peptide with a Glu in place of cysteic acid (VEALY-LVEGER (SEQ ID NO:122) also was tested and found to be cleaved by the Hu-Asp2. Using these observations, the inventors conducted further comparisons of the above Hu-Asp2 substrates with additional known Hu-Asp2 substrates to elucidated information regarding specific amino acid occupancy at and around the cleavage site.

Conventional abbreviations for amino acids are used herein, as follows:

Alanine, Ala, A; Arginine, Arg, R; Asparagine, Asn, N; Aspartic acid, Asp, D; Cysteine, Cys, C; Glutamine, Gln, Q; Glutamic Acid, Glu, E; Glycine, Gly, G; Histidine, His, H; Isoleucine, Ile, I; Leucine, Leu, L; Lysine, Lys, K; Methionine, Met, M; Phenylalanine, Phe, F; Proline, Pro, P; Serine, Ser, S; Threonine, Thr, T; Tryptophan, Trp, W; Tyrosine, Tyr, Y; Valine, Val, V; Aspartic acid or Asparagine, Asx, B; Glutamic acid or Glutamine, Glx, Z; Norleucine, Nle; Acetylglycine (Ac)G; Any amino acid, Xaa, X. Additional modified amino acids also may be used as described herein. For example, C(SO$_3$) refers to cysteic acid.

The peptides depicted in Table 1 comprise a hyphen to indicate the estimated cleavage site for Hu-Asp2.

TABLE 1

| Peptide Sequence | Origin/identity | Sequence identifier |
|---|---|---|
| SEVNL-DAEFR | β-secretase, Aβ Swedish Mutant Sequence | SEQ ID NO: 19 |

TABLE 1-continued

| Peptide Sequence | Origin/identity | Sequence identifier |
|---|---|---|
| SEVKM-DAEFR | β-secretase, Aβ Normal Sequence | SEQ ID NO: 20 |
| SEVN(Nle)-DAEFR | β-secretase, Aβ Swedish Mutant L→Nle | SEQ ID NO: 21 |
| (Ac)GSESMDSGISL-DNKW | Casp-3 prosegemnt | SEQ ID NO: 22 |
| WKKGAIIGL-MVGGVVKK | δ-cleavage on Aβ | SEQ ID NO: 23 |
| ANL-STFAQPRR | Novel Sequence | SEQ ID NO: 24 |
| ....EFRHDSGY-EVHHQKLVFFAE.... | cleavage on Ab | SEQ ID NO: 25 |
| ....LTGKTITL-EVEPSDTI..... | (His)$_6$Ubiquitin-CT APIII sequence | SEQ ID NO: 26 |
| FVNQHLC$_{ox}$GSHLVEALY-LVC$_{ox}$GER GFFYTPKA | oxidized Insulin B chain sequence | SEQ ID NO: 27 |
| GIVEQCoxC$_{ox}$ASVC$_{ox}$SLY-QLENYC$_{ox}$N | oxidized Insulin A chain sequence | SEQ ID NO: 28 |
| YRYQSHDY-AFSSVEKLLHALGGC | Novel Sequence of the present invention | SEQ ID NO: 29 |
| YRYQSHDYAF-SSVEKLLHALGGC | | SEQ ID NO: 30 |
| LVNM-AEGD | PS1 | SEQ ID NO: 31 |
| RGSM-AGVL | M2-Pro | SEQ ID NO: 32 |
| GTQH-GIRL | M2-Pro | SEQ ID NO: 33 |
| SSNF-AVGA | M2 | SEQ ID NO: 34 |
| GLAY-AEIA | M2 | SEQ ID NO: 35 |
| HLCG-SHLV | Oxidized Insulin B-chain | SEQ ID NO: 36 |
| CGER-GFFY | Oxidized Insulin B-chain | SEQ ID NO: 37 |
| GVLL-SRK | Notch | SEQ ID NO: 38 |
| VGS-GVLL | Notch | SEQ ID NO: 39 |
| V-GSGV | Notch | SEQ ID NO: 40 |

As used herein throughout, COX and C(SO$_3$) refer to oxidized cysteine otherwise referred to herein as cysteic acid, these terms are used interchangeably herein and in the art. It should be noted that wherever cysteic acid is used at a particular residue in peptide substrates of the present invention, additional substrates that comprise cysteine at that residue also are contemplated. In preferred embodiments, the cysteine in SEQ ID NO:36 and SEQ ID NO:37 is oxidized to cysteic acid.

The peptides of the present invention are described using the nomenclature by Schechter and Berger (*Biochem. Biophys. Res. Commun.* 27:157(1967) and *Biochem. Biophys. Res. Commun.* 32:898 (1968), in which the amino acid residues in the peptide substrate that undergo the cleavage are defined as $P_1 \ldots P_n$ moving from the scissile bond toward the N-terminus and $P_1' \ldots P_n'$ moving from the scissile bond toward the C-terminus. Therefore, the scissile bond is between the $P_1$ and the $P_1'$ residue of the peptide subunits and is denoted herein throughout with a hyphen between the $P_1$ and the $P_1'$.

In the peptides of the present invention that were effective Hu-Asp2 substrates, Tyr/Phe and Leu were the most abundant amino acids at the $P_1$ site; Asn appeared several times at the $P_2$ site; Glu, Asp, and Ala, were prominent in the $P_1'$; Val occurred frequently in the $P_2'$; the sequence Glu-Val-Glu appeared at the $P_1'P_2'P_3'$ of ubiquitin, another Asp2 substrate; other positions did not show any obvious preferences. These observations were used to make amino acid substitutions around the cleavage site of the oxidized insulin B-chain, specifically at $P_2$-$P_3'$.

The peptides listed in Table 2 were designed, synthesized, and tested for activity as substrates for Hu-Asp2. 200 μM of each test substrate was incubated with 210 nM Hu-Asp2 enzyme at pH 4.5 at 37° C. for 3 hours. Of course it should be understood that these are merely exemplary assay conditions, and those of skill in the art will be able to vary these conditions and yet still provide appropriate Hu-Asp2 activity. For example, it is envisioned that the assays may be conducted at a pH range of from between about 4.0 to about 7.0. The amount of enzyme added to a given reaction mixture may also be varied and those of skill in the art will be able to perform assays defining the optimal enzyme concentrations necessary for a given assay, as such 150 nm; 200 nm; 250 nm; 300 nm or more or less enzyme may be added. Substrate concentration in those also may be varied such that an assay may use 100, 150 µM, 200 µM, 250 µM, 300 µM, 350 µM or more or less of any given; substrate. It may be that one substrate produces an optimum activity at one concentration whereas another substrate is needed to be present at a different concentration to produce an optimum cleavage rate. However, such optimizations of enzyme assay conditions is well within the skill of those in the art and will not require undue experimentation.

In Table 2 below, substrates that produced activity are indicated by "+" signs in which the greater the activity, the more + signs are provided. Those substrates that were not cleaved by the Hu-Asp2 are indicated by a "−" sign.

TABLE 2

| Peptide Sequence | Activity | Sequence Identifier |
|---|---|---|
| KVEALY-LV(SO3-)GER | − | SEQ ID NO: 41 |
| WRRVEALY-LVEGERK | ++ | SEQ ID NO: 42 |
| KVEANY-LVEGERKK | + | SEQ ID NO: 43 |
| KVEANY-EVEGERKK | ++++ | SEQ ID NO: 5 |
| KVEANY-AVEGERKK | ++++ | SEQ ID NO: 7 |
| KVEANY-DVEGERKK | + | SEQ ID NO: 46 |

TABLE 2-continued

| Peptide Sequence | Activity | Sequence Identifier |
|---|---|---|
| KVEANL-AVEGERKK | + | SEQ ID NO: 47 |
| KVEALY-AVEGERKK | + | SEQ ID NO: 48 |

From the above list of putative substrates, KVEANY-EVEGERKK (SEQ ID NO:5) was selected for further studies. Specifically, a Cys was inserted between R and KK to yield the peptide KVEANY-EVEGERCKK (SEQ ID NO:6). This peptide was a good substrate for Hu-Asp2. In additional steps this peptide was N-terminally biotinylated, and made fluorescent by the covalent attachment of oregon green at the Cys residue. The resulting compound, Biotin-KVEANY-EVEGERC(oregon green)KK (SEQ ID NO:49), was tested in the following conditions: 10 µM substrate, 50 nM enzyme at 37° C. The reaction was allowed to proceed for 2 hrs and samples withdrawn at several times. The results showed that 20%, 37%, 57%, and 82% cleavage occurred after 15, 30, 60, and 120 minutes, respectively. Mass spectrometry analysis showed that cleavage had occurred between Tyr and Glu only. It was shown that the new biotinylated fluorescent peptide had Vmax and Km values that were at least double the value obtained for a previous biotinylated fluorescent substrate derived from the Swedish Mutant peptide.

The EVE and AVE sequences, that appear in positions $P_1'$-$P_3'$ of SEQ ID NO:5 and SEQ ID NO:7, respectively (Table 2), were selected for additional modification. As in the case of development of the fluorescent substrate Biotin-KVEANY-EVEGERC(Oregon Green)KK (SEQ ID NO:49), the EVE sequence was selected as a starting point for modifications. Specifically, the EVE sequence in the context of the decapeptide KTITL-↓-EVEPS (SEQ ID NO:120) was selected, because the amino acid sequence in this decapeptide is an exact mimic of a stretch of ten amino acids encompassing the cleavage site L-↓-E found in ubiquitin (see SEQ ID NO:26 in Table 1).

TABLE 3

Substrate optimization for Asp2 based upon a cleavage site in ubiquitin

| Peptide | Peptide Sequence | (SEQ ID NO) | Relative rate of Cleavage+ |
|---|---|---|---|
| APP-Sw | SEVNL- ↓-DAEFR | (SEQ ID NO: 19) | 100 |
| APP-Wildtype | SEVKM-↓-DAEFR | (SEQ ID NO: 20) | 2.1* |
| Ubiquitin (Pep 1) | KTITL-↓-EVEPS | (SEQ ID NO: 120) | 13.1 |
| Peptide 2 | KTINL-↓-EVEPS | (SEQ ID NO: 133) | 92.0 |
| Peptide 3 | KTINnle-↓-EVEPS | (SEQ ID NO: 134) | 92.6 |
| Peptide 4 | KTINnle-↓-EVDPS | (SEQ ID NO: 135) | 93.6 |
| Peptide 5 | KTINnle-↓-DVDPS | (SEQ ID NO: 136) | 12.2 |
| Peptide 6 | KTISL- ↓-DVEPS | (SEQ ID NO: 137) | 69.0 |
| Peptide 7 | KTISL- ↓-DVDPS | (SEQ ID NO: 138) | 20.5 | nle = norleucine
+Assay conditions were 200 nM enzyme, and 200 µM substrate, 300 mM Na-acetate, 4% DMSO, at pH 4.5, 37° C. for 4 hr.
*24 hr reaction In addition to modifications at the $P_1'$-$P_3'$ (EVE) sites, modifications were also made at the $P_2$-$P_1$ sites. Six variants of KTITL-↓-EVEPS (SEQ ID NO: 120) were constructed and compared their activities as substrates of Asp2 to the activities shown by the Swedish mutation peptide, SEQ ID NO:19, and wild type peptide, SEQ ID NO:20 (Table 3). The ubiquitin-derived peptide having the sequence of SEQ ID NO:120, was six times better than wild type peptide, SEQ ID NO:20, but had only about 13% of the activity shown by the Swedish mutation, SEQ ID NO:19 (Table 3). However, substitution of the $P_2$ Thr with Asn generated peptide having the sequence of SEQ ID NO:133 with activity similar to that of the Swedish mutant, SEQ ID NO:19. Substitution of Leu in position $P_1$ of peptide #2 SEQ ID NO:133 with the unnatural amino acid norleucine (peptide #3 SEQ ID NO: 134) gave activity similar to that of the Swedish mutation. Also the substitution of Glu of peptide #3 SEQ ID NO:134 in $P_3'$ with Asp (peptide #4; SEQ ID NO:135) was very well tolerated. However, mutation of the two Glu residues that are at positions $P_1'$ and $P_3'$ in peptide #3 (SEQ ID NO:134), with two Asp residues, to give peptide #5 (SEQ ID NO:136), reduced the activity about 10 fold. Peptide #1, SEQ ID NO:120 was modified by putting a serine residue in $P_2$ and an Asp in position $P_1'$ to give KTISL-↓-DVEPS (peptide #6; SEQ ID NO:137). This double substitution was well tolerated, giving about 35 times more activity than wild-type peptide and 69% of the activity of Swedish mutation SEQ ID NO:19. However, when an Asp was put in place of Glu in the $P_3'$ position of peptide #6 (SEQ ID NO:137), to give peptide #7 (SEQ ID NO:138), activity dropped substantially. As observed with peptide #5 (SEQ ID NO:136), the Glu residues at positions $P_1'$ and $P_3'$ are highly preferred to Asp residues in the same positions.

Optimization of the Asp2 substrate described above leaves an Asn at $P_2$ (Table 2 and 3). This is acceptable for an in vitro assays because optimization was done within the context of insulin B-chain and ubiquitin. However, in some cases, it will be desirable to develop a cell-based assay with minimal disruption of the APP sequence. To this end, studies involving variations to the sequences of insulin B-chain and ubiquitin have yielded a great deal of information about the effects of amino acids at and near the β-secretase cleavage site of Asp2 and their effects on APP processing by this enzyme. This information can be used to modify the $P_2$-$P_2'$ residues in the sequences SEVKM-↓-DAEFR (SEQ ID NO:20)/SEVNL-↓-DAEFR (SEQ ID NO:19) (wild type/Swedish mutation) and produce minimally altered APP forms that are highly susceptible to β-secretase cleavage. Such substrates will be useful in cell-based assays for APP processing, Aβ production, and β-secretase modulation, as well as any other assay that may employ a wild-type or mutant APP.

Using the above principles, the inventors further explored the residues at the $P_2$ position of APP to discover that serine is a good replacement for Lys/Asn in the Asp2 substrates of the present invention. Thus, in particularly preferred embodiments, the amino acid at position $P_2$ in the substrates of the present invention is serine. Accordingly, replacement of the four amino acids surrounding the β-secretase cleavage site in APP, i.e. . . . KM-↓-DA . . . (SEQ ID NO:139), with . . . SY-↓-EV . . . (SEQ ID NO:140) produced the peptide SEVSY-↓-EVEFR (SEQ ID NO:141) that was hydrolyzed by Asp2 at a rate that was 70-fold greater than that seen for wild type.

Thus, the inventors have produced substrates superior to the Swedish mutation peptide (with respect to β-secretase cleavage) by changing the four amino acids . . . NL-↓-DA . . . (SEQ ID NO:142) which encompass the β-secretase cleavage site in APP Swedish mutation to . . . SY-↓-EV . . . (SEQ ID NO:141). This discovery provides the means for producing a minimally altered APP that is highly susceptible to β-secretase cleavage and therefore serves as the basis for improved cell based assays for testing for inhibitors of Asp2.

TABLE 4

Substrate optimization for Asp2 incorporating all available information

| Peptide Sequence (Sequence Listing No.) | Relative rate of Cleavage+ |
|---|---|
| SEVNL-↓-DAEFR (SEQ ID NO: 19) | 100.0 |
| SEVKM-↓-DAEFR (SEQ ID NO: 20) | 2.1* |
| SEVSY-↓-DAEFR (SEQ ID NO: 143) | 18.3 |
| SEVSY-↓-EAEFR (SEQ ID NO: 144) | 77.1 |
| SEVSY-↓-EVEFR (SEQ ID NO: 141) | 141.8 |

+Assay conditions were 200 nM enzyme, and 200 μM substrate, pH 4.5, 37° C. for 1 hr.
*24 hr reaction In Table 4, the activity of Asp2 with three newly synthesized compounds, wild type, and the Swedish mutant are compared. SEVSY-↓-DAEFR (SEQ ID NO:143) activity has increased about 9 fold over wild-type, but is still about five times less than that of the Swedish mutation SEQ ID NO:19. The substitution of the triplet KM-↓-D with SY-↓-E to give SEVSY-↓-EAEFR (SEQ ID NO:144) produced improvement of activity of the order of 40-fold over wild-type and had activity comparable to that of the Swedish mutant. A near 70-fold increase of activity over wild type peptide and a 1.4-fold increase over Swedish mutant is obtained when the four amino acids, KM-↓-DA (SEQ ID NO:139), at the active site of the wild type peptide, are substituted with SY-↓-EV (SEQ ID NO:140) to give the sequence

SEVSY-↓-EVEFR. (SEQ ID NO: 141)

In addition, the inventors generated additional substrates to further improve on substrate SEVSY-↓-EVEFR (SEQ ID NO:141) for Asp2 cleavage potential. The results are summarized in Table 5. In one strategy, SEVSY-↓-EVEFR (SEQ ID NO:141) was N-terminally extended, specifically by 5-, 10-, and 15-residues. All of the amino acids comprised in these extensions are from the APP natural sequence.

TABLE 5

Substrate optimization for Asp2

| Peptide Sequence (Sequence Listing Entry) | Relative rate of cleavage | Cleavage Activity μmol/min/mg |
|---|---|---|
| TRPGSGLTNIKTEEISEVSY-EVEFR (SEQ ID NO: 145) | 840 | 1.35 |
| GLTNIKTEEISEVSY-EVEFR (SEQ ID NO: 146) | ND | ND |
| KTEEISEVSY-EVEFR (SEQ ID NO: 147) | 360 | 0.58 |
| SEVSY-EVEFR (SEQ ID NO: 141) | 100 | 0.16 |
| TEVSY-EVEFR | 160 | 0.27 |

TABLE 5-continued Substrate optimization for Asp2

| Peptide Sequence (Sequence Listing Entry) | Relative rate of cleavage | Cleavage Activity μmol/min/mg |
|---|---|---|
| (SEQ ID NO: 148) | | |
| SEVDY-EVEFR (SEQ ID NO: 149) | 240 | 0.38 |
| TEVDY-EVEFR (SEQ ID NO: 150) | 230 | 0.37 |
| TEIDY-EVEFR (SEQ ID NO: 151) | 390 | 0.62 |
| SEISY-EVEFR (SEQ ID NO: 152) | 500 | 0.80 |
| SEIDY-EVEFR (SEQ ID NO: 153) | 430 | 0.69 |

Assay conditions were 2 nM enzyme, and 50 μM substrate, 25 mM Sodium acetate, pH 4.4, 37° C. for 2 hr.

Interestingly, TRPGSGLTNIKTEEISEVSY-EVEFR (SEQ ID NO:145), is cleaved at a rate 8.4 times faster than SEVSY-↓-EVEFR (SEQ ID NO:141), Table 5. The peptide KTEEISEVSY-EVEFR (SEQ ID NO:147) that is only 5 residues longer than SEVSY-↓-EVEFR (SEQ ID NO:141), is cleaved at a rate 3.6 times faster than the latter peptide (Table 5). In the second strategy, the inventors modified SEVSY-↓-EVEFR (SEQ ID NO:141) on the P side, specifically at the $P_5$, $P_3$, and $P_1$ positions to augment activity towards Asp2. The inventors used this strategy to yield substrates that achieved levels of activity higher than the activity observed with SEVSY-↓-EVEFR (SEQ ID NO:141) (Table 5). The particularly good substrate of the present invention is SEISY-EVEFR (SEQ ID NO:152), where Ile is taking the place of the $P_3$ Val in SEVSY-↓-EVEFR (SEQ ID NO:141). The substitution of Val with Ile resulted in a 5-fold increase in activity.

The amino acid Ile in position $P_3$ corresponds with the ubiquitin cleavage site (see Table 3). Based on the results of Table 5, the inventors expect that N-terminus extension of SEISY-EVEFR (SEQ ID NO:152) by, e.g., 5 to 15 residues, will result in a substantial increase in activity. Examples of such extended peptides include but are not limited to SEISY-EVEFRXKK (SEQ ID NO:154); KTEEISEISY-EVEFRXKK (SEQ ID NO:155); GLTNIKTEEISEISY-EVEFRXKK (SEQ ID NO:156); TRPGSGLTNIKTEEISEISY-EVEFRXKK (SEQ ID NO:157); Biotin-SEISY-EVEFRXKK (SEQ ID NO:158); Biotin-KTEEISEISY-EVEFRXKK (SEQ ID NO:159); Biotin-GLTNIKTEEISEISY-EVEFRXKK (SEQ ID NO:160); Biotin-TRPGSGLTNIKTEEISEISY-EVEFRXKK (SEQ ID NO:161) in which X is tryptophan and SEISY-EVEFRXKK (SEQ ID NO:162); KTEEISEISY-EVEFRXKK (SEQ ID NO:163); GLTNIKTEEISEISY-EVEFRXKK (SEQ ID NO:164); TRPGSGLTNIKTEEISEISY-EVEFRXKK (SEQ ID NO:165); Biotin-SEISY-EVEFRXKK (SEQ ID NO:166); Biotin-KTEEISEISY-EVEFRXKK (SEQ ID NO:167); Biotin-GLTNIKTEEISEISY-EVEFRXKK (SEQ ID NO:168); Biotin-TRPGSGLTNIKTEEISEISY-EVEFRXKK (SEQ ID NO:169) in which X is oregon green or other fluorescent moiety. Given this disclosure, it is contemplated that one of skill in the art may modify and extend any of the peptide substrates disclosed herein to provide additional useful Asp2 substrates.

Other preferred peptides of the present invention include SEISY-EVEFRWKK (SEQ ID NO:190), GLTNIK-TEEISEISY-EVEFRWKK (SEQ ID NO:191), Biotin-KEISEISY-EVEFR(Cys-Oregon Green)KK (SEQ ID NO:192) and Biotin-GLTNIKTEEISEISY-EVEFR(Cys-Oregon Green)KK (SEQ ID NO:193). In the latter two peptides the biotin facilitates capture with streptavidin and the Oregon Green provides fluorescent emission superior to the emission from the tryptophan in the peptides of SEQ ID NO: 190 and SEQ ID NO:191.

In the substrates SEISY-EVEFRWKK (SEQ ID NO:190) and GLTNIKTEEISEISY-EVEFRWKK (SEQ ID NO:191), the 10 N-terminal amino acids of peptide SEISY-EVEFR-WKK (SEQ ID NO:190) are identical to those of peptide SEISY-EVEFR (SEQ ID NO:152). The difference between the two peptide is the presence of a tryptophan and two lysines in the peptide of SEQ ID NO:190. SEISY-EVEFR-WKK (SEQ ID NO:190) and SEISY-EVEFR (SEQ ID NO:152) have comparable activities towards Hu-Asp, but the addition of the fluorescent tryptophan increased the sensitivity of the HPLC assay. Moreover the addition of two lysines increased solubility. Hu-Asp activity was tested towards SEISY-EVEFRWKK (SEQ ID NO:190) and GLTNIK-TEEISEISY-EVEFRWKK (SEQ ID NO:191). As expected the peptide of SEQ ID NO:191 was much more active than the peptide of SEQ ID NO:190. The activity difference between the two peptides was particularly dramatic in the pH range 4.0-4.6. Specifically, it was 6.3-4.8 times higher for the peptide of SEQ ID NO:191. The activity of peptide of SEQ ID NO:190 decreased more rapidly than the activity of peptide of SEQ ID NO:191 with increasing ionic strength. Both peptides were inhibited by increasing concentrations of DMSO. In studies conducted at 100 mM NaOAc/HOAc, pH 4.5, the peptide of SEQ ID NO:190 exhibited a $V_{max}$=185 nmol/mg/min and a $K_m$=86.7 μM, while the peptide of SEQ ID NO:191 exhibited a $V_{max}$=1260 nmol/mg/min and a $K_m$=43.1 μM. As expected, the N-terminus elongation increases activity. Moreover, the internally quenched peptide substrate (MCA)Ac-SEVNL-DAEFRK(Dnp)RR-NH2 (SEQ ID NO:195), that was made after the Swedish mutant APP encompassing the β-secretase cleavage site, exhibited a $V_{max}$=18 nmol/mg/min and a $K_m$=7 μM. Remarkably, a 70-fold improvement in $V_{max}$ was achieved in going from the Swedish mutant peptide of SEQ ID NO:195 to the peptide of SEQ ID NO:191. The development of the substrates of SEQ ID NO:190 and SEQ ID NO:191 is of great value in Hu-Asp inhibition studies and in studies concerning recombinant Hu-Asp refolding from E. coli inclusion bodies.

The peptide substrates of the present invention may be any length of amino acids so long as the amino acids comprise a β-secretase cleavage site that is not depicted in any of the sequences of SEQ ID NO:19; SEQ ID NO:20; SEQ ID NO:21; SEQ ID NO:26; SEQ ID NO:27; SEQ ID NO:28; SEQ ID NO:31; SEQ ID NO:32; SEQ ID NO:33; SEQ ID NO:34; SEQ ID NO:35; SEQ ID NO:36; SEQ ID NO:37; SEQ ID NO:38; SEQ ID NO:39; or SEQ ID NO:40. Preferably, the novel peptide substrates for Hu-Asp2, are at least about five amino acids in length, in certain embodiments the novel peptides of the present invention may comprise a contiguous amino acid sequence of about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, or more amino acids.

In general, the peptides of the present invention may be defined by a basic motif which is in conformance with the Schechter and Berger nomenclature, and comprises $P_2P_1$-$P_1'P_2'P_3'$; $P_2P_1$-$P_1'P_2'P_3'P_4'$; $P_3P_2P_1$-$P_1'P_2'P_3'$; $P_3P_2P_1$-

$P_1'P_2'P_3'P_4'$; $P_4P_3P_2P_1-P_1'P_2'P_3'$; $P_4P_3P_2P_1-P_1'P_2'P_3'P_4'$ in which $P_2$ is a charged amino acid, a polar amino acid, or an aliphatic amino acid but not an aromatic; $P_1$ is an aromatic amino acid or an aliphatic amino acid but not a polar amino acid or a charged amino acid; $P_1'$ is a charged amino acid, an aliphatic amino acid or a polar amino acid, but not an aromatic amino acid; $P_2'$ is an aliphatic polar amino acid or an aromatic amino acid but not a charged amino acid; $P_3'$ is preferably a charged amino acid but may be any other amino acid, $P_3$ is a polar amino acid, an aliphatic amino acid, or an aromatic amino acid but not a charged amino acid; $P_4$ is a charged amino acid, a polar amino acid or an aliphatic amino acid but not an aromatic amino acid and $P_4'$ is preferably an aromatic amino acid but may be any other amino acid.

Ultimately, it is contemplated that the sequences of the novel substrates may comprise a sequence of $P_n \ldots P_1\text{-}P_1' \ldots P_n'$. The length of the peptide may be of any length so long as the substrate comprises a β-secretase cleavage site that can be cleaved by a Hu-Asp2. The integer defined by n may be any integer so long as the substrate comprises a β-secretase cleavage site that can be cleaved by Hu-Asp2. Similarly, the integer defined by n' may be any integer so long as the substrate comprises, a β-secretase cleavage site that can be cleaved by Hu-Asp2. It is contemplated that n and n' may be the same or different. Preferably, the β-secretase cleavage site is capable of being cleaved by a human aspartyl protease encoded by the nucleic acid sequence of SEQ ID NO:1 or SEQ ID NO:3 (including the mature forms and biologically active fragments thereof).

The terms aromatic amino acid, charged amino acid, aliphatic amino acid and polar amino acid are well known to those of skill in the art and their usage in the present invention is consistent with the terms of the art. For example, the aromatic amino acids are phenylalanine, tyrosine and tryptophan, the charged amino acids (at physiological pH) are, lysine, arginine, aspartate, glutamate and occasionally histidine and the polar amino acids are aspartic acid, glutamic acid, asparagine and glutamine, the amino acids presenting aliphatic side chains are glycine, alanine, valine, leucine, isoleucine, serine and threonine.

In considering the particular amino acid to be positioned at any of the position of $P_4$, $P_3$, $P_2$, $P_1$, $P_1'$, $P_2'$, $P_3'$ or $P_4'$ it may be useful to consider the hydropathic index of amino acids at each of the positions in a peptide known to be an effective substrate for Hu-Asp2 as described herein and substitute a given amino acid with one of a similar hydropathic index. It is accepted that the relative hydropathic character of the amino acid contributes to the secondary structure of a resultant protein or peptide, which in turn defines the interaction of that protein with other molecules, for example, enzymes, substrates, receptors, DNA, antibodies, antigens, and the like. Each amino acid has been assigned a hydropathic index on the basis of their hydrophobicity and charge characteristics (Kyte & Doolittle, *J. Mol. Biol.*, 157(1):105-132, 1982, incorporated herein by reference). Generally, amino acids may be substituted by other amino acids that have a similar hydropathic index or score and still result in a protein with similar biological activity i.e., still obtain a biological functionally equivalent protein or peptide. In the context of the peptides of the present invention, a biologically functionally equivalent protein or peptide will be one which is still cleaved by β-secretase at a rate exceeding the rate of cleavage of a nature APP peptide comprising SEQ ID NO: 20.

In addition, the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As such, an amino acid can be substituted for another having a similar hydrophilicity value and still obtain a biologically equivalent and immunologically equivalent protein.

TABLE 6 depicts exemplary amino acids that will be useful at each of positions $P_4$, $P_3$, $P_2$, $P_1$, $P_1'$ $P_2'$ $P_3'$ and $P_4'$

|  | $P_4$ | $P_3$ | $P_2$ | $P_1$ | ↓ | $P_1'$ | $P_2'$ | $P_3'$ | $P_4'$ |
|---|---|---|---|---|---|---|---|---|---|
| $B_1$ | E | A | N | Y |  | E | V | E | F |
| $B_2$ | G | V | L | L |  | A | A | G | W |
| $B_3$ | I | I | K | M |  | D | N | F | G |
| $B_4$ | D | S | S | Nle |  | M | T | H | A |
| $B_5$ | T | H | G | F |  | Q | L | C* | H |
| $B_6$ | C* | Y | T | H |  | S | F | S | P |
| $B_7$ | S | T | D |  |  | G | S |  | G |
| $B_8$ |  | F | A |  |  |  |  |  | N |
| $B_9$ |  |  | Q |  |  |  |  |  | S |
| $B_{10}$ |  |  | E |  |  |  |  |  | E |

C* refers to Cysteic Acid

It is envisioned that peptides may be constructed from the above table that have for example at position $P_1$, any of the amino acids $B_1$ through $B_7$ in the $P_1$ column. Thus particular substrates that may be useful in the context of the present invention include

•ANY-EVEF (SEQ ID NO:49); E▼NY-EVEF (SEQ ID NO: 50); EA◂Y-EVEF (SEQ ID NO:51); EAN◆-EVEF (SEQ ID NO:52); EANY-◊VEF (SEQ ID NO:53); EANY-EΔEF (SEQ ID NO: 54); EANY-EV▷F (SEQ ID NO: 55); EANY-EVEΔ (SEQ ID NO: 56); •VLL-AAGW (SEQ ID NO: 57); G▼LL-AAGW (SEQ ID NO: 58); GV◂L-AAGW (SEQ ID NO: 59); GVL ◆-AAGW (SEQ ID NO: 60); GVL L-◊AGW (SEQ ID NO: 61); GVL L-A ΔGW (SEQ ID NO: 62); GVL L-AA ▷W (SEQ ID NO: 63); GVL L-AAGΔ(SEQ ID NO: 64); •IKM-DNFG (SEQ ID NO: 65); I▼KM-DNFG (SEQ ID NO: 66); II◂M-DNFG (SEQ ID NO: 67); IIK◆-DNFG (SEQ ID NO: 68); IIKM-◊NFG (SEQ ID NO: 69); IIKM-DΔFG (SEQ ID NO: 70); IIKM-DN▷G (SEQ ID NO: 71); IIKM-DNFΔ(SEQ ID NO: 72); •SSNIE-MTHA (SEQ ID NO: 73); D▼SNIE-MTHA (SEQ ID NO: 74); DS◂NIE-MTHA (SEQ ID NO: 75); DSS◆-MTHA (SEQ ID NO: 76); DSSNIE-◊THA (SEQ ID NO: 77); DSSNIE-MΔHA (SEQ ID NO: 78); DSNIE-MT▷A (SEQ ID NO: 79); DSNIE-MTHΔ(SEQ ID NO: 80); •HGF-QLC*H (SEQ ID NO: 81); T▼GF-QLC*H (SEQ ID NO: 82); TH◂F-QLC*H (SEQ ID NO: 83); THG◆-QLC*H (SEQ ID NO: 84); THGF-◊LC*H (SEQ ID NO: 85); THGF-QΔC*H (SEQ ID NO: 86); THGF-QL▷H (SEQ ID NO: 87); THGF-QLC*Δ(SEQ ID NO: 88); •YTH-SFSP (SEQ ID NO: 89); C*▼TH-SFSP (SEQ ID NO: 90); C*Y◂H-SFSP (SEQ ID NO: 91) C*YT◆-SFSP (SEQ ID NO: 92); C*YTH-◊FSP (SEQ ID NO: 93); C*YTH-SΔSP (SEQ ID NO: 94); C*YTH-SF▷P (SEQ ID NO: 95); C*YTH-SFSΔ (SEQ ID NO: 96); •TDX-GSXG (SEQ ID NO: 97); S▼DX-GSXG (SEQ ID NO: 98); ST◂X-GSXG (SEQ ID NO: 99); STD◆-GSXG (SEQ ID NO: 100); STDX-◊SXG (SEQ ID NO: 101); STDX-G▷XG (SEQ ID NO: 102); STDX-GS▷G (SEQ ID NO: 103); STDX-GSX▷ (SEQ ID NO: 104); •FAX-XXXN (SEQ ID NO: 105); X▼AX-XXXN (SEQ ID NO: 106); XF◂X-XXXN (SEQ ID NO: 107); XFA◆-XXXN (SEQ ID NO: 108); XFAX-◊XXN (SEQ ID NO: 109); XFAX-XΔXN (SEQ ID NO: 110); XFAX-XX▷N (SEQ ID NO: 111); XFAX-XXXΔ(SEQ ID NO: 112); where "X" is any amino acid; "•" denotes for example, E, G, I, D, T, C* S; "▼" denotes for example, A, V, I, S, H, Y, T, F; "◂" denotes for example, N, L, K, S, G, T, D, A, Q, E; "♦" denotes for example, Y, L, M, Nle, F, H; "◊" denotes for example, E, A, D, M, Q, S, G; "Δ" denotes for example, V, A, N, T, L, F, S; "▷" denotes for example, E, G, F, H, C*, S and "Δ" denotes for exmple, F, W, G, A, H, P, G, N, S, E.

Particularly preferred peptides of the present invention include

```
KVEANY-EVEGERKK;      (SEQ ID NO: 5)

KVEANY-EVEGERCKK;     (SEQ ID NO: 6)

KVEANY-AVEGERKK;      (SEQ ID NO: 7)

KVEANY-AVEGERCKK;     (SEQ ID NO: 8)

EANY-EVEF;            (SEQ ID NO: 9)

GVLL-AAGW;            (SEQ ID NO: 10)

IIKM-DNFG;            (SEQ ID NO: 11)

DSSNle-MTHA;          (SEQ ID NO: 12)

THGF-QLC*H;           (SEQ ID NO: 13)

CYTH-SFSP;            (SEQ ID NO: 14)

STFX-GSXG;            (SEQ ID NO: 15

XFAX-XXXN;            (SEQ ID NO: 16)

XXQX-XXXS;            (SEQ ID NO: 17)
and

XXEX-XXXE.            (SEQ ID NO: 18)
```

The above teachings enable peptide substrates for Hu-Asp2 that will prove useful in the identification of modulators of Hu-Asp2 and/or modulators of Aβ plaque formation. Methods of making and using the above-identified substrates and variants thereof are described in greater detail herein below.

II. Derivatives of the Novel Hu-Asp2 Peptide Substrates

The Hu-Asp2 substrate peptide herein provide useful core structures to construct derivatives. Such derivatives may be fusion proteins or peptides that comprise the above discussed substrates as part of their sequence, or they may be labeled or otherwise modified Hu-Asp2 substrates in which the labeling or modification may be used to facilitate the purification of the peptide, detection of the peptide itself or a detection of the cleavage product of the peptide substrate upon the action of Hu-Asp. Exemplary modifications are described in further detail herein below.

A. Fusion Polypeptides

In addition to the novel peptide substrates described above, the present invention further contemplates the generation terminal additions, also called fusion proteins or fusion polypeptides, of the Hu-Asp2 substrates described above or identified according to the present invention. This fusion polypeptide generally has all or a substantial portion of the native molecule (i.e., the Hu-Asp2 peptide substrates discussed above), linked at the N- and/or C-terminus, to all or a portion of a second or third polypeptide. It is contemplated that the fusion polypeptide may be produced by recombinant protein production or indeed by automated peptide synthesis as discussed elsewhere in the specification.

General principles for designing and making fusion proteins are well known to those of skill in the art. For example, fusions typically employ leader sequences from other species to permit the recombinant expression of a protein or peptide in a heterologous host. Another useful fusion includes the addition of an immunologically active domain, such as an antibody epitope, to facilitate purification of the fusion polypeptide. Inclusion of a cleavage site at or near the fusion junction will facilitate removal of the extraneous polypeptide after purification. The recombinant production of these fusions is described in further detail elsewhere in the specification. Other useful fusions include linking of functional domains, such as active sites from enzymes, glycosylation domains, cellular targeting signals or transmembrane regions.

More particularly, the present invention contemplates a fusion polypeptide in which there is a first component comprising the Hu-Asp2 cleavage site containing Hu-Asp2 peptide substrates of the present invention attached to a second component comprising a transmembrane domain. In additional embodiments, the fusion polypeptide further may comprise a third component which comprises a reporter gene product. In still further embodiments, the fusion polypeptides may further comprise a tagged sequence component. A particularly preferred fusion polypeptide is one which comprises a reporter gene product on one side of an intracellular transmembrane domain sequence, a short stretch of sequence containing the Hu-Asp2 cleavage site attached to a transmembrane domain with an ER/Golgi target signal, and tagged sequence on the other side of the transmembrane domain.

It is contemplated that the distance between the cleavage site and the start of a transmembrane domain is about 20-40 amino acids in order to mimic the steric properties of the APP β secretase cleavage domain. This distance may be generated from the protein conferring the transmembrane region or it may be created by means of a heterologous peptide linker. Preferably, this region is from the transmembrane protein. The transmembrane domain component of the fusion polypeptide may be essentially any transmembrane domain component that will target and locate to the Golgi or endoplasmic reticulum of a given cell. Particularly preferred membrane targeting sequences include but are not limited to the transmembrane domain of galactosyltransferase (see for example Genbank accession number AF155582), the transmembrane domain of sialyly transferase (see for example Genbank accession number NM_003032); the transmembrane domain of human aspartyl protease 1 (Asp1; see for example Genbank accession number AF200342); the transmembrane domain of human aspartyl protease 2 (Asp2; see for example Genbank accession number NM_012104); the transmembrane domain of syntaxin 6 (see for example Genbank accession number NM_005819); the transmembrane domain of acetylglucosaminyl transferase (see for example Genbank accession number NM_002406) and the transmembrane domain of APP (see for example Genbank accession number A33292). The Genbank accession numbers given above detail the complete protein sequence. For the purposes of the present invention all or part of the transmembrane domains of these proteins may be used. In specific embodiments, residues 454-477 of the Asp2, residues 598-661 of APP (e.g., of APP 695), residues 4-27 of galactosyltransferase, residues 470-492 of Asp1, residues 10-33 of sialyltransferase, residues 7-29 of acetylglucosaminyl transferase and residues 261-298 of syntaxin 6 will be particularly useful in this regard.

The reporter gene product used in the fusion polypeptides of the present invention may be any reporter protein commonly used by those of skill in the art. Exemplary reporter proteins include but are not limited to luciferase; secreted alkaline phosphatase (SEAP); β-galactosidase; β-glucorimidase; green fluorescent protein and chloramphenical acetyl transferase.

Other particular embodiments further contemplate a tagged sequence as a fourth component of the fusion polypeptides of the present invention. There are various commercially available fusion protein expression systems that may be used to provide a tagged sequence in this context of the present invention. Particularly useful systems include but are not limited to the glutathione S-transferase (GST) system (Pharmacia, Piscataway, N.J.), the maltose binding protein system (NEB, Beverley, Mass.), the FLAG system (IBI, New Haven, Conn.), and the 6xHis system (Qiagen, Chatsworth, Calif.). These systems are capable of producing recombinant polypeptides bearing only a small number of additional amino acids, which are unlikely to affect the biologically relevant activity of the recombinant fusion protein. For example, both the FLAG system and the 6xHis system add only short sequences, both of which are known to be poorly antigenic and which do not adversely affect folding of the polypeptide to its native conformation. Another N-terminal fusion that is contemplated to be useful is the fusion of a Met-Lys dipeptide at the N-terminal region of the protein or peptides. Such a fusion may produce beneficial increases in protein expression and/or activity. Specific tagged sequences that are contemplated for use in the present invention include the FLAG tag sequence DYKDDDDK (SEQ ID NO: 186) and residues 662-695 of APP.

A typical example of a preferred fusion protein of the present invention is one in which SEAP is fused to either partial or full-length insulin B chain which comprises an Asp2 cleavage site containing one of the novel Hu-Asp2 substrates described herein and the transmembrane domain of Hu-Asp2 (residue 454-477) together with a short C-terminal Flag-tagged tail. The sequence of an exemplary fusion polypeptide is depicted in the FIG. 1 (SEQ ID NO:128). In order to monitor cleavage of the chimeric construct by Hu-Asp2, the chimeric construct used alkaline phosphatase as a reporter protein. Since the peptides that can be cleaved in an in vitro assay may not be aligned well with the protease in a cellular condition, the sequences inserted between SEAP and transmembrane domain may subject to change to obtain optimal condition. Such optimization may employ peptide linkers that will provide the optimum distance between the reporter protein and the cleavage site. The Hu-Asp2 transmembrane domain will ensure efficient delivery of the insulin or ubiquitin based substrate to the cellular environment where it can bind active Hu-Asp2 and be cleaved.

An alternative design uses the C-terminal 97 amino acids from APP to mimic its natural spacing and membrane domain. Essentially, this construct will have APP transmembrane domain and most of Aβ peptide sequences except that the cleavage site is mutated from KM-DAE (SEQ ID NO:129) to a sequence of $P_2P_1$-$P_1'P_2'P_3'$ as defined above.

When the fusion protein co-expresses with Hu-Asp2 in a cell line or expresses in a cell line that produces higher Hu-Asp2 activity, Hu-Asp2 will cleave the fusion polypeptide to release SEAP into the cell medium. Thus, the protease activity may be monitored based on the SEAP activity in the medium.

As discussed in section I above, SEVSY-↓-EAEFR (SEQ ID NO:144) and SEVSY-↓-EVEFR (SEQ ID NO:141) are exemplary Asp2 peptide substrates of the present invention based on mutations of the native structure of APP. The former peptide has activity comparable to the Swedish mutation, and the latter peptide has activity superior to the Swedish mutation. In the case of SEVSY-↓-EVEFR (SEQ ID NO:141) the amino acids surrounding the β-secretase cleavage site in APP have been changed from . . . KM/NL-↓-DA . . . (in the wild type SEQ ID NO:139/Swedish mutation SEQ ID NO:142) to

...SY-↓-EV....        (SEQ ID NO: 140)

The experimental data herein indicates that the above-indicated change of only four amino acids in the APP sequence will produce an excellent APP-modified substrate for Asp2 that will give easily measurable levels of Aβ (or other detectable cleavage products) in cell-based assays. Thus, it is envisioned that the sequences SY-↓-EA (SEQ ID NO:187), or SY-↓-EV (SEQ ID NO:140), or SY-↓-AV (SEQ ID NO:188), or analogues thereof, be fused to sequences that have the ability to anchor the fusion proteins to a desired intracellular membrane such as the ER or Golgi compartments. The sequences SY-↓-EA (SEQ ID NO:187), SY-↓-EV (SEQ ID NO:140), or SY-↓-AV (SEQ ID NO:188) are used to replace the sequence KM-↓-DA (SEQ ID NO:139) in the wild type APP according to the scheme of FIG. 2 under the column labeled as "1". The peptide data herein indicates that these constructs will be readily cleaved by β-secretase, relative to cleavage rates of native APP.

FIG. 2 also describes in general terms, chimeric substrates for Asp2 cell based assays of the invention in which a reporter gene product such as SEAP is used on the ectodomain of an intracellular transmembrane segment. In a preferred embodiment, such a chimeric protein includes a short stretch of sequence containing the Asp2 cleavage site of the peptides of the present invention attached to a transmembrane domain with an ER/Golgi target signal in the middle, and a tagged sequence on the opposing side of the membrane.

An exemplary construct may be obtained by fusing SEAP to APP-CT99. The junction between SEAP and APP-CT99 is modified as shown in FIG. 2 under "2" to enhance cleavage by Asp2. Another construct may be based upon a cleavage site in ubiquitin (FIG. 2, column "3"). Specifically, SEAP is fused to ubiquitin which is C-terminally extended with the transmembrane domain of Asp2 (residue 454-477), and a short C-terminal Flag-tail. In this construct, the cleavable sequence of ubiquitin KTITL-↓-EVEPS (SEQ ID NO:120) is modified to enhance cleavage. For example, T at $P_2$ is substituted by N or S, and L at $P_1$ is substituted by Y. Other possible substitutions are indicated in FIG. 2 next to each column, and in the experimental details described herein.

When ubiquitin is used as a fusion protein, ubiquitin C-terminal residues Gly-Gly are preferably changed to some other amino acids to avoid cleavage after ubiquitin C-terminus by ubiquitin hydrolases. The Asp2 transmembrane domain will ensure efficient delivery of the construct of interest to the cellular environment where it can be recognized by active Asp2, and cleaved. When the latter fusion protein is co-expressed with Asp2 in a cell line or expressed in a cell line that produces higher Asp2 activity, Asp2 will recognize and cleave the substrate. This event will release the polypeptide (located N-terminally to the cleavage site) into the cell medium, thus allowing direct assay of the protease activity.

B. Other Modifications

In addition to providing fusion polypeptides as already described, the invention provides fusion proteins or peptide substrates that are further modified to incorporate, for example, a label or other detectable moiety.

Preferred peptide substrates will comprise internally quenched labels that result in increased detectability after cleavage of the peptide substrates. The peptide substrates may be modified to have attached a paired flurophore and quencher including but not limited to 7-amino-4-methyl coumarin and 2,4-dinitrophenol, respectively, such that cleavage of the peptide by the Hu-Asp results in increased fluorescence due to physical separation of the flurophore and quencher, which are attached on opposite sides of the scissile bond. Other paired flurophores and quenchers include bodipy-tetramethylrhodamine and QSY-5 (Molecular Probes, Inc.). In a variant of this assay, biotin or another suitable tag may be placed on one end of the peptide to anchor the peptide to a substrate assay plate and a flurophore may be placed at the other end of the peptide. Useful flurophores include those listed above as well as Europium labels such as W8044 (EG&g Wallac, Inc.). A preferred label is oregon green that may be attached to a Cys residue. Cleavage of the peptide by Asp2 will release the fluorophore or other tag from the plate, allowing compounds to be assayed for inhibition of Asp2 proteolytic cleavage as shown by an increase in retained fluorescence. Preferred colorimetric assays of Hu-Asp proteolytic activity utilize other suitable substrates that include the $P_2$ and $P_1$ amino acids comprising the recognition site for cleavage linked to o-nitrophenol through an amide linkage, such that cleavage by the Hu-Asp results in an increase in optical density after altering the assay buffer to alkaline pH.

Further, the peptides may be labeled using labels well known to those of skill in the art, e.g., biotin labels are particularly contemplated. The use of such labels is well known to those of skill in the art and is described in, e.g., U.S. Pat. No. 3,817,837; U.S. Pat. No. 3,850,752; U.S. Pat. No. 3,996,345 and U.S. Pat. No. 4,277,437. Other labels that will be useful include but are not limited to radioactive labels, fluorescent labels and chemiluminescent labels. U.S. patents concerning use of such labels include for example U.S. Pat. No. 3,817,837; U.S. Pat. No. 3,850,752; U.S. Pat. No. 3,939,350 and U.S. Pat. No. 3,996,345. Any of the peptides of the present invention may comprise one, two, or more of any of these labels.

Other derivatives specifically contemplated by the present invention include non-hydrolyzable derivatives such as statine derivatives of the β-secretase substrates of the present invention. Statine-containing peptides are recognized as having inhibitory effects on aspartyl proteases (Shewale, J. G.; Takahashi, R.; Tang, J., Aspartic Proteinases and Their Inhibitors, Kostka, V., Ed. Walter de Gruyter: Berlin (1986) pp. 101-116). Examples of statine inhibitors of cathepsin D (Lin, T.-Y.; Williams, *J. Biol. Chem.* (1979), 254, 11875-11883; Rich and Agarwal, N. S., *J. Med. Chem.* (1986) 29 (2519-2524)), and for plasmepsin (Silva, A. M. et al., *Proc. Natl. Acad Sci,* 1996, 93, 10034-10039) also have been described.

Statine is a non-standard amino acid residue present in pepstatin and is known by the chemical name (3S,4S)-4-amino-3 hydroxy-6 methylheptanoic acid and is further identified in the Merck index (11$^{th}$ Ed.) At monograph 8759. Statine is readily commercially available, for example from Sigma-Aldrich (St Louis, Mo.). The three letter abbreviation for statine is Sta in the peptide art. Statine derivatives may be prepared by methods disclosed in U.S. Pat. No. 4,397,786. Other methods are described in *The Peptides*, Vol. 5: *Analysis, Biology*; (Academic Press, NY; 1983); Kessler and Schudok, *Synthesis* (6) 457-8 (1990); Nishi and Morisawa, *Heterocycles* 29(9), 1835-42 (1989), each incorporated herein by reference. Thus, those of skill in the art will be able to use such techniques to produce statine derivatives of the present invention. WO 00/77030 describes statine-derived peptide inhibitors of the β-secretase enzyme and is specifically incorporated herein by reference as teaching methods of producing statine derivatives of peptides.

In addition to statine derivatives, many other non-hydrolyzable peptide bonds are known in the art, along with procedures for synthesis of peptides containing such bonds. Non-hydrolyzable bonds include —[$CH_2NH$]— reduced amide peptide bonds, —[$COCH_2$]— ketomethylene peptide bonds, —[CH(CN)NH]— (cyanomethylene)amino peptide bonds, —[$CH_2$ CH(OH)]— hydroxyethylene peptide bonds, —[$CH_2O$]— peptide bonds, and —[$CH_2S$]— thiomethylene peptide bonds (see e.g., U.S. Pat. No. 6,172,043).

III. Aspartyl Protease.

In addition to novel peptide substrates, the present invention is directed to methods of using such peptide substrates in various Hu-Asp2 assays. The present section provides a discussion of these proteins that have a β-secretase activity.

PCT Publication number WO 00/17369, specifically incorporated herein by reference in its entirety, describes methods and compositions relating to the identification and characterization of the β secretase enzyme, termed herein throughout as Asp2. In addition, U.S. patent application Ser. No. 09/416,901 filed Oct. 13, 1999, also is incorporated herein by reference in its entirety as providing additional disclosure regarding the nature, function, and characterization of Asp2 and the role these proteases have in AD.

These patent applications describe two isoforms of Human Asp2 referred to as Hu-Asp-2(a) and Hu-Asp2(b), may be employed in the context of the present invention, as well as fragments, analogs, orthologs, and variants thereof. All such forms may be employed in the context of the present invention, with forms that are most similar to native forms in Alzheimer's patients being preferred.

In particular embodiments, the apartyl proteases useful in the present invention are encoded by SEQ ID NO:1 or SEQ ID NO:3. The nucleic acid of SEQ ID NO:1 is predicted to encode a sequence of SEQ ID NO: 2 which is the human Asp-2(a), predicted amino acid sequence. The Asp2(a) amino acid sequence includes a putative signal peptide comprising residues 1 to 21; and a putative pre-propeptide after the signal peptide that extends through residue 45 (as assessed by processing observed of recombinant Asp2(a) in CHO cells), and a putative propeptide that may extend to at least about residue 57, based on the observation of an observed GRR↓GS sequence which has characteristics of a protease recognition sequence. The Asp2(a) further includes a transmembrane domain comprising residues 455-477, a cytoplasmic domain comprising residues 478-501, and a putative alpha-helical spacer region, comprising residues 420-454, believed to be required for proper folding of Asp2, between the protease catalytic domain and the transmembrane domain. The nucleic acid sequence of SEQ ID NO:3 is predicted to encode a sequence of SEQ ID NO: 4 which is the Human Asp-2(b), predicted amino acid sequence. The Asp2(b) amino acid sequence includes a putative signal peptide, pre-propeptide, and propeptide as described above for Asp2(a). The Asp2(b) further includes a transmembrane domain comprising residues 430-452, a cytoplasmic domain comprising residues 453-476, and a putative alpha-helical spacer region, comprising residues 395-429, believed to be required for proper folding of Asp2, between the protease catalytic domain and the transmembrane domain. As used herein, all references to "Hu-Asp2" should be understood to refer to both Hu-Asp2(a) and Hu-Asp2(b). The invention also contemplates the use of isolated or mutant Hu-Asp1, Hu-Asp2(a), and Hu-Asp2(b) polypeptides, as well as fragments thereof which exhibit aspartyl protease activity.

In yet another related aspect, the invention provides a purified polynucleotide comprising a nucleotide sequence that encodes a polypeptide having aspartyl protease activity, wherein the polypeptide has an amino acid sequence characterized by: (a) a first tripeptide sequence DTG; (b) a second tripeptide sequence selected from the group consisting of DSG and DTG; and (c) about 100 to 300 amino acids separating the first and second tripeptide sequences, wherein the polypeptide cleaves the beta secretase cleavage site of amyloid protein precursor. In one embodiment, the polypeptide comprises an amino acid sequence depicted in SEQ ID NO: 125, 2 or 4, whereas in another embodiment, the polypeptide comprises an amino acid sequence other than the amino acid sequences set forth in SEQ ID NOs: 125, 2 or 4. Similarly, the invention provides a purified polynucleotide comprising a nucleotide sequence that encodes a polypeptide that cleaves the beta secretase cleavage site of amyloid protein precursor; wherein the polynucleotide includes a strand that hybridizes to one or more SEQ ID NOs: 1, 3, and 198 under the following hybridization conditions: hybridization overnight at 42° C. for 2.5 hours in 6X SSC/0.1% SDS, followed by washing in 1.0 X SSC at 65° C., 0.1% SDS. In one embodiment, the polypeptide comprises an amino acid sequence depicted in SEQ ID NO: 125, 2 or 4, whereas in another embodiment, the polypeptide comprises an amino acid sequence other than the amino acid sequences set forth in SEQ ID NOs: 125, 2 or 4. Likewise, the invention provides a purified polypeptide having aspartyl protease activity, wherein the polypeptide is encoded by polynucleotides as described in the preceding sentences. The invention also provides a vector or host cell comprising such polynucleotides, and a method of making the polypeptides using the vectors or host cells to recombinantly express the polypeptide.

Hu-Asp variants may be obtained by Mutation of native Hu-Asp-encoding nucleotide sequences, for example. A Hu-Asp variant, as referred to herein, is a polypeptide substantially homologous to a native Hu-Asp polypeptide but which has an amino acid sequence different from that of native Hu-Asp because of one or more deletions, insertions, or substitutions in the amino acid sequence. The variant amino acid or nucleotide sequence is preferably at least about 80% identical, more preferably at least about 90% identical, and most preferably at least about 95% identical, to a native Hu-Asp sequence. Thus, a variant nucleotide sequence which contains, for example, 5 point mutations for every one hundred nucleotides, as compared to a native Hu-Asp gene, will be 95% identical to the native protein. The percentage of sequence identity, also termed homology, between a native and a variant Hu-Asp sequence may also be determined, for example, by comparing the two sequences using any of the computer programs commonly employed for this purpose, such as the Gap program (Wisconsin Sequence Analysis Package, Version 8 for Unix, Genetics Computer Group, University Research Park, Madison Wisconsin), which uses the algorithm of Smith and Waterman (Adv. Appl. Math. 2: 482-489 (1981)).

Shotgun DNA sequencing of this Asp2 genomic clone and comparison to the cDNA sequences of both Hu-Asp2 and the partial murine cDNA sequences defined the full-length sequence of murine Asp2 (SEQ ID NO: 198). The predicted amino acid sequence of murine Asp2 (SEQ ID NO: 199) showed 96.4% shared identity (GCG BestFit algorithm). with 18/501 amino acid residue substitutions compared to the human sequence. The proteolytic processing of murine Asp2 (a) is believed to be analogous to the processing described above for human Asp2(a). In addition, a variant lacking amino acid residues 190-214 of SEQ ID NO: 199 is specifically contemplated as a murine Asp2(b) polypeptide. All forms of murine Asp2(b) gene and protein are intended as aspects of the invention.

In an exemplary assay to determine the cleavage of the substrates of the present invention, Asp2 was prepared from High Five™ insect cells. Generally, the assay are run in solution at acidic pH (4.0 to 5.0), at 25-37° C. in the presence of nM or sub-nanomolar enzyme. After a suitable period of incubation the reaction is stopped at a desired time by addition of 4% trifluoracetic acid (TFA). Substrates and products are separated using reverse phase HPLC. The disappearance of the substrates and the appearance of the products are monitored by continuous measurement of the absorbance of the effluent at 220 nM. Furthermore, if the peptide comprises a tryptophan residue, the monitoring may additionally or alternatively involve continuous monitoring of fluorescence of tryptophan fluorescence (excitation at 280 nM, emission at 248 nM) of the effluent. Peptides of the present invention which comprise an Oregon Green label either alone or in addition to biotin label are particularly suitable for high throughput screening. To this end, the peptides Biotin-KEISEISY-EVEFR(Cys-Oregon Green)KK (SEQ ID NO:192) and Biotin-GLTNIKTEEISEISY-EVEFR(Cys-Oregon Green)KK (SEQ ID NO:193) are particularly suited to high throughput screening assays.

In a typical assay, 210 nM enzyme and 200 µM substrate were incubated in 0.2 M sodium acetate at pH 4.5 in 100 µl volume at 37° C. for 1 to 3 hours. The assay was stopped by the addition of 50 µl 4% TFA to lower the pH below the active range of the enzyme. Subsequently, 100 µl of this mixture was injected into a Hewlett Packard Model 1090 HPLC equipped with a Vydac column (4.6 mm i.d.×150 mm, 5 µm) pre-equilibrated with 95% A (0.15% TFA in water), 5% B (0.15% TFA in acetonitrile). The constituents were then eluted from the column with the following linear gradients: 0-15 min: 5-50% B; 15-17 min: 50-100% B; 17-20 min: 100-5% B; 20-22 min: 5% B). The cleavage products were then quantitated using an enhanced integrator.

In a variation of the above assay for substrates of SEQ ID NO:190 or its N-terminally extended version depicted in SEQ ID NO:191), the substrates were incubated with the enzyme to a final reaction solution volume of 200 µl (although reaction mixtures of 50-100 µl also were used) composed of 5-50 µM peptide substrate, 1-10 nM enzyme, 0.1. M sodium acetate buffer at pH 4 to 5. The reaction is allowed to proceed at 37° C. for 1 to 3 hrs and is terminated by addition of 100 µl 4% TFA. Subsequently, an aliquot e.g., 50 µl to 100 µl of the mixture are injected into an HPLC apparatus (Agilent 1100 series) equipped with an Alltech $C_{18}$ 3 µM Rocket column (53 mm length, 7 mm ID, part No. 50605). Solvent A for the HPLC elution of the substrates from this column was 0.1% TFA in water; Solvent B was 0.1% TFA in acetonitrile. The substrates were then eluted from the column with the following linear gradients: Time 0: 12% Solvent B; Time 4 30% Solvent B; Time 6 50% Solvent B; Time 6.5 90% Solvent B; Time 7 12% Solvent B; Time 8 12% Solvent B.

In addition to Hu-Asp, it is contemplated that the substrates of the present invention also may prove useful in assays employing other aspartyl proteases such as, for example, Asp1, Pepsin, gastricsin, cathepsin D, cathespin E and Renin.

IV. Protein or Peptide Production and Purification

The present invention provides proteins and peptide for use in the identification of modulators of Hu-Asp2. Such proteins or peptides may be produced by conventional automated peptide synthesis methods or by recombinant expression.

A. Synthetic Peptide Production

The peptides or indeed even the full length fusion polypeptides of the invention can be synthesized in solution or on a solid support in accordance with conventional techniques. Various automatic synthesizers are commercially available and can be used in accordance with known protocols. See, for example, Stewart and Young, Solid Phase Peptide Synthesis, 2d. ed., Pierce Chemical Co., (1984); Tam et al., *J. Am. Chem. Soc.*, 105:6442, (1983); Merrifield, *Science*, 232: 341-347, (1986); and Barany and Merrifield, *The Peptides*, Gross and Meienhofer, eds, Academic Press, New York, 1-284, (1979), each incorporated herein by reference. The novel Asp2 substrates of the invention which comprise the β-secretase cleavage site, can be readily synthesized and then screened in Hu-Asp2 screening assays.

In particularly preferred methods, the peptides of the present invention were synthesized by solid-phase technology employing a Model 433A from Applied Biosystems Inc. The purity of any given peptide substrate, generate through automated peptide synthesis or through recombinant methods may be determined using reverse phase HPLC analysis. Chemical authenticity of each peptide may be established by any method well known to those of skill in the art. In preferred embodiments, the authenticity is established by mass spectrometry as described in the examples.

Additionally, the peptides may be quantitated using amino acid analysis in which microwave hydrolyses are conducted. Such analyses may use a microwave oven such as the CEM Corporation's MDS 2000 microwave oven. The peptide (approximately 2 µg protein) is contacted with 6 N HCl (Pierce Constant Boiling e.g., about 4 ml) with approximately 0.5% (volume to volume) phenol (Mallinckrodt). Prior to the hydrolysis, the samples are alternately evacuated and flushed with $N_2$. The protein hydrolysis is conducted using a two-stage process. During the first stage, the peptides are subjected to a reaction temperature of about 100° C. and held that temperature for 1 minute. Immediately after this step, the temperature is increased to 150° C. and held at that temperature for about 25 minutes. After cooling, the samples are dried and amino acid from the hydrolysed peptides samples are derivatized using 6-aminoquinolyl-N-hydroxysuccinimidyl carbamate to yield stable ureas that fluoresce at 395 nm (Waters AccQ•Tag Chemistry Package). The samples may be analyzed by reverse phase HPLC and quantification may be achieved using an enhanced integrator.

B. Recombinant Protein Production.

As an alternative to automated peptide synthesis, recombinant DNA technology may be employed wherein a nucleotide sequence which encodes a peptide of the invention is inserted into an expression vector, transformed or transfected into an appropriate host cell and cultivated under conditions suitable for expression as described herein below. Recombinant methods are especially preferred for producing longer polypeptides that comprise peptide sequences of the invention.

From the disclosure of novel HuAsp2 substrate peptides sequences, it is possible to produce the peptides and fusion polypeptides by recombinant techniques. A variety of expression vector/host systems may be utilized to contain and express the peptide or fusion polypeptide coding sequence. These include but are not limited to microorganisms such as bacteria transformed with recombinant bacteriophage, plasmid or cosmid DNA expression vectors; yeast transformed with yeast expression vectors; insect cell systems infected with virus expression vectors (e.g. baculovirus); plant cell systems transfected with virus expression vectors (e.g., cauliflower mosaic virus, CaMV; tobacco mosaic virus, TMV) or transformed with bacterial expression vectors (e.g., Ti or pBR322 plasmid); or animal cell systems. Mammalian cells that are useful in recombinant protein productions include but are not limited to VERO cells, HeLa cells, Chinese hamster ovary (CHO) cell lines, COS cells (such as COS-7), W138, BHK, HepG2, 3T3, RIN, MDCK, A549, $PCl_2$, K562 and 293 cells. Exemplary protocols for the recombinant expression of the peptide substrates or fusion polypeptides in bacteria-, yeast and other invertebrates are described herein-below Expression vectors for use in prokaryotic hosts generally comprise one or more phenotypic selectable marker genes. Such genes generally encode, e.g., a protein that confers antibiotic resistance or that supplies an auxotrophic requirement. A wide variety of such vectors are readily available from commercial sources. Examples include pSPORT vectors, pGEM vectors (Promega), pPROEX vectors (LTI, Bethesda, Md.), Bluescript vectors (Stratagene), pET vectors (Novagen) and pQE vectors (Qiagen). The DNA sequence encoding the given peptide substrate or fusion polypeptide is amplified by PCR and cloned into such a vector, for example, pGEX-3X (Pharmacia, Piscataway, N.J.) designed to produce a fusion protein comprising glutathione-S-transferase (GST), encoded by the vector, and a protein encoded by a DNA fragment inserted into the vector's cloning site. The primers for the PCR may be generated to include for example, an appropriate cleavage site. Treatment of the recombinant fusion protein with thrombin or factor Xa (Pharmacia, Piscataway, N.J.) is expected to cleave the fusion protein, releasing the substrate or substrate containing polypeptide from the GST portion. The pGEX-3X/HuAsp2 peptide construct is transformed into *E. coli* XL-1 Blue cells (Stratagene, La Jolla Calif.), and individual transformants were isolated and grown. Plasmid DNA from individual transformants is purified and partially sequenced using an automated sequencer to confirm the presence of the desired peptide or polypeptide encoding nucleic acid insert in the proper orientation.

While certain embodiments of the present invention contemplate producing the peptides or polypeptides using synthetic peptide synthesizers and subsequent FPLC analysis and appropriate refolding of the cysteine double bonds, it is contemplated that recombinant protein production also may be used to produce the peptide compositions. For example, induction of the GST/substrate fusion protein is achieved by growing the transformed XL-1 Blue culture at 37° C. in LB medium (supplemented with carbenicillin) to an optical density at wavelength 600 nm of 0.4, followed by further incubation for 4 hours in the presence of 0.5 mM Isopropyl β-D-Thiogalactopyranoside (Sigma Chemical Co., St. Louis Mo.).

The GST fusion protein, expected to be produced as an insoluble inclusion body in the bacteria, may be purified as follows. Cells are harvested by centrifugation; washed in 0.15 M NaCl, 10 mM Tris, pH 8, 1 mM EDTA; and treated with 0.1 mg/ml lysozyme (Sigma Chemical Co.) for 15 minutes at room temperature. The lysate is cleared by sonication, and cell debris is pelleted by centrifugation for 10 minutes at 12,000×g. The fusion protein-containing pellet is resuspended in 50 mM Tris, pH 8, and 10 mM EDTA, layered over 50% glycerol, and centrifuged for 30 min. at 6000×g. The pellet is resuspended in standard phosphate buffered saline solution (PBS) free of $Mg^{++}$ and $Ca^{++}$. The fusion protein is further purified by fractionating the resuspended pellet in a denaturing SDS polyacrylamide gel (Sambrook et al., supra). The gel is soaked in 0.4 M KCl to visualize the protein, which is excised and electroeluted in gel-running buffer lacking SDS. If the GST/HuAsp2 fusion protein is produced in bacteria as a soluble protein, it may be purified using the GST Purification Module (Pharmacia Biotech).

The fusion protein may be subjected to thrombin digestion to cleave the GST from the mature HuAsp2 substrate peptide or the HuAsp substrate-containing polypeptide. The digestion reaction (20-40 µg fusion protein, 20-30 units human thrombin (4000 U/mg (Sigma) in 0.5 ml PBS) is incubated 16-48 hrs. at room temperature and loaded on a denaturing SDS-PAGE gel to fractionate the reaction products. The gel is soaked in 0.4 M KCl to visualize the protein bands. The identity of the protein band corresponding to the expected molecular weight of HuAsp2 substrate or fusion polypeptide may be confirmed by partial amino acid sequence analysis using an automated sequencer (Applied Biosystems Model 473A, Foster City, Calif.).

Alternatively, the DNA sequence encoding the predicted substrate containing fusion polypeptide may be cloned into a plasmid containing a desired promoter and, optionally, a leader sequence (see, e.g., Better et al., *Science,* 240:1041-43, 1988). The sequence of this construct may be confirmed by automated sequencing. The plasmid is then transformed into *E. coli* using standard procedures employing $CaCl_2$ incubation and heat shock treatment of the bacteria (Sambrook et al., supra). The transformed bacteria are grown in LB medium supplemented with carbenicillin, and production of the expressed protein is induced by growth in a suitable medium. If present, the leader sequence will effect secretion of the mature HuAsp2 substrate or fusion protein and be cleaved during secretion.

The secreted recombinant protein is purified from the bacterial culture media by the method described herein throughout.

Similarly, yeast host cells from genera including *Saccharomyces, Pichia,* and *Kluveromyces* may be employed to generate the recombinant peptide. Preferred yeast hosts are *S. cerevisiae* and *P. pastoris.* Yeast vectors will often contain an origin of replication sequence from a 2T yeast plasmid, an autonomously replicating sequence (ARS), a promoter region, sequences for polyadenylation, sequences for transcription termination, and a selectable marker gene. Vectors replicable in both yeast and *E. coli* (termed shuttle vectors) may also be used. In addition to the above-mentioned features of yeast vectors, a shuttle vector will also include sequences for replication and selection in *E. coli*. Direct secretion of polypeptides expressed in yeast hosts may be accomplished by the inclusion of nucleotide sequence encoding the yeast I-factor leader sequence at the 5' end of the substrate-encoding nucleotide sequence.

Generally, a given substrate may be recombinantly expressed in yeast using a commercially available expression system, e.g., the *Pichia* Expression System (Invitrogen, San Diego, Calif.), following the manufacturer's instructions. This system also relies on the pre-pro-alpha sequence to direct secretion, but transcription of the insert is driven by the alcohol oxidase (AOX1) promoter upon induction by methanol.

The secreted recombinant substrate is purified from the yeast growth medium by, e.g., the methods used to purify substrate from bacterial and mammalian cell supernatants.

Alternatively, a synthetic DNA encoding the novel substrate of the invention may be cloned into the baculovirus expression vector pVL1393 (PharMingen, San Diego, Calif., Luckow and Summers, *Bio/Technology* 6:47 (1988)). This substrate-containing vector is then used according to the manufacturer's directions (PharMingen) to infect *Spodoptera frugiperda* cells in sF9 protein-free media and to produce recombinant protein. The protein or peptide is purified and concentrated from the media using a heparin-Sepharose column (Pharmacia, Piscataway, N.J.) and sequential molecular sizing columns (Amicon, Beverly, Mass.), and resuspended in PBS. SDS-PAGE analysis shows a single band and confirms the size of the protein, and Edman sequencing on a Porton 2090 Peptide Sequencer confirms its N-terminal sequence.

Alternatively, the HuAsp2 substrate may be expressed in an insect system. Insect systems for protein expression are well known to those of skill in the art. In one such system, *Autographa californica* nuclear polyhedrosis virus (AcNPV) is used as a vector to express foreign genes in *Spodoptera frugiperda* cells or in *Trichoplusia larvae.* The substrate coding sequence is cloned into a nonessential region of the virus, such as the polyhedrin gene, and placed under control of the polyhedrin promoter. Successful insertion of substrate will render the polyhedrin gene inactive and produce recombinant virus lacking coat protein coat. The recombinant viruses are then used to infect *S. frugiperda* cells or *Trichoplusia* larvae in which the substrate is expressed (Smith et al., *J Virol* 46: 584, 1983; Engelhard E K et al., *Proc Nat Acad Sci* 91: 3224-7, 1994).

Mammalian host systems for the expression of recombinant proteins also are well known to those of skill in the art. Host cell strains may be chosen for a particular ability to process the expressed protein or produce certain post-translation modifications that will be useful in providing protein activity. Such modifications of the polypeptide include, but are not limited to, acetylation, carboxylation, glycosylation, phosphorylation, lipidation and acylation. Post-translational processing which cleaves a "prepro" form of the protein may also be important for correct insertion, folding and/or function. Different host cells such as CHO, HeLa, MDCK, 293, WI38, and the like have specific cellular machinery and characteristic mechanisms for such post-translational activities and may be chosen to ensure the correct modification and processing of the introduced, foreign protein.

It is preferable that the transformed cells are used for long-term, high-yield protein production and as such stable expression is desirable. Once such cells are transformed with vectors that contain selectable markers along with the, desired expression cassette, the cells may be allowed to grow for 1-2 days in an enriched media before they are switched to selective media. The selectable marker is designed to confer resistance to selection and its presence allows growth and recovery of cells which successfully express the introduced sequences. Resistant clumps of stably transformed cells can be proliferated using tissue culture techniques appropriate to the cell.

A number of selection systems may be used to recover the cells that have been transformed for recombinant protein production. Such selection systems include, but are not limited to, HSV thymidine kinase, hypoxanthine-guanine phosphoribosyltransferase and adenine phosphoribosyltransferase genes, in tk–, hgprt– or aprt– cells, respectively. Also, anti-metabolite resistance can be used as the basis of selection for dhfr, that confers resistance to methotrexate; gpt, that confers resistance to mycophenolic acid; neo, that confers resistance to the aminoglycoside G418; als which confers resistance to chlorsulfuron; and hygro, that confers resistance to hygromycin. Additional selectable genes that may be useful include trpB, which allows cells to utilize indole in place of tryptophan, or hisD, which allows cells to utilize histinol in place of histidine. Markers that give a visual indication for identification of transformants include anthocyanins, β-glucuronidase and its substrate, GUS, and luciferase and its substrate, luciferin.

C. Site-Specific Mutagenesis.

Site-specific mutagenesis is another technique useful in the preparation of individual Hu-Asp2 substrate peptide and more particularly fusion polypeptides that comprise as a component one of the Hu-Asp2 substrate peptides of the present invention. This technique employs specific mutagenesis of the underlying DNA (that encodes the amino acid sequence that is targeted for modification). The technique further provides a ready ability to prepare and test sequence variants, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

The technique typically employs a bacteriophage vector that exists in both a single stranded and double stranded form. Typical vectors useful in site-directed mutagenesis include vectors such as the M13 phage. These phage vectors are commercially available and their use is generally well known to those skilled in the art. Double stranded plasmids also are routinely employed in site directed mutagenesis, which eliminates the step of transferring the gene of interest from a phage to a plasmid.

In general, site-directed mutagenesis is performed by first obtaining a single-stranded vector, or melting of two strands of a double stranded vector which includes within its sequence a DNA sequence encoding the desired protein. An oligonucleotide primer bearing the desired mutated sequence is synthetically prepared. This primer is then annealed with the single-stranded DNA preparation, taking into account the degree of mismatch when selecting hybridization (annealing) conditions, and subjected to DNA polymerizing enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as *E. coli* cells, and clones are selected that include recombinant vectors bearing the mutated sequence arrangement.

Of course, the above described approach for site-directed mutagenesis is not the only method of generating potentially useful mutant peptide species and as such is not meant to be limiting. The present invention also contemplates other methods of achieving mutagenesis such as for example, treating the recombinant vectors carrying the gene of interest mutagenic agents, such as hydroxylamine, to obtain sequence variants.

D. Protein Purification.

It will be desirable to purify the peptides of the present invention. Protein purification techniques are well known to those of skill in the art. These techniques involve, at one level, the crude fractionation of the cellular milieu to polypeptide and non-polypeptide fractions. Having separated the peptide or polypeptides of the invention from other proteins, the polypeptides or peptides of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. A particularly efficient method of purifying peptides is fast protein liquid chromatography (FPLC) or even high performance liquid chromatography (HPLC).

Certain aspects of the present invention concern the purification, and in particular embodiments, the substantial purification, of an encoded polypeptide, protein or peptide. The term "purified polypeptide, protein or peptide" as used herein, is intended to refer to a composition, isolated from other components, wherein the polypeptide, protein or peptide is purified to any degree relative to its naturally-obtainable state. A purified polypeptide, protein or peptide therefore also refers to a polypeptide, protein or peptide, free from the environment in which it may naturally occur.

Generally, "purified" will refer to a polypeptide, protein or peptide composition that has been subjected to fractionation to remove various other components, and which composition substantially retains its expressed biological activity. Where the term "substantially purified" is used, this designation will refer to a composition in which the polypeptide, protein or peptide forms the major component of the composition, such as constituting about 50%, about 60%, about 70%, about 80%, about 90%, about 95% or more of the proteins in the composition.

Various methods for quantifying the degree of purification of the polypeptide, protein or peptide will be known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number." The actual units used to represent the amount of activity will, of course, be dependent upon the particular assay technique chosen to follow the purification and whether or not the expressed polypeptide, protein or peptide exhibits a detectable activity.

Various techniques suitable for use in protein purification will be well known to those of skill in the art. These include, for example, precipitation with ammonium sulphate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified polypeptide, protein or peptide.

There is no general requirement that the polypeptide, protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

It is known that the migration of a polypeptide can vary, sometimes significantly, with different conditions of SDS/PAGE (Capaldi et al., *Biochem. Biophys. Res. Comm.*, 76:425, 1977). It will therefore be appreciated that under differing electrophoresis conditions, the apparent molecular weights of purified or partially purified expression products may vary.

V. Expression Constructs for Use in the Production of the Substrates of the Invention.

In the present invention, it may be necessary to express the peptide substrates or the peptide substrate fusion proteins of the present invention. To achieve such expression, the present invention will employ vectors comprising polynucleotide molecules for encoding the peptide substrates or the fusion proteins of the present invention, as well as host cell transformed with such vectors. Such polynucleotide molecules may be joined to a vector, which generally includes a selectable marker and an origin of replication, for propagation in a host. These elements of the expression constructs used in the present invention are described in further detail herein below.

The expression vectors include DNA encoding any of the given peptide or fusion polypeptide Hu-Asp2 substrates described above or below, operably linked to suitable transcriptional or translational regulatory sequences, such as those derived from a mammalian, microbial, viral, or insect gene. Examples of regulatory sequences include transcriptional promoters, operators, or enhancers, mRNA ribosomal binding sites, and appropriate sequences which control transcription and translation.

The terms "expression vector," "expression construct" or "expression cassette" are used interchangeably throughout this specification and are meant to include any type of genetic construct containing a nucleic acid coding for a gene product in which part or all of the nucleic acid encoding sequence is capable of being transcribed.

The choice of a suitable expression vector for expression of the peptides or polypeptides of the invention will of course depend upon the specific host cell to be used, and is within the skill of the ordinary artisan. Examples of suitable expression vectors include pcDNA3 (Invitrogen) and pSVL (Pharmacia Biotech). A preferred vector for expression in the present invention is pcDNA3.1-Hygro (Invitrogen). Expression vectors for use in mammalian host cells may include transcriptional and translational control sequences derived from viral genomes. Commonly used promoter sequences and enhancer sequences which may be used in the present invention include, but are not limited to, those derived from human cytomegalovirus (CMV), Adenovirus 2, Polyoma virus, and Simian virus 40 (SV40). Methods for the construction of mammalian expression vectors are disclosed, for example, in Okayama and Berg (*Mol. Cell. Biol.* 3:280 (1983)); Cosman et al. (*Mol. Immunol.* 23:935 (1986)); Cosman et al. (*Nature* 312:768 (1984)); EP-A-0367566; and WO 91/18982.

The expression construct will comprise a nucleic acid region that encodes the particular peptide substrate or fusion polypeptide of the present invention. Coding regions for use in constructing such expression vectors should encode at least the β-secretase cleavage of the peptides described herein although it is contemplated that larger polypeptides may be encoded as long as one the peptide generated comprises a β-secretase cleavage site that is amenable to cleavage by an aspartyl protease and preferably Hu-Asp.

In certain aspects of the present invention, the expression construct may further comprise a selectable marker that allows for the detection of the expression of the peptide or polypeptide. Usually the inclusion of a drug selection marker aids in cloning and in the selection of transformants, for example, neomycin, puromycin, hygromycin, DHFR, zeocin and histidinol. Alternatively, enzymes such as herpes simplex virus thymidine kinase (tk) (eukaryotic), β-galactosidase, luciferase, or chloramphenicol acetyltransferase (CAT) (prokaryotic) may be employed. Immunologic markers also can be employed. For example, epitope tags such as the FLAG system (IBI, New Haven, Conn.), HA and the 6×His system (Qiagen, Chatsworth, Calif.) may be employed. Additionally, glutathione S-transferase (GST) system (Pharmacia, Piscataway, N.J.), or the maltose binding protein system (NEB, Beverley, Mass.) also may be used. The selectable marker employed is not believed to be important, so long as it is capable of being expressed simultaneously with the nucleic acid encoding a gene product. Further examples of selectable markers are well known to one of skill in the art. Particularly preferred selectable markers that may be employed in the present invention are neomycin resistance or a GFP marker.

Expression requires that appropriate signals be provided in the vectors. The present section includes a discussion of various regulatory elements, such as enhancers/promoters from both viral and mammalian sources that may be used to drive expression of the nucleic acids of interest in host cells. Elements designed to optimize messenger RNA stability and translatability in host cells also are defined. The conditions for the use of a number of dominant drug selection markers for establishing permanent, stable cell clones expressing the products also are provided, as is an element that links expression of the drug selection markers to expression of the mutant phenotype.

In preferred embodiments, the nucleic acid encoding the given peptide or the nucleic acid encoding a selectable marker is under transcriptional control of a promoter. A "promoter" refers to a DNA sequence recognized by the synthetic machinery of the cell, or introduced synthetic machinery, required to initiate the specific transcription of a gene.

Nucleotide sequences are operably linked when the regulatory sequence functionally relates to the DNA encoding the peptide substrate or the fusion polypeptide. Thus, a promoter nucleotide sequence is operably linked to a given DNA sequence if the promoter nucleotide sequence directs the transcription of the sequence. Similarly, the phrase "under transcriptional control" means that the promoter is in the correct location and orientation in relation to the nucleic acid to control RNA polymerase initiation and expression of the gene.

The term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7-20 bp of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either cooperatively or independently to activate transcription.

The particular promoter employed to control the expression of a nucleic acid sequence of interest is not believed to be important, so long as it is capable of directing the expression of the nucleic acid in the targeted cell. Thus, where a human cell is targeted, it is preferable to position the nucleic acid coding region adjacent to and under the control of a promoter that is capable of being expressed in a human cell. Generally speaking, such a promoter might include either a human or viral promoter.

In various embodiments, the human cytomegalovirus (CMV) immediate early gene promoter, the SV40 early promoter, the Rous sarcoma virus long terminal repeat, β-actin, rat insulin promoter, the phosphoglycerol kinase promoter and glyceraldehyde-3-phosphate dehydrogenase promoter, all of which are promoters well known and readily available to those of skill in the art, can be used to obtain high-level expression of the coding sequence of interest. The use of other viral or mammalian cellular or bacterial phage promoters which are well-known in the art to achieve expression of a coding sequence of interest is contemplated as well, provided that the levels of expression are sufficient for a given purpose. By employing a promoter with well known properties, the level and pattern of expression of the protein of interest following transfection or transformation can be optimized.

Selection of a promoter that is regulated in response to specific physiologic or synthetic signals can permit inducible expression of the gene product. Several inducible promoter systems are available for production of viral vectors. One such system is the ecdysone system (Invitrogen, Carlsbad, Calif.), which is designed to allow regulated expression of a gene of interest in mammalian cells. It consists of a tightly regulated expression mechanism that allows virtually no basal level expression of the transgene, but over 200-fold inducibility.

Another useful inducible system is the Tet-Off™ or Tet-On™ system (Clontech, Palo Alto, Calif.) originally developed by Gossen and Bujard (Gossen and Bujard, *Proc Natl Acad Sci USA*. 15;89(12):5547-51, 1992; Gossen et al., *Science*, 268(5218):1766-9, 1995).

In mammalian cells, the CMV immediate early promoter if often used to provide strong transcriptional activation. Modified versions of the CMV promoter that are less potent have also been used when reduced levels of expression of the transgene are desired. Retroviral promoters such as the LTRs from MLV or MMTV are contemplated to be useful in the present invention. Other viral promoters that may be used include SV40, RSV LTR, HIV-1 and HIV-2 LTR, adenovirus promoters such as from the E1A, E2A, or MLP region, AAV LTR, cauliflower mosaic virus, HSV-TK, and avian sarcoma virus.

In some embodiments, regulatable promoters may prove useful. Such promoters include for example, those that are hormone or cytokine regulatable. Hormone regulatable promoters include MMTV, MT-1, ecdysone and RuBisco as well as other hormone regulated promoters such as those responsive to thyroid, pituitary and adrenal hormones.

Another regulatory element contemplated for use in the present invention is an enhancer. These are genetic elements that increase transcription from a promoter located at a distant position on the same molecule of DNA. Enhancers are organized much like promoters. That is, they are composed of many individual elements, each of which binds to one or more transcriptional proteins. The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization. Enhancers useful in the present invention are well known to those of skill in the art and will depend on the particular expression system being employed (Scharf D et al (1994) *Results Probl Cell Differ* 20: 125-62; Bittner et al (1987) *Methods in Enzymol* 153: 516-544).

Where an expression construct employs a cDNA insert, one will typically desire to include a polyadenylation signal sequence to effect proper polyadenylation of the gene transcript. Any polyadenylation signal sequence recognized by cells of the selected transgenic animal species is suitable for the practice of the invention, such as human or bovine growth hormone and SV40 polyadenylation signals.

Also contemplated as an element of the expression cassette is a terminator. These elements can serve to enhance message levels and to minimize read through from the cassette into other sequences. The termination region which is employed primarily will be one selected for convenience, since termination regions for the applications such as those contemplated by the present invention appear to be relatively interchangeable. The termination region may be native with the transcriptional initiation, may be native to the DNA sequence of interest, or may be derived for another source.

In certain embodiments of the invention, the use of internal ribosome entry site (IRES) elements is contemplated to create multigene, or polycistronic, messages. IRES elements are able to bypass the ribosome scanning model of 5' methylated Cap dependent translation and begin translation at internal sites (Pelletier and Sonenberg, *Nature*, 334:320-325, 1988). IRES elements from two members of the picornavirus family (poliovirus and encephalomyocarditis) have been described (Pelletier and Sonenberg, 1988 supra), as well an IRES from a mammalian message (Macejak and Sarnow, *Nature*, 353: 90-94, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message.

Any heterologous open reading frame can be linked to IRES elements. This includes genes for secreted proteins, multi-subunit proteins, encoded by independent genes, intracellular or membrane-bound proteins and selectable markers. In this way, expression of several proteins can be simultaneously engineered into a cell with a single construct and a single selectable marker.

VI. Use of the Substrates in Hu-Asp2 Assays

In specific embodiments, the present invention involves assays to monitor the activity and/or function of Hu-Asp2 and more specifically, the β-secretase activity and/or function of Hu-Asp2. These assays will involve incubating in solution an Hu-Asp2 polypeptide with a suitable substrate of the present invention, using cleavage of the peptide substrate as a measure of Hu-Asp2 proteolytic activity.

A. Assay Formats

In specific embodiments, the invention relates to a method for the identification of agents that modulate the activity of human Asp2 aspartyl protease (Hu-Asp2). For example, in one variation, such method comprises steps of:

(a) contacting any of the peptides or fusion proteins of the present invention and a composition comprising an Hu-Asp2 activity in the presence and absence of a test agent;

(b) determining the cleavage of said peptide or fusion protein at the site between said $P_1$ and $P_1'$ by said Hu-Asp2 in the presence and absence of the test agent; and (c) comparing said cleavage activity of the Hu-Asp2 in the presence of the test agent to the activity in the absence of the test agent to identify an agent that modulates said cleavage by the Hu-Asp2, wherein an alteration in the Hu-Asp2 activity in the presence of the test agent identifies an agent that is a modulator of the Hu-Asp2 activity.

Agents that cause increased cleavage relative to the control (no test agent) are scored as agonists or stimulators of Asp2 proteolytic activity, whereas agents to cause decreased cleavage are scored as inhibitors. The inhibitors are of special interest because inhibitors of Asp2 activity have therapeutic and prophylactic indications for the treatment and prevention of Alzheimer's Disease or its symptoms or progression.

Exemplary assays which can be modified by the use of peptides and fusion proteins of the invention (in place of APP and APP peptide sequences) are described in PCT Publication number WO 00/17369, and in U.S. patent application Ser. No. 09/416,901, filed Oct. 13, 1999, both incorporated herein by reference for their teachings relating to Asp2 activity assays and assays for modulators of Asp2 activity. The Asp2 may be Hu-Asp2(a), Hu-Asp2(b), or biologically active fragments, analogs, or variants, thereof, for example. Non-human orthologs of human Asp2 also may be used in assays.

Such assays may be performed with Hu-Asp polypeptide in a cell free system or with cultured cells that express Hu-Asp as well as variants or isoforms thereof. For example, in a cell-free system, the contacting step may be performed by mixing the Hu-Asp2 enzyme with the peptide or protein substrate of the invention, in the presence or absence of the test agent. For optimal results, the enzyme and the substrate preferably are substantially purified, mixed in defined and controlled quantities, and mixed in appropriate buffers that optimize enzymatic activity and/or mimic physiological conditions. The determining step may involve a measurement of an N-terminal fragment, a C-terminal fragment, or both, or may involve measurement of another parameter indicative of cleavage. For example, the peptide substrate may contain a quenched label that becomes more detectable only upon cleavage to separate the label from the quenching moiety. Alternatively, the peptide substrate may be fixed at the N-terminal or C-terminal end to a solid support. In this arrangement, cleavage may be measured by release from the solid support of a cleavage fragment. The release may be measured by increased label in the media, or decreased label attached to the solid support. Alternatively, the release may be measured by quantitative capture of the released peptide (e.g., with an antibody).

In an exemplary capture assay, 384-well micro-titer plates are blocked with BSA enzyme (7.5 nM) and 50 µM of the compound to be tested are incubated for 1 hour and the reaction is initiated by the addition of 250 nM substrate, for example Bition-KVEANYEVEGERC[cys-oregon green] KK. In the final assay conditions, the volume is 30 µl/well (pH5.0); 50 µM compound; 7.5 nM Enzyme (or 15 ng/well); 250 nM substrate; 5% DMSO and 0.001% TWEEN-20. The assay is incubated overnight at room temperature and the reaction is terminated by the addition of Tris-HCl, pH 8.3. An aliquot containing 6.25 pmoles of substrate is removed and the cleaved and/or uncleaved biotinylated substrate is captured in a streptavidin coated plate. The plate is washed 3 time and buffer is added. The capture assay is monitored by reading the fluorescence emission of the oregon green on an LJL Analyst (Ex 485/Em 530).

Another assay that may be used herein is a fluorescent polarization assay. Fluorescence polarization is a sensitive, facile and non-destructive assay that can be exploited to monitor the effects of the β-secretase substrates of the present invention. It can be used to monitor the interaction of these substrates with the HuAsp2 enzyme. Under controlled conditions, fluorescence polarization measurements can reveal the extent of "molecular tumbling" of a fluorescent molecule in solution. For example, a small molecule with a compact molecular volume would be expected to tumble rapidly. If irradiated with polarized light the rapid movement of the molecule in solution would result in extensive depolarization of the light, and would yield a readout of "low" polarization value. Under the same conditions, the increased molecular volume of a large molecule or a large complex would slow the molecular rotation (tumbling) process. As a result, less polarization of the incident plane polarized light would result and a higher polarization value would be measured.

By labeling a small ligand with a fluorescent probes, changes in the fluorescence polarization resulting from the interaction of the ligand with another system component can be measured. Such a method may be applied to measure the strength of interaction between an enzyme (HuAsp2) and a fluorescent enzyme substrate.

In an exemplary fluorescence polarization assay, in pre-blocked low affinity, black plates (384-wells) enzyme (0.5 nM) and compound (10-20 µM) are incubated for 30 minutes and the reaction initiated by the addition of 150 nM substrate (e.g., Biotin-GLNIKTEEISEISY-EVEFR[cys-oregon green] KK or a similar substrate containing a non-hydrolyzable bond at the $P_1$--$P_1'$ position) to a final volume of 30 µl/well. The final assay conditions are: 30 µl/well volume at pH4.5; 50 µM compound, 0.5 nM enzyme or 1 ng/well; 150 nM substrate, 2% DMSA and 0.001% TWEEN-20. The assay is incubated for 3 hours at 37° C. and the reaction terminated by the addition of a saturating concentration of immunopure streptavidin. The plate is then incubated at room temperature for 15 minutes and the fluorescent polarization measured on an LJL Acquest (Ex 485/Em 530).

Also contemplated by the present invention is a binding assay for detecting compounds that bind to the active site or at an allosteric site of the enzyme. For such determinations, the use of non-hydrolyzable derivatives of the substrates of the present invention is particularly preferred. In exemplary derivatives for such assays, the presence of a statine derivative at $P_1$ renders the peptides of the present invention non-hydrolyzable at the $P_1$--$P_1'$ position. The substrates further may be modified with the addition of ante fluorescent tag e.g., BODIPY FL to facilitate detection.

In a specific example, a statine-containing peptide (SEVN[Sta]VAEFRGGC; SEQ ID NO:196) is synthesized and shown to inhibit HuAsp enzyme activity. A fluorescent derivative of this inhibitor, (SEVN[Sta]VAEFRC(Bodipy FL)), also was synthesized and employed as described below. The fluorescence polarization of these statine-derived substrates in solution is minimal. However, upon interaction with HuAsp2 a dramatic increase in fluorescence polarization results. While the examples discussed in the present section refer to statine derivatives, it is contemplated that other non-hydrolyzable derivatives containing a fluorescent moiety may be used in the fluorescence polarization assays.

A substrate of the present invention may be labeled as discussed above and used to develop a fluorescence polarization binding assay for the HuAsp2. The equilibrium dissociation constant ($K_D$) for the interaction between the enzyme and the substrate is determined by measuring fluorescence polarization changes which result from titrating the substrate with the enzyme.

To determine the $K_D$ for the interaction of a substrate of the present invention with HuAsp2, various quantities of β-secretase may be combined with 3.1 nM fluorescent substrate and incubated at room temperature for 3 hours. Following the incubation, fluorescence polarization is determined using an LJL Analyst (96 well format) or a PanVera Beacon (single cuvette format). An exemplary assay is performed in 25 mM sodium acetate, 20% glycerol, pH 4.75. A graphic plot of the data obtained providing the polarization values on the vertical axis and the concentration of enzyme on the horizontal axis provides the binding isotherm for the determination of the $K_D$ for the interaction of the enzyme with the substrate. The data may then be analyzed using the relation $Px=PF+(PB-PF)*[E]/(K_D+[E])$, where P=polarization value, x=sample, F=free inhibitor, B=bound inhibitor, E=β-secretase (Fluorescence Polarization Applications Guide, 1998; PanVera, Madison, Wis.) to obtain the $K_D$. This assay can be used to screen for compounds that bind to the active site of the enzyme.

Using the above assay, the fluorescence polarization binding assay may be validated and the $K_D$ measured for a peptide substrate containing the wild-type or Swedish mutation. For example, such a initial assay may be performed using the fluorescent derivative, (SEVN[Sta]VAEFRC(Bodipy FL)). Subsequently, the assay may be modified for use in a competitive binding format for use in determining the activity of useful substrates of the present invention. A solution containing the SEVN[Sta]VAEFRC(Bodipy FL) substrate is titrated with a prospective competitive inhibitor, for example, 3.1 nM SEVN[Sta]VAEFRC(Bodipy FL) substrate, 48 nM enzyme and various concentrations of the prospective competitive inhibitor are incubated for an appropriate time to allow the reaction to progress. The data from this assay may be plotted on a graph where the vertical axis represents the polarization and the horizontal axis represents the competitive inhibitor concentration.

Numerous cell-based embodiments also exist. For example, in one variation, the Hu-Asp2 is expressed in a cell, and the contacting comprises growing the cell in the presence of the peptide and in the presence and absence of the test agent. Cells which naturally express Asp2 may be selected. In a preferred embodiment, a cell is recombinantly modified to express increased amounts of Asp2. Irrespective of which variation is used, the substrate peptide or fusion protein may be added to the cell system (e.g., in the medium), or may be co-expressed by the cell along with the Asp2. For example, in a preferred embodiment, the cell recombinantly expresses a fusion polypeptide described herein that includes a transmembrane domain that causes the peptide to localize to the ER or Golgi, and further includes appropriate tags, labels, fusion partners, reporter protein or the like as described herein to facilitate detection of cleavage.

In an exemplary cellular assay, a stable HEK-293 cell line expressing HA-gagged enzyme is transfected with APP variants. After transfection for 48 hours, cell extracts are prepared for measuring Hu-Asp cleavage products C99 by Western blot with antibody C8. Equal amount of conditioned medium are used for measuring the levels of total secreted APP fragments with antibody 22C11 (Boehringer Mannheim) and secreted APPα, a fragment cleaved by α-secretase, with antibody 6E10 (Senetek, St. Louis, Mo.).

It will be appreciated that the activity measurements in the presence and absence of a test agent can be performed in parallel, or sequentially, in either order. Moreover, it may not be necessary to repeat the control measurements (i.e., the measurements of cleavage in the absence of a test agent)-in-parallel-with-respect to every test agent, once a reliable baseline of enzymatic activity for particular reaction conditions has been obtained. Gained knowledge of the enzymatic activity of Asp2 towards a particular substrate in the absence of inhibitors can be used as the basis for performing the comparison step.

Also, while the above discussion is generally made with reference to modulators of Hu-Asp2 activity, the assays of the invention also will identify candidate substances that alter the production of Hu-Asp2, thereby increasing or decreasing the amount of Hu-Asp2 present as opposed to the per unit activity of the Hu-Asp2. Agents that decrease production of Hu-Asp2 also have indications for treatment or prevention of Alzheimer's disease.

B. Candidate Substances.

As used herein the term "candidate substance" or "test substance" refers to any molecule that is capable of modulating Hu-Asp2 activity, and preferably Hu-Asp2 β-secretase activity. In specific embodiments, the molecule is one which modulates Hu-Asp2 activity. The candidate substance may be a protein or fragment thereof, a small molecule inhibitor, or even a nucleic acid molecule. It may prove to be the case that the most useful pharmacological compounds for identification through application of the screening assay will be compounds that are identified through screening large compound libraries or that are structurally related to other known modulators of APP processing. The active compounds may include fragments or parts of naturally-occurring compounds or may be only found as active combinations of known compounds which are otherwise inactive. However, prior to testing of such compounds in humans or animal models, it will be necessary to test a variety of candidates to determine which have potential.

Accordingly, the active compounds may include fragments or parts of naturally-occurring compounds or may be found as active combinations of known compounds which are otherwise inactive. Accordingly, the present invention provides screening assays to identify agents which stimulate or inhibit cellular APP processing. It is proposed that compounds isolated from natural sources, such as animals, bacteria, fungi, plant sources, including leaves and bark, and marine samples may be assayed as candidates for the presence of potentially useful pharmaceutical agents.

It will be understood that the pharmaceutical agents to be screened could also be derived or synthesized from chemical compositions or man-made compounds. Thus, it is understood that the candidate substance identified by the present invention may be polypeptide, polynucleotide, small molecule inhibitors or any other inorganic or organic chemical compounds that may be designed through rational drug design starting from known stimulators or inhibitors of Hu-Asp2 activity and/or APP processing.

The candidate screening assays are simple to set up and perform. Thus, in assaying for a candidate substance, after obtaining a cell expressing functional Hu-Asp, one will admix a candidate substance with the cell, under conditions which would allow measurable Hu-Asp2 activity to occur. In this fashion, one can measure the ability of the candidate substance to stimulate the activity of the cell in the absence of the candidate substance. Likewise, in assays for inhibitors after obtaining a cell expressing functional Hu-Asp, the candidate substance is admixed with the cell. In this fashion the ability of the candidate inhibitory substance to reduce, abolish, or otherwise diminish a biological effect mediated by Hu-Asp2 from said cell may be detected.

"Effective amounts" of the substance in certain circumstances are those amounts effective to reproducibly alter a given Hu-Asp2 activity or APP processing in the form of cleavage of the β-secretase cleavage site of the peptide substrates of the present invention in comparison to their normal levels of cleavage in the absence of the candidate substance. Compounds that achieve significant appropriate changes in activity will be used.

Significant changes in Hu-Asp2 activity or function, e.g., as measured using cleavage of the novel Hu-Asp2 peptide substrates of the present invention (see e.g., Example 1) are represented by an increase/decrease in activity of at least about 30%-40%, and most preferably, by changes of at least about 50%, with higher values of course being possible.

The assays described above employing the novel Hu-Asp2 substrates of the invention are amenable to numerous high throughput screening (HTS) methods (For a review see Jayawickreme and Kost, *Curr. Opin. Biotechnol.* 8: 629-634 (1997)). Automated and miniaturized HTS assays are also contemplated as described for example in Houston and Banks *Curr. Opin. Biotechnol.* 8: 734-740 (1997)

There are a number of different libraries used for the identification of small molecule modulators including chemical libraries, natural product libraries and combinatorial libraries comprised or random or designed peptides, oligonucleotides or organic molecules. Chemical libraries consist of structural analogs of known compounds or compounds that are identified as hits or leads via natural product screening or from screening against a potential therapeutic target. Natural product libraries are collections of products from microorganisms, animals, plants, insects or marine organisms which are used to create mixtures of screening by, e.g., fermentation and extractions of broths from soil, plant or marine organisms. Natural product libraries include polypeptides, non-ribosomal peptides and non-naturally occurring variants thereof. For a review see *Science* 282:63-68 (1998). Combinatorial libraries are composed of large numbers of peptides oligonucleotides or organic compounds as a mixture. They are relatively simple to prepare by traditional automated synthesis methods, PCR cloning or other synthetic methods. Of particular interest will be libraries that include peptide, protein, peptidomimetic, multiparallel synthetic collection, recombinatorial and polypeptide libraries. A review of combinatorial libraries and libraries created therefrom, see Myers *Curr. Opin. Biotechnol.* 8: 701-707 (1997). A candidate modulator identified by the use of various libraries described may then be optimized to modulate activity of Hu-Asp2 through, for example, rational drug design.

It will, of course, be understood that all the screening methods of the present invention are useful in themselves notwithstanding the fact that effective candidates may not be found. The invention provides methods for screening for such candidates, not solely methods of finding them.

C. In Vivo Assays.

The present invention also encompasses the use of various animal models. Given the disclosure of the present invention, it will be possible to produce non-human models of APP precessing in which the normal APP β-secretase cleavage site has been replaced by the peptide substrates of the present invention. This will afford an excellent opportunity to examine the function of Hu-Asp2 in a whole animal system where it is normally expressed. By developing or identifying mice that express the novel β-secretase substrates of the present invention, one can provide models that will be highly predictive of Alzheimer's disease in humans and other mammals, and helpful in identifying potential therapies. Methods of creating such animals are detailed elsewhere in the specification.

Treatment of animals with test compounds will involve the administration of the compound, in an appropriate form, to the animal. Administration will be by any route that can be utilized for clinical or non-clinical purposes, including but not limited to oral, nasal, buccal, rectal, vaginal or topical. Alternatively, administration may be by intratracheal instillation, bronchial instillation, intradermal, subcutaneous, intramuscular, intraperitoneal or intravenous injection. Specifically contemplated are systemic intravenous injection, regional administration via blood, cerebrospinal fluid (CSF) or lymph supply and intratumoral injection.

Determining the effectiveness of a compound in vivo may involve a variety of different criteria. Such criteria include, but are not limited to, survival, increased activity level, and improved food intake. Other methods of evaulation include pathological examination, especially of brain tissue, to look for indicia of altered beta secretase activity, such as reduced production of amyloid beta or amyloid beta plaques and reduced atrophy of the brain.

D. Manufacture of Medicaments

The assays of the invention will identify beta secretase modulators that represent candidate therapeutics for treatment of diseases characterized by aberrant levels of beta secretase activity, including Alzheimer's disease. Thus, after identifying modulator agents, the methods of the invention optionally include the additional step or steps of manufacturing/synthesizing the agents, and of formulating the agent into a composition using pharmaceutically acceptable diluents, adjuvants, or carriers. Pharmaceutical compositions are described in greater detail below.

VII. Methods of Making Transgenic Animals

As noted above, particular embodiments of the present invention contemplate the production of transgenic animals comprising an APP mutant having as β-secretase cleavage one of the peptides of the present invention. Exemplary transgenic animals of the present invention are constructed using an expression cassette which includes in the 5'→3' direction of transcription, a transcriptional and translational initiation region associated with expression in the host animal (a promoter region as described below), a DNA encoding a mutant APP gene that when expressed as a protein lacks the wild-type or Swedish sequence at the β-secretase cleavage site and instead comprises a sequence of one of the novel Hu-Asp2 peptide substrates of the present invention and/or a selectable marker gene, and a transcriptional and translational termination region functional in the host animal.

The transgenic animals will provide models for the study of the function of Hu-Asp2 and for the development of protocols and regimens for the therapeutic intervention of AD. Preferred animals exhibit characteristics associated with the pathophysiology of AD. Transgenic animals expressing the mutant APP transgenes, recombinant cell lines derived from such animals, and transgenic embryos are all within the purview of this aspect of the invention.

A. Animals Used.

In certain instances, it may be useful to set up a colony of mice for the production of transgenic mice and also for the production of colonies that may be employed for testing the effects of various antidepressant agents. The animals used as a source of fertilized egg cells or embryonic stem cells can by any animal. However, it is generally preferred that the host animal is one which lends itself to multi-generational studies. Transgenic animals may be produced from the fertilized eggs from a number of animals including, but not limited to reptiles, amphibians, birds, mammals, and fish. Within a particularly preferred embodiment, transgenic mice are generated which express a mutant form of APP which comprises a secretase cleavage site of one of the peptides of the present invention in place of the wild-type or Swedish mutation sequence. While this section generally discusses mouse colonies, it should be understood that similar considerations will apply to any animals that are employed in or generated according to the present invention.

The animals of a colony for the production and analysis of transgenic animals can be divided into five categories: female animals for matings to produce fertilized eggs; fertile stud males; sterile stud males for producing pseudo-pregnant females; female mice to act as pseudo-pregnant recipients and foster mothers; and transgenic animals, including founder animals and transgenic lines derived from such founders.

The C57BL/6J inbred strain of females are, to date, the most widely used for mating to produce the fertilized eggs. However, injection often can be performed with F2 hybrids generated from matings of F1 hybrid male and female mice (e.g., C57BL/6J, x CBA/J)F1 female x C57BL/6J, x CBA/J) F1 male). F2 hybrid zygotes from F1 hybrids have been successfully employed to produce transgenic mice. These F1 hybrids include but are not limited to C57BL/6J x CBA/J; C57BL/6J x SJL; C3H/HeJ x C57BL/6J; C3H/HeJ x DBA/2J and C57BL/6J x DBA/2J. Those of skill in the art will be aware of other strains of female mice from which fertile embryos could be generated. In certain embodiments, the transgenic mice of the present invention are created using ES cells from a 129sv mouse strain that are grown in 129sv females. These transgenic mice are then back crossed against C57BL/6 strain. In general, the generation of transgenic animals and their subsequent breeding is more efficient if F2 zygoytes are used for microinjection.

A colony for generating transgenic mice also contains fertile studs males. Such males are housed in a separate cages to avoid fighting and injury. These males should be placed in separate cages a few weeks prior to being presented to a superovulated female mouse that will be used for the production fertile eggs. This is necessary because the dominant male will suppress the testosterone and thus sperm production of his littermates. Each superovulated female is placed individually with a stud male.

Sterile males are required for mating to generate pseudo-pregnant recipients and usually are produced by vasectomy. Alternatively genetically sterile studs can be used. Pseudo-pregnant female mice are generated by mating females in natural estrus with vasectomized or genetically sterile males. Pseudo-pregnant females are is competent to receive embryos but do not contain any fertilized eggs. Pseudo-pregnant females are important for making transgenic animals since they serve as the surrogate mothers for embryos that have been injected with DNA or embryonic stem cells. The best pseudo-pregnant recipients are females that have already reared a litter of animals.

Mice that develop from the injected eggs are termed "founder mice". As soon as a founder mouse is identified it is mated to initiate the transgenic line. The potential founder transgenic mice are usually screened for the presence or absence of the injected gene by performing a Southern or dot blot hybridization to DNA extracted from the tail. The protein and RNA expression are analyzed and the transgene copy number and/or level of expression are determined using methods known to those of skill in the art. The protein, RNA expression, and transgene copy numbers are determined in weanling animals (4-5 weeks). When a promoter is used which is constitutively active in animals of weanling age and older, it is not expected that there will be changes in levels of transgenic RNA expression animals beyond weanling age. When a developmentally and/or tissue specific promoter is used, the protein levels are monitored to determine expression levels with age. The transgenic animals also are observed for clinical changes. Examples of neurobehavioral disorders for evaluation are poor mating response, agitation, diminished exploratory behavior in a novel setting, and inactivity may well be important behavioral traits associated with depression. Certain transgenic animal models for AD have been described in e.g., U.S. Pat. No. 5,877,399; U.S. Pat. No. 5,387,742; U.S. Pat. No. 5,811,633

B. Methods of Making Transgenic Animals.

A transgenic animal can be prepared in a number of ways. A transgenic organism is one that has an extra or exogenous fragment of DNA incorporated into its genome, sometimes replacing an endogenous piece of DNA. At least for the purposes of this invention, any animal whose genome has been modified to introduce a mutation in the native APP, as well as its mutant progeny, are considered transgenic animals. In order to achieve stable inheritance of the extra or exogenous DNA, the integration event must occur in a cell type that can give rise to functional germ cells. The two animal cell types that are used for generating transgenic animals are fertilized egg cells and embryonic stem cells. Embryonic stem (ES) cells can be returned from in vitro culture to a. "host" embryo where they become incorporated into the developing animal and can give rise to transgenic cells in all tissues, including germ cells. The ES cells are transfected in culture and then the mutation is transmitted into the germline by injecting the cells into an embryo. The animals carrying mutated germ cells are then bred to produce transgenic offspring. The use of ES cells to make genetic changed in the mouse germline is well recognized. For a reviews of this technology, those of skill in the art are referred to Bronson and Smithies, *J. Biol. Chem.*, 269(44), 27155-27158, (1994); Torres, *Curr. Top. Dev. Biol.*, 36, 99-114; 1998 and the references contained therein.

Generally, blastocysts are isolated from pregnant mice at a given stage in development, for example, the blastocyst from mice may be isolated at day 4 of development (where day 1 is defined as the day of plug), into an appropriate buffer that will sustain the ES cells in an undifferentiated, pluripotent state. ES cell lines may be isolated by a number of methods well known to those of skill in the art. For example, the blastocysts may be allowed to attach to the culture dish and approximately 7 days later, the outgrowing inner cell mass picked, trypsinized and transferred to another culture dish in the same culture media. ES cell colonies appear 2-3 weeks later with between 5-7 individual colonies arising from each explanted inner cell mass. The ES cell lines can then be expanded for further analysis. Alternatively, ES cell lines can be isolated using the immunosurgery technique (described in Martin, *Proc. Natl. Acad. Sci. USA* 78:7634-7638 (1981)) where the trophectoderm cells are destroyed using anti-mouse antibodies prior to explanting the inner cell mass.

In generating transgenic animals, the ES cell lines that have been manipulated by homologous recombination are reintroduced into the embryonic environment by blastocyst injection (as described in Williams et al., *Cell* 52:121-131 (1988)). Briefly, blastocysts are isolated from a pregnant mouse and expanded. The expanded blastocysts are maintained in oil-drop cultures at 4° C. for 10 min prior to culture. The ES cells are prepared by picking individual colonies, which are then incubated in phosphate-buffered saline, 0.5 mM EGTA for 5 min; a single cell suspension is prepared by incubation in a trypsin-EDTA solution containing 1% (v/v) chick serum for a further 5 min at 4° C. Five to twenty ES cells (in Dulbecco's modified Eagle's Medium with 10% (v/v) fetal calf serum and 3,000 units/ml DNAase 1 buffered in 20 mM HEPES [pH 8]) are injected into each blastocyst. The blastocysts are then transferred into pseudo-pregnant recipients and allowed to develop normally. The transgenic mice are identified by coat markers (Hogan et al., Manipulating the Mouse Embryo, Cold Spring Harbor, N.Y. (1986)). Additional methods of isolating and propagating ES cells may be found in, for example, U.S. Pat. No. 5,166,065; U.S. Pat. No. 5,449,620; U.S. Pat. No. 5,453,357; U.S. Pat. No. 5,670,372; U.S. Pat. No. 5,753,506; U.S. Pat. No. 5,985,659, each incorporated herein by reference.

An alternative method involving zygote injection method for making transgenic animals is described in, for example, U.S. Pat. No. 4,736,866, incorporated herein by reference. Additional methods for producing transgenic animals are generally described by Wagner and Hoppe (U.S. Pat. No. 4,873,191; which is incorporated herein by reference), Brinster et al. *Proc. Nat'l Acad. Sci. USA*, 82(13) 4438-4442, 1985; which is incorporated herein by reference in its entirety) and in "Manipulating the Mouse Embryo; A Laboratory Manual" 2nd edition (eds., Hogan, Beddington, Costantimi and Long, Cold Spring Harbor Laboratory Press, 1994; which is incorporated herein by reference in its entirety).

Briefly, this method involves injecting DNA into a fertilized egg, or zygote, and then allowing the egg to develop in a pseudo-pregnant mother. The zygote can be obtained using male and female animals of the same strain or from male and female animals of different strains. The transgenic animal that is born, the founder, is bred to produce more animals with the same DNA insertion. In this method of making transgenic animals, the new DNA typically randomly integrates into the genome by a non-homologous recombination event. One to many thousands of copies of the DNA may integrate at a site in the genome Generally, the DNA is injected into one of the pronuclei, usually the larger male pronucleus. The zygotes are then either transferred the same day, or cultured overnight to form 2-cell embryos and then transferred into the oviducts of pseudo-pregnant females. The animals born are screened for the presence of the desired integrated DNA.

DNA clones for microinjection can be prepared by any means known in the art. For example, DNA clones for microinjection can be cleaved with enzymes appropriate for removing the bacterial plasmid sequences, and the DNA fragments electrophoresed on 1% agarose gels in TBE buffer, using standard techniques. The DNA bands are visualized by staining with ethidium bromide, and the band containing the expression sequences is excised. The excised band is then placed in dialysis bags containing 0.3 M sodium acetate, pH 7.0. DNA is electroeluted into the dialysis bags, extracted with a 1:1 phenol:chloroform solution and precipitated by two volumes of ethanol. The DNA is redissolved in 1 ml of low salt buffer (0.2 M NaCl, 20 mM Tris, pH 7.4, and 1 mM EDTA) and purified on an Elutip-D™ column. The column is first primed with 3 ml of high salt buffer (1 M NaCl, 20 mM Tris, pH 7.4, and 1 mM EDTA) followed by washing with 5 ml of low salt buffer. The DNA solutions are passed through the column three times to bind DNA to the column matrix. After one wash with 3 ml of low salt buffer, the DNA is eluted with 0.4 ml high salt buffer and precipitated by two volumes of ethanol. DNA concentrations are measured by absorption at 260 nm in a UV spectrophotometer. For microinjection, DNA concentrations are adjusted to 3 mg/ml in 5 mM Tris, pH 7.4 and 0.1 mM EDTA.

Additional methods for purification of DNA for microinjection are described in Hogan et al. Manipulating the Mouse Embryo (Cold Spring Harbor Laboratory, Cold Spring Harbor, N.Y., 1986), in Palmiter et al. *Nature* 300:611 (1982); in The Qiagenologist, Application Protocols, 3rd edition, published by Qiagen, Inc., Chatsworth, Calif.; and in Sambrook et al. Molecular Cloning: A Laboratory Manual (Cold Spring Harbor Laboratory, Cold Spring Harbor, N.Y., 1989).

In an exemplary microinjection procedure, female mice six weeks of age are induced to superovulate. The superovulating females are placed with males and allowed to mate. After approximately 21 hours, the mated females are sacrificed and embryos are recovered from excised oviducts and placed in an appropriate buffer, e.g., Dulbecco's phosphate buffered saline with 0.5% bovine serum albumin (BSA; Sigma). Surrounding cumulus cells are removed with hyaluronidase (1 mg/ml). Pronuclear embryos are then washed and placed in Earle's balanced salt solution containing 0.5% BSA in a 37.5° C. incubator with a humidified atmosphere at 5% $CO_2$, 95% air until the time of injection. Embryos can be implanted at the two-cell stage.

Randomly cycling adult female mice are paired with vasectomized males. C57BL/6 or Swiss mice or other comparable strains can be used for this purpose. Recipient females are mated at the same time as donor females. At the time of embryo transfer, the recipient females are anesthetized with an intraperitoneal injection of 0.015 ml of 2.5% avertin per-gram of body weight. The oviducts are exposed by a single midline dorsal incision. An incision is then made through the body wall directly over the oviduct. The ovarian bursa is then torn with watchmakers forceps. Embryos to be transferred are placed in DPBS (Dulbecco's phosphate buffered saline) and in the tip of a transfer pipette (about 10 to 12 embryos). The pipette tip is inserted into the infundibulum and the embryos transferred. After the transfer, the incision is closed by two sutures. The pregnant animals then give birth to the founder animals which are used to establish the transgenic line.

VIII. Pharmaceutical Compositions

The modulators of Hu-Asp, APP processing, and/or β-secretase cleavage identified by the present invention may ultimately be formulated into pharmaceutical compositions i.e., in a form appropriate for in vivo applications. Generally, this will entail preparing compositions that are essentially free of pyrogens, as well as other impurities that could be harmful to humans or animals.

One will generally desire to employ appropriate salts and buffers to render the compositions stable and allow for uptake by target cells. Buffers also will be employed when recombinant cells are introduced into a patient. The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the modulators identified by the present invention, its use in therapeutic compositions is contemplated. Supplementary active ingredients also can be incorporated into the compositions.

The modulator compositions of the present invention include classic pharmaceutical preparations. Administration of these compositions according to the present invention will be via any common route so long as the target tissue is available-via that route. The pharmaceutical compositions may be introduced into the subject by any conventional method, e.g., by intravenous, intradermal, intramusclar, intramammary, intraperitoneal, intrathecal, intraocular, retrobulbar, intrapulmonary (e.g., term release); by oral, sublingual, nasal, anal, vaginal, or transdermal delivery, or by surgical implantation at a particular site, e.g., embedded under the splenic capsule, brain, or in the cornea. The treatment may consist of a single dose or a plurality of doses over a period of time.

The modulator compounds identified using the present invention may be prepared for administration as solutions of free base or pharmacologically acceptable salts in water suitably mixed with a surfactant, such as hydroxypropylcellulose. Dispersions also can be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients also can be incorporated into the compositions.

For oral administration the modulators identified by the present invention may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The compositions of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups also can be derived from inorganic bases such as, for example, sodium, potassium, ammonium, calcium, or ferric hydroxides, and such organic bases as isopropylamine, trimethylamine, histidine, procaine and the like.

The compositions of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups also can be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration.

"Unit dose" is defined as a discrete amount of a therapeutic composition dispersed in a suitable carrier. For example, parenteral administration may be carried out with an initial bolus followed by continuous infusion to maintain therapeutic circulating levels of drug product. Those of ordinary skill in the art will readily optimize effective dosages and administration regimens as determined by good medical practice and the clinical condition of the individual patient. More particularly, the dose should be selected to reduce, inhibit, decrease or otherwise abrogate the formation of Aβ-peptide and more particularly, plaque formation in the brain of a subject exhibiting AD. To this effect, those of skill in the art will be able to employ animal models of AD (e.g., as disclosed in U.S. Pat. No. 5,877,399; U.S. Pat. No. 5,387,742; U.S. Pat. No. 5,811,633) in order to optimize dose administration protocols and predict the relevant amounts of pharmaceutical agents required for intervention of AD in a human subject.

The frequency of dosing will depend on the pharmacokinetic parameters of the agents and the routes of administration. The optimal pharmaceutical formulation will be determined by one of skill in the art depending on the route of administration and the desired dosage. See for example Remington's Pharmaceutical Sciences, 18th Ed. (1990, Mack Publ. Co, Easton Pa. 18042) pp 1435-1712, incorporated herein by reference. Such formulations may influence the physical state, stability, rate of in vivo release and rate of in vivo clearance of the administered agents. Depending on the route of administration, a suitable dose may be calculated according to body weight, body surface areas or organ size. Further refinement of the calculations necessary to determine the appropriate treatment dose is routinely made by those of ordinary skill in the art without undue experimentation, especially in light of the dosage information and assays disclosed herein as well as the pharmacokinetic data observed in animals or human clinical trials.

Appropriate dosages may be ascertained through the use of established assays for determining blood levels in conjunction with relevant dose-response data. The final dosage regimen will be determined by the attending physician, considering factors which modify the action of drugs, e.g., the drug's specific activity, severity of the damage and the responsiveness of the patient, the age, condition, body weight, sex and diet of the patient, the severity of any infection, time of administration and other clinical factors. As studies are conducted, further information will emerge regarding appropriate dosage levels and duration of treatment for specific diseases and conditions.

It will be appreciated that the pharmaceutical compositions and treatment methods of the invention may be useful in fields of human medicine and veterinary medicine. Thus the subject to be treated may be a mammal, preferably human or other animal. For veterinary purposes, subjects include for example, farm animals including cows, sheep, pigs, horses and goats, companion animals such as dogs and cats, exotic and/or zoo animals, laboratory animals including mice rats, rabbits, guinea pigs and hamsters; and poultry such as chickens, turkey, ducks and geese.

EXAMPLES

The following examples present preferred embodiments and techniques, but are not intended to be limiting. Those of skill in the art will, in light of the present disclosure, appreciate that many changes can be made in the specific materials and methods which are disclosed and still obtain a like or similar result without departing from the spirit and scope of the invention.

Example 1

β-Secretase Assays

Activity assays for Asp2(a) may be performed using synthetic peptide substrates of the present invention as follows. Reactions may be are performed in a suitable buffer such as for example, 50 mM 2-[N-morpholino]ethane-sulfonate ("Na-MES," pH 5.5) or 50 mM sodium acetate at a pH range of between 4.0 and 6.0, 70 mM peptide substrate, and recombinant Asp2(a) (1-5 µg protein) for various times at 37° C. An exemplary buffer comprises containing 1% β-octylglucoside. The reaction products are quantified by RP-HPLC using a linear gradient from 0-70 B over 30 minutes (A=0.1% TFA in water, B=0.1% TFA/10% water/90% AcCN). The elution profile is monitored by absorbance at 214 nm.

In such an assay, two product peaks elute before the intact peptide substrate, may be confirmed as the $P_n \ldots P_1$ sequence and the $P_1' \ldots P_n'$ sequence using for example, Edman sequencing or mass spectrometry. Percent hydrolysis of the peptide substrates is calculated by comparing the integrated peak areas for the two product peptides and the starting material derived from the absorbance at 214 nm. The sequence of cleavage/hydrolysis products may be confirmed using Edman sequencing and MADLI-TOF mass spectrometry.

The specificity of the protease cleavage reaction can be determined by performing the β-secretase assay in the presence of 8 µM pepstatin A and the presence of a cocktail of protease inhibitors (e.g., 10 µM leupeptin, 10 µM E64, and 5 mM EDTA). A β-secretase proteolytic activity insensitive to pepstatin (inhibitor of cathepsin D and other aspartyl proteases) or the cocktail (inhibitors of serine proteases, cysteinyl proteases, and metalloproteases, respectively) is indicative of the specificity of the β-secretase activity.

Alternative assays may employ Hu-Asp2(b) expressed in CHO cells and purified using identical conditions for extraction with β-octylglucoside and sequential chromatography over Mono Q® and Mono S®.

An alternative β-secretase assay utilizes internally quenched fluorescent substrates to monitor enzyme activity using fluorescence spectroscopy in a single sample or multiwell format. Each reaction contains for example, 50 mM Na-MES (pH 5.5), a peptide substrate of the present invention (50 µM) and purified Hu-Asp-2 enzyme. These components are equilibrated to 37° C. for various times and the reaction initiated by addition of substrate. Excitation is performed at 330 nm and the reaction kinetics are monitored by measuring the fluorescence emission at 390 nm. To detect compounds that modulate Hu-Asp-2 activity, the test compounds are added during the preincubation phase of the reaction and the kinetics of the reaction monitored as described above. Activators are scored as compounds that increase the rate of appearance of fluorescence while inhibitors decrease the rate of appearance of fluorescence.

In yet another alternative, the Hu-Asp2 β-secretase assay is conducted using a cell based assay system in which cells such as, for example, HEK293 cells expresses a fusion polypeptide comprising a first portion comprising an Hu-Asp2 substrate peptide of the present invention, a second portion comprising a transmembrane domain that anchors the peptide to the Golgi or endoplasmic reticulum of the cell, and a third portion comprising a reporter gene, such as for example, SEA. The transmembrane-domain will act to ensure efficient delivery of the peptide substrate to the cellular environment where it can bind active Hu-Asp2 and be cleaved. The cleavage is detected as a measure of the SEAP activity released into the medium.

Example 2

Method for Peptide Quantitation by Amino Acid Analysis

The present example provides an exemplary method for the quantitition of peptide substrates by amino acid analysis. This method was used to quantify the various substrates of the present invention.

The peptides were quantitated using microwave hydrolyses using CEM Corporation's MDS 2000 microwave oven. Hewlett Packard 300 µl microvials containing approximately 2 µg protein were placed inside a Teflone PFA digestion vessel (CEM Corporation) containing 4 ml of 6 N HCl (Pierce Constant Boiling) with 0.5% (volume to volume) phenol (Mallinckrodt). The samples were then alternately evacuated and flushed with $N_2$ five times. The protein was hydrolyzed using a two-stage process. During the first stage 50% of full power (about 650 W) increased the temperature to 100° C. and held that temperature for 1 minute. Immediately following, 75% power increased the temperature to 150° C. and held that temperature for 25 minutes. After cooling, the samples were dried (Savant SpeedVac). Amino acid analyses were performed on samples derivatized using 6-aminoquinolyl-N-hydroxysuccinimidyl carbamate to yield stable ureas that fluoresce at 395 nm (Waters AccQ•Tag Chemistry Package). The samples were analyzed by reverse phase HPLC on a Hewlett Packard 1100 system and quantification was performed using Hewlett Packard's ChemStation enhanced integrator.

Example 3

Testing an Exemplary Peptide of the Invention Based on the Structure of Ubiquitin/Oxidized Insulin B Chain The present Example describes the production of an exemplary Hu-Asp2 substrate of the present invention and use in an Hu-Asp2 assay of the invention.

The substrate KVEANY-EVEGERKK (SEQ ID NO:5) was synthesized using by solid-phase technology employing a Model 433A from Applied Biosystems Inc. The purity of this substrate was assessed by HPLC analysis. Briefly, crude peptide was dissolved in dilute acetic acid, filtered and loaded on preparative reverse phase column (Vydac C-19, 22×250 mm, 10 micron) at 4 ml/minute 100% A (A:0.1% TFA in water, B:0.07% TFA in acetonitrile). Gradient used was 0→10% B, 10 minutes then 10->50% B, 200 minutes. The column effluent was monitored by absorbance at 220 nm and 280 nm. Fractions were monitored on an analytical reverse phase system (Vydac C18, 4.6×250 mm, 5 micron). Solvents and wavelengths as above. The linear gradient for this RP-HPLC was from 0-70% B in 20 minutes at 1.0 ml/min.

The chemical authenticity of the peptide was determined using mass spectrometry analysis. More particularly, the chemical authenticity of each peptide was established by mass spectrometry employing a Micromass Platform II mass spectrometer equipped with a Hewlett Packard Series 1050 HPLC system. The identify of the peptide was confirmed by injecting 5 µl of sample into the flow of 100 µl/min of 1:1=methanol:water. The mass spectrometer was operating in electrospray ionization mode with needle voltage 3 KV, temperature 120° C. and cone voltage 30 V.

The above-described peptide was tested as a substrate for Hu-Asp2 activity in a reaction comprising 200 mM sodium acetate, pH4.5, 200 µM substrate, 200 nM Hu-Asp2 enzyme at 37° C. The reaction mixture was allowed to proceed for between 1 and 3 hours. The reaction products were monitored as described in Example 1 and it was found that KVEANY-EVEGERKK (SEQ ID NO:5) was a good substrate for Hu-Asp.

The KVEANY-EVEGERKK (SEQ ID NO:5) peptide was further modified by the insertion of a cys residue was inserted between R and KK to give the peptide KVEANY-EVEGER-CKK (SEQ ID NO:6). This peptide was N-terminally biotinylated, and made fluorescent by the covalent attachment of oregon green at the Cys residue. Briefly, for biotinylation, resin-bound peptide was suspended in (approx. 10 ml) dimethylformamide containing diisopropylethylamine (0.15 ml) and reacted with 50 mg EZ-link NHS-LC-biotin (Pierce) at room temperature. The reaction was allowed to proceed for 24 hours (or until ninhydrin negative). The biotinylated peptide was then cleaved in 10 ml trifuluoroacetic acid containing ethyl methyl sulfide:anisole:1,2-ethanedithiol (1:3:1; total 5%) for 2 hours at room temperature. The cleavage solution was filtered through a sintered glass funnel and evaporated to near dryness under reduced pressure. The crude peptide was precipitated from the cleavage solution with cold diethyl ether. The precipitated peptide was collected on a sintered glass funnel, washed with diethyl ether, dissolved in dilute acetic and evaporated to dryness under reduced pressure. The residue was dissolved in glacial acetic acid and lyophilized.

The purified biotinylated peptide was dissolved in approximately 5 ml (0.1N) $NaH_2PO_4$ (pH 8.0) that had been previously degassed. 5 mg of Oregon Green 488 maleimide (Molecular Probes) dissolved in 0.5 ml dimethylformamide was then added and the mixture stirred in the dark for 30 minutes at room temperature. Following the reaction, unreacted reagent was quenched by addition of 15 mg of L-cysteine for an additional 30 minutes. The final mixture was then filtered through a sintered glass funnel, acidified by addition of glacial acetic acid, and purified by preparative reverse phase HPLC as described above except the initial elution conditions (100% A) were held constant until the break-through DMF peak eluted.

The resulting compound, Biotin-KVEANY-EVEGERC (oregon green)KK, was tested as a substrate for Hu-Asp2 activity using the following conditions: 200 mM sodium acetate, pH 4.5, 10 µM substrate, 50 nM enzyme at 37° C. The reaction was allowed to proceed for 2 hrs and samples withdrawn at several times. The results showed that 20%, 37%, 57%, and 82% cleavage occurred after 15, 30, 60, and 120 minutes, respectively. Do they have comparative #'s for Nature or APP-SW?

Mass spectrometry analysis showed that cleavage had occurred between Tyr and Glu only. This new biotinylated fluorescent peptide had $V_{max}$ and $K_m$ that were at least twice better than a previous biotinylated fluorescent substrate derived from the Swedish Mutant peptide: SEVNL-DAEFR (SEQ ID NO:19).

Example 4

APP Constructs Containing Mutated β-Secretase Cleavage Site

This example describes a method for creating mutations of APP using recombinant methods, to introduce sequences of synthetic Asp2 substrates of the invention.

A mammalian cell expression bicistronic construct named 125, which contains a Swedish mutant APP695 and extra dilysine residues at the C-terminus, was used as a starting material to generate novel APP mutants containing sequences of the invention. The sequences encoding VNLDA at residues 593 to 597 of this APP695 were replaced with VSYEA (SEQ ID NO:189), ISY-EV (SEQ ID NO:179) or VSYEV (SEQ ID NO:177) using site directed mutagenesis.

The site-directed mutagenesis was performed with a commercial kit (QUICKCHANGE, site-directed mutagenesis, Strategene, La Jolla, Calif.) using the following primers:

```
#ISYEV5
5'-GAG ATC TCT GAA ATT AGT TAT GAA (SEQ ID NO: 171)

GTA GAA TTC CGA CAT GAC TCA GG-3'

#ISYEV3
5'-TGA GTC ATG TCG GAA TTC TAC TTC (SEQ ID NO: 172)
```

```
                          -continued
ATA ACT AAT TTC AGA GAT CTC CTC-3'

#VSYEV5
5'-GAG ATC TCT GAA AGT AGT TAT GAA       (SEQ ID NO: 173)

GTA GAA TTC CGA CAT GAC TCA GG-3'

#VSYEV3
5'-TGA GTC ATG TCG GAA TTC TAC TTC       (SEQ ID NO: 174)

ATA ACT ACT TTC AGA GAT CTC CTC-3'

#VSYEA5
5'-GAG ATC TCT GAA ATT AGT TAT GAA       (SEQ ID NO: 175)

GCA GAA TTC CGA CAT GAC TCA GG-3'

#VSYEA3
5'-TGA GTC ATG TCG GAA TTC TGC TTC       (SEQ ID NO: 176)

ATA ACT AAT TTC AGA GAT CTC CTC-3'
```

The PCR conditions for performing the site-directed mutagenesis were as follows: denaturing at 95° C. for 1 min., annealing at 56° C. for 30 sec and amplifying at 68° C. for 16 min. The reaction was performed in 50 µl of reaction solution which contained 150 ng each of primer, 50 ng of template DNA, 2.5 u of pfu Turbo DNA polymerase and 200 µM of dNTP. The amplified products were digested with restriction enzyme Dpn I for 60 minutes followed by transformation. Mini-preps of plasmid DNA were prepared and DNA sequencing was performed to identify mutated clones containing the desired modified sequences.

EXAMPLE 5

Figure 3:
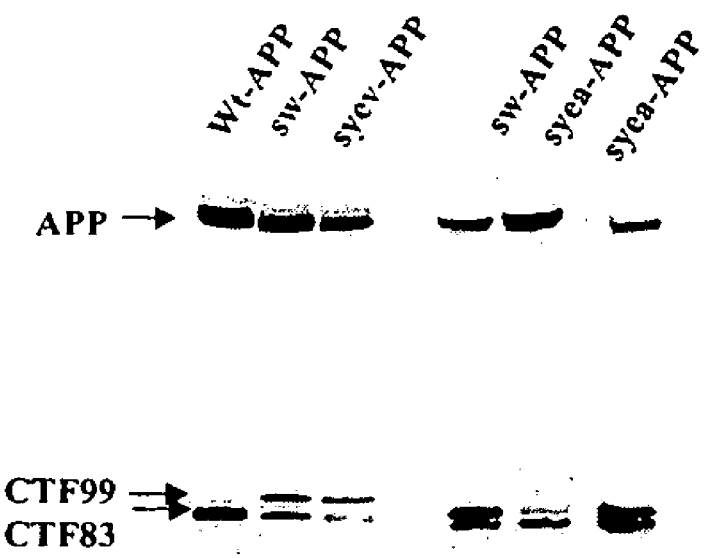
FIG. 3 contains images depicting Western blot analysis of APP processing by β-secretase. A stable HEK-293 cell line that expresses higher levels of Asp2 was transfected with either wt-APP or different mutant APP DNA constructs. After transfection for 48 hours, cell extracts were analyzed by Western analysis. The antibody C8 which recognizes the C-terminus of human APP was used for detecting full-length APP and its processing products. The β-secretase activity was judges by the production of CTF99 or the ratio of CTF99 over CTF83.

Cell-Based Testing of Peptide Sequences of the Invention Designed into Wild-type APP Sequence The inventors modified APP expression constructs with the mutation KM-DA$_{594-597}$ (SEQ ID NO:139) to SYEV$_{594-597}$ (SEQ ID NO:140) or SYEA$_{594-597}$ (SEQ ID NO:187) as described in the preceding example 4 to test whether these mutations would allow an efficient proteolytic processing of the resulting modified (mutant) APP by β-secretase in cells. The resultant expression constructs contained a CMV promoter to drive expression of a wildtype APP695 sequence modified to include a C-terminal dilysine, and further modified with the specific mutations described above. Since APP variants were subcloned into a pIRES-EGFP vector Clonetech, Palo Alto, Calif.), the efficiency of expression can be monitored by the presence of green fluorescent signal. After HEK 293 derivative cells that express higher levels of Hu-Asp2 were transfected with different APP variants for 48 hours, the cell extracts were prepared and analyzed by Western blots transferred from a 4-12% SDS-PAGE gel. The Hu-Asp2 activity can be monitored by observing the increase of the β-secretase cleavage product CTF-99 that is recognized by a specific antibody C8. As shown in FIG. 3, both mutant APP variants were proficiently cleaved by Asp2. Similar to the in vitro enzymatic assay, APP with SYEV$_{594-597}$ (SEQ ID NO:140) was cleaved more efficiently than APP with SYEA$_{594-597}$ (SEQ ID NO:187).

As one indicator of APP processing, levels of secreted Aβ from the medium of the transfected HEK-293 cells were measured. Measurements were by ELISA using antibody 6E10 (Syntek, St. Louis, Mo.) to capture Aβ and antibody 208 for Aβ40 and antibody 165 for Ap42. Both 208 208 and 165 were purchased from Research Foundation of Mental Hygiene (Staten Island, N.Y.), and it was independently determined that the mutation of D$_{596}$A$_{597}$ to either E$_{596}$A$_{597}$ or E$_{596}$V$_{597}$ (which affects the N-terminus of Aβ) did not affect ELISA detection of Aβ peptides. Increased production of secreted Aβ$_{40}$ and Aβ$_{42}$ was observed with cells transfected with these two mutated forms of APP. Using additional constructs in peptide activity assays, it was determined that if an Asn residue was substituted in place of a Ser to give SEVNY-↓-EVEFR (SEQ ID NO:170), this peptide has an activity that is only ⅕ than that of SEVSY-↓-EVEFR (SEQ ID NO:141; Table 4). This observation reaffirms that amino acid optimization at a certain position depends on the rest of the substrate sequence.

Additional cells useful for such assays include

In summary, SEVSY-↓-EVEFR (SEQ ID NO:141) is an excellent APP-modified substrate for Asp2 that gives easily measurable levels of Aβ in cell-based assays.

Example 6

Cell Lines Expressing Mutant APP Forms

The preceding describes assays that employed a transformed HEK-293 cell line. Other useful cell lines include, but not limited to, human HeLa, IMR-32, SK-N-MC, SHY-5Y cells, Chinese Hamster Ovary cells, mouse Neuro-2a cell, and rat PC12 cells. All of these cells are readily available from ATCC. In preferred embodiments, the vector used to introduce the modified APP form also includes an antibiotic resistance gene, e.g., so that the stable cell lines can be selected under G418 resistance conditions. In another preferred embodiment, cell lines are generated that express both mutant APP as described herein and that also recombinantly express Asp2. In one variation, the Asp2 is introduced using a second construct that permits selection under a separate selective antibiotic (e.g., hygromysin selection). Such cell lines are considered especially well suited for high throughput screening for modulators of Asp2-mediated APP processing.

Example 7

High Throughput Cell-Based Assay for Asp2 Modulators

Assays such as those described in Example 5 are most useful when they can be conducted quickly, with automation, and with the screening of several samples in parallel. The general procedure described hereafter is applicable for a variety of cell lines including those identified above. Preferably, the cell-based assay is conducted in 96-well format and each candidate compound is measured in duplicates.

About 25,000 cells will be plated onto each well the day before the treatment and grown in normal cell culture conditions (37° C., 5% CO$_2$).

An appropriate concentration of compound stock is prepared in DMSO. The idea stock solution is about 1,000 times the highest concentration to be tested. On the microplate, compounds are serially diluted 1:3 with DMSO (25 µl+200 µl DMSO), and then diluted in media at a ratio 1:5 v/v compound:media (50 µl+200 µl media) to yield an intermediate plate used for further dilutions. The intermediate plate is diluted 1:20 (13 µl+247 µl media) to yield concentrations that are ten times the final desired concentrations in duplicate.

To begin the assays, 20 µl of final compound dilution is added to cell plates that contain 180 µl of media, and the plate is put back to the tissue culture incubator for continuing culture. After three hours of incubation, media is collected and the cells are again treated with 180 µl of media plus 20 µl of compound, and then cultured overnight. Media from the cells is collected the next day and assayed to measure evidence of APP processing. For example, Aβ levels are measured from the collected media by ELISA. N-terminal fragments resulting from APP processing also can be measured.

Example 8

Chimeric Protein Comprising MBP and APP and Asp2 Recognition Sequences of the Invention A fusion protein comprising a maltose binding protein (SEQ ID NO:194) with 125 amino acids from APP C-terminus was produced by synthesizing an expression of MBPC125 construct and transforming the construct into an *E. coli* host. The MBP (NEB, Beverley, Mass.) provides a useful detection substrate for detecting cleavage following Asp2 cleavage of substrates of the invention.

Fusions of APP and maltose-binding protein (MBP) are produced essentially as described in U.S. Pat. No. 5,744,346 and U.S. Pat. No. 5,942,400, (except that β-secretase substrates of the invention are included in the fusion protein). These documents also describe assays, which are run by exposing the fusion polypeptide to β-secretase which cleaves the 125 amino acid portion of APP at the amino-terminus of the βA. The MBP portion may then be captured, and the carboxy-terminus of the APP fragment which is exposed by cleavage with β-secretase may be identified with 192 antibody specific for said terminus. In the present invention, the APP employed in these assays will comprise the peptides of the present invention at the β-secretase cleavage site.

The approach for mutating the β-secretase cleavage site of normal APP (VKM-DA, SEQ ID NO:180) to VSY-EV (SEQ ID NO:177), VSY-DA (SEQ ID NO:178) or ISY-EV (SEQ ID NO:179) is described in a preceding example.

In a related procedure, the MBPC125 construct containing MBPC125-VSYEV was further modified by introducing a stop codon after residues VSY, which corresponds with position $P_3P_2P_1$. This construct permits one to produce a truncated version of MBPC125 fusion protein that ends at ---- VSY. This truncated protein is useful to set up a standard assay curve for measuring Asp2 cleavage products of the MPBC125 proteins because it corresponds to the expected cleavage product. The following pair of primers can be used for the mutagenesis.

```
#VSYEND5
5'-GAC ATC TCT GAA GTG AGT TAT TAG  (SEQ ID NO: 181)
GCA GAA TTC CGA CAT GAC TCA GG-3

#VSYEND3
5'-TGA GTC ATG TCG GAA TTC TGC CTA  (SEQ ID NO: 182)
ATA ACT CAC TTC AGA GAT CTC CTC-3'
```

PCR procedures as described in a preceding example can be used to introduce the mutation.

Example 9

Creation of Exemplary Fusion Protein Comprising SEAP, Insulin B Chain, and Asp2 Recognition Sequences of the Invention The present Example describes a fusion protein in which secreted alkaline phosphatase (SEAP) is fused to either partial or full-length insulin B chain with modified optimal Asp2 cleavage site and the transmembrane domain of Hu-Asp2 (residue 454-477) together with a short C-terminal Flag-tagged tail. The sequence of such peptide/construct depicted in FIG. 1.

When the fusion protein is recombinantly co-expressed with Hu-Asp2 in a cell line or expressed in a cell line with endogenous Hu-Asp2 activity, Hu-Asp2 will cleave the fusion protein to release SEAP into the cell medium. Thus, the protease activity may be monitored based on the SEAP activity in the medium.

Generation of the Fusion Proteins:

To make a fusion protein with secreted alkaline phosphatase as a reporter, the pCMV/SEAP vector DNA from Topix (Bedford, Mass.) was used. The stop codon TTA of the SEAP coding region was then mutated to an EcoRI site GAATTC by site directed mutagenesis. The mutated plasmid was then digested with EcoRI completely and treated with calf intestine alkaline phosphatase to dephosphorylate the vector DNA. This treated vector DNA was used for the subsequent insertion of DNA fragments covering the components 2 to 4 in Table 4 below.

A single chain cDNA fragment encoding human insulin β-chain was synthesized and the double strand DNA was produced by PCR amplification using this chain as a template. The 5'-primer contains an overhang of EcoRI cleavage site. The 3'-primer contains a Bgl II site. The transmembrane domain of human Asp2 was also produced by PCR amplification with 3'-primer overhanged with a flag-tag coding sequences and an EcoRI cloning site and 5'-primer with a Bgl II site. The two DNA fragments were digested with restriction enzymes EcoRI and BglII and subsequently ligated into the above vector DNA. Various peptides of the present invention spanning the β-secretase cleavage site were generated by site-directed mutagenesis.

TABLE 7

| Component 1 (reporter) | Component 2 (cleavage site) | Component 3 (membrane target sequence) | Component 4 (cytosol tail) |
|---|---|---|---|
| SEAP Sequence (residue 1-506) | VEANY-EVEGE (SEQ ID NO: 184) | Asp2 transmembrane | flag tag sequence |
| luciferase (full | VEANY-AVEGE | APP residue | DYKDDDDK |

TABLE 7-continued

| Component 1 (reporter) | Component 2 (cleavage site) | Component 3 (membrane target sequence) | Component 4 (cytosol tail) |
|---|---|---|---|
| length) | (SEQ ID NO: 185) | 598-661 | (SEQ ID NO: 186) |
| CAT (full length) | | | APP residue 662-695 |
| β-galactosidase (full length) | | galactosyltransferase (residue 4-27) | |
| | | Asp1 transmembrane domain (residue 470-492) | |
| | | sialytransferase (residue 10-33) | |
| | | syntaxin 6 (residue 261-298) | |
| | | acetyl glucosaminyl transferase (residue 7-29) | |

Another type of fusion protein contemplated employs the C-terminal region of APP. A PCR product corresponding to the C-terminal 97 amino acids of APP (residue 598-695) is generated. There is a natural EcoRI site at the residue 598 and an EcoRI site may be included at the 3'-primer. The PCR product is digested with EcoRI and then inserted into the SEAP vector. DNA sequences coding the various Hu-Asp2 peptide substrates described in the present invention are inserted into the β-secretase cleavage region of the APP by the site directed mutagenesis approach.

Example 10

Generation of Constructs for Producing Mutant APP Transgenic Mice.

As described above, transgenic animals comprising the synthetic beta secretase recognition sequences of the present invention comprise useful animal models for disease states. For example, these animals will be useful models for Alzheimer's Disease. This example describes a suitable construct for introducing such sequences into mice.

Materials and methods for creating transgenic mice are now well known and have been described in the literature, and are easily adapted to make transgenic mice of the invention. For example, U.S. Pat. No. 5,877,399 (incorporated herein by reference) describes transgenic mice that express an APP Swedish mutation. Additional transgenic mice are described in U.S. Pat. No. 5,387,742. It is contemplated that techniques similar to those described in the aforementioned patents may be used in conjunction with the teachings of the present invention to yield mouse models. Specifically, the constructs for producing the transgenic mice in the present invention will comprise an APP that has been mutated (preferably at or near the codons for its natural β-secretase recognition sequence) to include sequence encoding one of the peptides of the present invention.

In specific exemplary transgenic mice the mutant APP will have a replacement of the four amino acids surrounding the β-secretase cleavage site in APP, i.e. . . . KM-↓-DA . . . (SEQ ID NO:139), with . . . SY-↓-EV . . . (SEQ ID NO:140). In other specific embodiments, it is contemplated that the mutant APP (e.g., mutant of human APP695) will comprise any of the peptides of the present invention with a C-terminal dilysine addition. A preferred construct is a mutant human APP695 with a C-terminal dilysine addition and with the SYEV beta secretase recognition sequence of the invention.

A commercially available murine prion (PrP) protein vector from Life Tech was selected for experimentation. The vector was digested with Xho I and blunt-ended. Attr sequence was blunt cloned into the Xho I site of PrP vector and orientation selected by sequence analysis.

The beta secretase substrate selected for introduction into the mouse comprised human APP695 with a C-terminal dilysine addition and with the SYEV beta secretase recognition sequence of the invention (APP-kk-syev, SEQ ID NO:183). This modified APP sequence was cloned into pDONR201 and the recombination reaction inserted the APP-kk-syev sequence into the PrP vector downstream of the mouse prion promoter and upstream of mouse PRP 3' flanking sequence.

Using homologous recombination techniques known in the art and/or described above, this construct can be used to introduce the modified APP sequence into murine embryonic stem cells, and the cells can be used to generate transgenic mice harboring an APP containing the artificial beta secretase substrate sequences of the present invention.

It will be clear that the invention may be practiced otherwise than as particularly described in the foregoing description and examples.

Numerous modifications and variations of the present invention are possible in light of the above teachings and, therefore, are within the scope of the invention. The entire disclosure of all publications cited herein are hereby incorporated by reference.

What is claimed is:

1. A method for assaying for modulators of β-secretase activity, comprising:
   (a) contacting a polypeptide with β-secretase APP processing activity with a substrate, both in the presence and in the absence of a putative modulator compound;
   wherein said substrate comprises a peptide having an amino acid sequence of at least 6 amino acids, said amino acid sequence including four amino acids defined by formula $P_2P_1$-$P_{1'}P_{2'}$, wherein:
   $P_2$ is N;
   $P_1$ comprises an amino acid selected from the group consisting of Y, L and F;
   $P_{1'}$ is E;
   $P_{2'}$ is V;
   wherein the substrate is cleaved between $P_1$ and $P_{1'}$ by a human aspartyl protease encoded by the nucleic acid sequence of SEQ ID NO: 1 or SEQ ID NO: 3 (Hu-Asp2); and
   wherein said peptide does not comprise the corresponding $P_2P_1$-$P_{1'}P_{2'}$ portion of amino acid sequence depicted in SEQ ID NO: 19, SEQ ID NO: 20, SEQ ID NO: 21, SEQ ID NO: 26, SEQ ID NO: 27, SEQ ID NO: 28, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, or SEQ ID NO: 39;
   (b) measuring cleavage of the substrate peptide in the presence and in the absence of the putative modulator compound; and
   (c) identifying modulators of β-secretase activity from a difference in substrate cleavage in the presence versus in the absence of the putative modulator compound, wherein a modulator that is a β-secretase antagonist reduces such cleavage and a modulator that is a β-secretase agonist increases such cleavage.

2. The method of claim 1,
   wherein said substrate comprises a peptide having an amino, acid sequence of at least 6 amino acids, said amino acid sequence including five amino acids defined by formula $P_2P_1$-$P_{1'}P_{2'}P_{3'}$ and
   wherein $P_{3'}$ comprises an amino acid selected from the group consisting of E, G, F, H, cysteic acid and S.

3. The method of claim 2, wherein $P_{3'}$ is E.

4. The method of claim 2, wherein the peptide comprises a sequence of amino acids defined by the formula $P_3P_2P_1$-$P_{1'}P_{2'}P_{3'}$, wherein $P_3$ is an amino acid selected from the group consisting of A, V, I, S, H, Y, T and F.

5. The method of claim 4, wherein $P_3$ comprises an amino acid selected from the group consisting of I or V.

6. The method of claim 4, wherein the peptide comprises a sequence of amino acids defined by the formula $P_4P_3P_2P_1$-$P_{1'}P_{2'}P_{3'}$, wherein $P_4$ is an amino acid selected from the group consisting of E, G, I, D, T, cysteic acid and S.

7. The method of claim 6, wherein the peptide comprises a sequence of amino acids defined by the formula $P_4P_3P_2P_1$-$P_{1'}P_{2'}P_{3'}P_{4'}$, wherein $P_{4'}$ is an amino acid selected from the group consisting of F, W, G, A, H, P, G, N, S, and E.

8. The method of claim 1, wherein the amino acids at positions $P_2$, $P_1$, $P_{1'}$, $P_{2'}$ comprise N, F, E and V, respectively.

9. The method for assaying for modulators of β-secretase activity, comprising:
   (a) contacting a polypeptide with β-secretase APP processing activity with a substrate, both in the presence and in the absence of a putative modulator compound;
   wherein said substrate comprises amyloid precursor protein (APP) amino acid sequence with a modified β-secretase processing site defined by said formula $P_2P_1$-$P_{1'}P_{2'}$, wherein:
   $P_2$ is N;
   $P_1$ comprises an amino acid selected from the group consisting of Y, L and F;
   $P_{1'}$ is E;
   $P_{2'}$ is V;
   wherein the substrate is cleaved between $P_1$ and $P_{1'}$ by a human aspartyl protease encoded by the nucleic acid sequence of SEQ ID NO: 1 or SEQ ID NO: 3 (Hu-Asp2); and
   wherein said peptide does not comprise the corresponding $P_2P_1$-$P_{1'}P_{2'}$ portion of amino acid sequence depicted in SEQ ID NO: 19, SEQ ID NO: 20, SEQ ID NO: 21, SEQ ID NO: 26, SEQ ID NO: 27, SEQ ID NO: 28, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, or SEQ ID NO: 39;
   (b) measuring cleavage of the substrate peptide in the presence and in the absence of the putative modulator compound; and
   (c) identifying modulators of β-secretase activity from a difference in substrate cleavage in the presence versus in the absence of the putative modulator compound, wherein a modulator that is a β-secretase antagonist reduces such cleavage and a modulator that is a β-secretase agonist increases such cleavage.

10. The method of any one of claim 1-2, 3 or 4-8 wherein said peptide comprises an amino acid sequence having up to 50 amino acids.

11. The method of any one of claim 1-2, 3 or 4-8 wherein the peptide further comprises a first label.

12. The method of claim 11 wherein the peptide further comprises a second label.

13. The method of any one of claim 1-2, 3 or 4-8 wherein the peptide further comprises a detectable label and a quenching moiety, wherein cleavage of the peptide between $P_1$ and $P_{1'}$ separates the quenching moiety from the label to permit detection of the label.

14. The method of claim 2, wherein said cysteic acid comprises a covalently attached label.

15. The method of any one of claim 1-2, 3 or 4-8 wherein the rate of cleavage of said peptide by said human aspartyl protease is greater than the rate of cleavage of a polypeptide comprising the human APP β-secretase cleavage sequence: SEVKMDAEFR (SEQ ID NO: 20).

16. The method of any one of claim 1-2, 3 or 4-8 wherein the rate of cleavage of said peptide by said human aspartyl protease is greater than the rate of cleavage of a polypeptide comprising the human APP Swedish KM→NL mutation, β-secretase cleavage sequence SEVNLDAEFR (SEQ ID NO: 19).

17. The method of any one of claim 1-2, 3 4-8 or 9 wherein the polypeptide with β-secretase APP processing activity comprises an amino acid sequence selected from the group consisting of
  (a) the amino acid sequence of SEQ ID NO: 2,
  (b) a fragment of the amino acid sequence of SEQ ID NO: 2 that retains β-secretase APP processing activity, wherein said fragment includes the aspartyl protease active site tripeptides DTG and DSG,
  (c) an amino acid sequence that is at least 95% identical to (a) or (b), wherein the polypeptide includes the aspartyl protease active site tripeptides DTG and DSG and exhibits β-secretase APP processing activity;
  (d) the amino acid sequence SEQ ID NO: 4,
  (e) a fragment of the amino acid sequence of SEQ ID NO: 4 that retains β-secretase APP processing activity, wherein said fragment includes the aspartyl protease active site tripeptides DTG and DSG, and
  (f) an amino acid sequence that is at least 95% identical to (d) or (e), wherein said fragment includes the aspartyl protease active site tripeptides DTG and DSG and exhibits β-secretase APP processing activity.

18. The method of any one of claims 1-2, 3 8 or 9 wherein the polypeptide with β-secretase APP processing activity comprises an amino acid sequence selected from the group consisting of
  (a) the amino acid sequence of SEQ ID NO: 2; and
  (b) a fragment of the amino acid sequence of SEQ ID NO: 2 that retains β-secretase APP processing activity, wherein said fragment includes the aspartyl protease active site tripeptides DTG and DSG.

19. A method according to claim 18, wherein the polypeptide with β-secretase APP processing activity comprises a polypeptide purified and isolated from a cell transformed or transfected with a polynucleotide comprising a nucleotide sequence that encodes the polypeptide.

20. A method according to claim 10,
  wherein the substrate is expressed in a cell transformed or transfected with a polynucleotide comprising a nucleotide sequence that encodes the substrate,
  wherein the cell expresses the polypeptide with β-secretase APP processing activity;
  wherein the contacting comprises growing the cell in the presence and absence of the test agent, and
  wherein the measuring step comprises measuring APP processing activity of the cell.

21. A method according to claim 20, wherein the contacting comprises administering the test agent to a transgenic non-human mammal that comprises the cell.

22. A method according to claim 1, wherein the polypeptide is encoded by a polynucleotide comprising the nucleotide sequence selected from the group consisting of:
  (a) the nucleotide sequence of SEQ ID NO: 1 or SEQ ID NO; 3,
  (b) a nucleotide sequence that hybridizes under the following stringent hybridization conditions to the complement of SEQ ID NO: 1 or 3:
    (1) hybridization at 42° C. in a hybridization buffer comprising 6×SSC and 0.1% SDS, and
    (2) washing at 65° C. in a wash solution comprising 1×SSC and 0. 1% SDS;
  wherein said nucleotide sequence encodes a polypeptide that exhibits β-secretase APP processing activity.

23. A method according to claim 1, wherein the substrate comprises a peptide having an amino acid sequence selected from the group consisting of SEQ ID NO: 133, SEQ ID NO: 134 and SEQ ID NO: 5.

24. The method of claim 4, wherein the peptide comprises a sequence of amino acids defined by the formula $P_3P_2P_1$-$P_{1'}P_{2'}P_{3'}$, wherein $P_3$ is V, $P_2$ is N, $P_1$ is F, $P_{1'}$ is E, $P_{2'}$ is V and $P_{3'}$ is E.

* * * * *

SEQUENCE LISTING

<160> NUMBER OF SEQ ID NOS: 199

<210> SEQ ID NO 1
<211> LENGTH: 2070
<212> TYPE: DNA
<213> ORGANISM: Homo sapiens

<400> SEQUENCE: 1

| | | | | | |
|---|---|---|---|---|---:|
| atggcccaag | ccctgccctg | gctcctgctg | tggatgggcg | cgggagtgct | gcctgcccac | 60 |
| ggcacccagc | acggcatccg | gctgccctg | cgcagcggcc | tggggggcgc | ccccctgggg | 120 |
| ctgcggctgc | cccgggagac | cgacgaagag | cccgaggagc | ccggccggag | gggcagcttt | 180 |
| gtggagatgg | tggacaacct | gaggggcaag | tcggggcagg | gctactacgt | ggagatgacc | 240 |
| gtgggcagcc | cccgcagac | gctcaacatc | ctggtggata | caggcagcag | taactttgca | 300 |
| gtgggtgctg | ccccccaccc | cttcctgcat | cgctactacc | agaggcagct | gtccagcaca | 360 |
| taccgggacc | tccggaaggg | tgtgtatgtg | ccctacaccc | agggcaagtg | ggaaggggag | 420 |
| ctgggcaccg | acctggtaag | catccccat | ggccccaacg | tcactgtgcg | tgccaacatt | 480 |
| gctgccatca | ctgaatcaga | caagttcttc | atcaacggct | ccaactggga | aggcatcctg | 540 |
| gggctggcct | atgctgagat | tgccaggcct | gacgactccc | tggagccttt | ctttgactct | 600 |
| ctggtaaagc | agacccacgt | tcccaacctc | ttctccctgc | acctttgtgg | tgctggcttc | 660 |
| cccctcaacc | agtctgaagt | gctggcctct | gtcggaggga | gcatgatcat | tggaggtatc | 720 |
| gaccactcgc | tgtacacagg | cagtctctgg | tatacaccca | tccggcggga | gtggtattat | 780 |
| gaggtcatca | ttgtgcgggt | ggagatcaat | ggacaggatc | tgaaaatgga | ctgcaaggag | 840 |
| tacaactatg | acaagagcat | tgtggacagt | ggcaccacca | accttcgttt | gcccaagaaa | 900 |
| gtgtttgaag | ctgcagtcaa | atccatcaag | gcagcctcct | ccacggagaa | gttccctgat | 960 |
| ggtttctggc | taggagagca | gctggtgtgc | tggcaagcag | gcaccacccc | ttggaacatt | 1020 |
| ttcccagtca | tctcactcta | cctaatgggt | gaggttacca | accagtcctt | ccgcatcacc | 1080 |
| atccttccgc | agcaatacct | gcggccagtg | aagatgtgg | ccacgtccca | agacgactgt | 1140 |
| tacaagtttg | ccatctcaca | gtcatccacg | ggcactgtta | tgggagctgt | tatcatggag | 1200 |
| ggcttctacg | ttgtctttga | tcgggcccga | aaacgaattg | gctttgctgt | cagcgcttgc | 1260 |
| catgtgcacg | atgagttcag | gacggcagcg | gtggaaggcc | cttttgtcac | cttggacatg | 1320 |
| gaagactgtg | gctacaacat | tccacagaca | gatgagtcaa | ccctcatgac | catagcctat | 1380 |
| gtcatggctg | ccatctgcgc | cctcttcatg | ctgccactct | gcctcatggt | gtgtcagtgg | 1440 |
| cgctgcctcc | gctgcctgcg | ccagcagcat | gatgactttg | ctgatgacat | ctccctgctg | 1500 |
| aagtgaggag | gcccatgggc | agaagataga | gattcccctg | gaccacacct | ccgtggttca | 1560 |
| ctttggtcac | aagtaggaga | cacagatggc | acctgtggcc | agagcacctc | aggaccctcc | 1620 |
| ccacccacca | aatgcctctg | ccttgatgga | gaaggaaaag | gctggcaagg | tgggttccag | 1680 |
| ggactgtacc | tgtaggaaac | agaaaagaga | gaaagaagc | actctgctgg | cgggaatact | 1740 |
| cttggtcacc | tcaaatttaa | gtcgggaaat | tctgctgctt | gaaacttcag | ccctgaacct | 1800 |
| ttgtccacca | ttcctttaaa | ttctccaacc | caaagtattc | ttcttttctt | agtttcagaa | 1860 |
| gtactggcat | cacacgcagg | ttaccttggc | gtgtgtccct | gtggtaccct | ggcagagaag | 1920 |
| agaccaagct | tgtttccctg | ctggccaaag | tcagtaggag | aggatgcaca | gtttgctatt | 1980 |
| tgctttagag | acagggactg | tataaacaag | cctaacattg | gtgcaaagat | tgcctcttga | 2040 | attaaaaaaa aaaaaaaaaa aaaaaaaaaa                                              2070

<210> SEQ ID NO 2
<211> LENGTH: 501
<212> TYPE: PRT
<213> ORGANISM: Homo sapiens

<400> SEQUENCE: 2

Met Ala Gln Ala Leu Pro Trp Leu Leu Leu Trp Met Gly Ala Gly Val
 1               5                  10                  15

Leu Pro Ala His Gly Thr Gln His Gly Ile Arg Leu Pro Leu Arg Ser
             20                  25                  30

Gly Leu Gly Gly Ala Pro Leu Gly Leu Arg Leu Pro Arg Glu Thr Asp
         35                  40                  45

Glu Glu Pro Glu Glu Pro Gly Arg Arg Gly Ser Phe Val Glu Met Val
     50                  55                  60

Asp Asn Leu Arg Gly Lys Ser Gly Gln Gly Tyr Tyr Val Glu Met Thr
 65                  70                  75                  80

Val Gly Ser Pro Pro Gln Thr Leu Asn Ile Leu Val Asp Thr Gly Ser
                 85                  90                  95

Ser Asn Phe Ala Val Gly Ala Ala Pro His Pro Phe Leu His Arg Tyr
            100                 105                 110

Tyr Gln Arg Gln Leu Ser Ser Thr Tyr Arg Asp Leu Arg Lys Gly Val
        115                 120                 125

Tyr Val Pro Tyr Thr Gln Gly Lys Trp Glu Gly Glu Leu Gly Thr Asp
    130                 135                 140

Leu Val Ser Ile Pro His Gly Pro Asn Val Thr Val Arg Ala Asn Ile
145                 150                 155                 160

Ala Ala Ile Thr Glu Ser Asp Lys Phe Phe Ile Asn Gly Ser Asn Trp
                165                 170                 175

Glu Gly Ile Leu Gly Leu Ala Tyr Ala Glu Ile Ala Arg Pro Asp Asp
            180                 185                 190

Ser Leu Glu Pro Phe Phe Asp Ser Leu Val Lys Gln Thr His Val Pro
        195                 200                 205

Asn Leu Phe Ser Leu His Leu Cys Gly Ala Gly Phe Pro Leu Asn Gln
    210                 215                 220

Ser Glu Val Leu Ala Ser Val Gly Gly Ser Met Ile Ile Gly Gly Ile
225                 230                 235                 240

Asp His Ser Leu Tyr Thr Gly Ser Leu Trp Tyr Thr Pro Ile Arg Arg
                245                 250                 255

Glu Trp Tyr Tyr Glu Val Ile Ile Val Arg Val Glu Ile Asn Gly Gln
            260                 265                 270

Asp Leu Lys Met Asp Cys Lys Glu Tyr Asn Tyr Asp Lys Ser Ile Val
        275                 280                 285

Asp Ser Gly Thr Thr Asn Leu Arg Leu Pro Lys Lys Val Phe Glu Ala
    290                 295                 300

Ala Val Lys Ser Ile Lys Ala Ala Ser Ser Thr Glu Lys Phe Pro Asp
305                 310                 315                 320

Gly Phe Trp Leu Gly Glu Gln Leu Val Cys Trp Gln Ala Gly Thr Thr
                325                 330                 335

Pro Trp Asn Ile Phe Pro Val Ile Ser Leu Tyr Leu Met Gly Glu Val
            340                 345                 350

Thr Asn Gln Ser Phe Arg Ile Thr Ile Leu Pro Gln Gln Tyr Leu Arg
        355                 360                 365

```
Pro Val Glu Asp Val Ala Thr Ser Gln Asp Asp Cys Tyr Lys Phe Ala
    370                 375                 380
Ile Ser Gln Ser Ser Thr Gly Thr Val Met Gly Ala Val Ile Met Glu
385                 390                 395                 400
Gly Phe Tyr Val Val Phe Asp Arg Ala Arg Lys Arg Ile Gly Phe Ala
                405                 410                 415
Val Ser Ala Cys His Val His Asp Glu Phe Arg Thr Ala Ala Val Glu
            420                 425                 430
Gly Pro Phe Val Thr Leu Asp Met Glu Asp Cys Gly Tyr Asn Ile Pro
        435                 440                 445
Gln Thr Asp Glu Ser Thr Leu Met Thr Ile Ala Tyr Val Met Ala Ala
    450                 455                 460
Ile Cys Ala Leu Phe Met Leu Pro Leu Cys Leu Met Val Cys Gln Trp
465                 470                 475                 480
Arg Cys Leu Arg Cys Leu Arg Gln Gln His Asp Asp Phe Ala Asp Asp
                485                 490                 495
Ile Ser Leu Leu Lys
            500

<210> SEQ ID NO 3
<211> LENGTH: 1977
<212> TYPE: DNA
<213> ORGANISM: Homo sapiens

<400> SEQUENCE: 3
atggcccaag ccctgccctg ctcctgctg tggatgggcg cggagtgct gcctgcccac    60 ggcacccagc acggcatccg gctgcccctg cgcagcggcc tgggggggcgc ccccctgggg   120 ctgcggctgc cccgggagac cgacgaagag cccgaggagc ccggccggag gggcagcttt   180
gtggagatgg tggacaacct gaggggcaag tcggggcagg gctactacgt ggagatgacc   240
gtgggcagcc ccccgcagac gctcaacatc ctggtggata caggcagcag taactttgca   300
gtgggtgctg ccccccaccc cttcctgcat cgctactacc agaggcagct gtccagcaca   360
taccgggacc tccggaaggg tgtgtatgtg ccctacaccc agggcaagtg ggaaggggag   420
ctgggcaccg acctggtaag catccccccat ggccccaacg tcactgtgcg tgccaacatt   480
gctgccatca ctgaatcaga caagttcttc atcaacggct ccaactggga aggcatcctg   540
gggctggcct atgctgagat tgccaggctt tgtggtgctg gcttcccct caaccagtct   600 gaagtgctgg cctctgtcgg agggagcatg atcattgag gtatcgacca ctcgctgtac   660
acaggcagtc tctggtatac acccatccgg cgggagtggt attatgaggt gatcattgtg   720
cgggtggaga tcaatggaca ggatctgaaa atggactgca aggagtacaa ctatgacaag   780
agcattgtgg acagtggcac caccaacctt cgtttgccca gaaagtgtt tgaagctgca   840 gtcaaatcca tcaaggcagc ctcctccacg gagaagttcc ctgatggttt ctggctagga   900
gagcagctgg tgtgctggca agcaggcacc accccttgga acattttccc agtcatctca   960
ctctacctaa tgggtgaggt taccaaccag tccttccgca tcaccatcct tccgcagcaa  1020
tacctgcggc cagtggaaga tgtggccacg tcccaagacg actgttacaa gtttgccatc  1080
tcacagtcat ccacgggcac tgttatggga gctgttatca tggagggctt ctacgttgtc  1140
tttgatcggg cccgaaaacg aattggcttt gctgtcagcg cttgccatgt gcacgatgag  1200
ttcaggacgg cagcggtgga aggccctttt gtcaccttgg acatggaaga ctgtggctac  1260
aacattccac agacagatga gtcaaccctc atgaccatag cctatgtcat ggctgccatc  1320
```

```
tgcgccctct tcatgctgcc actctgcctc atggtgtgtc agtggcgctg cctccgctgc   1380
ctgcgccagc agcatgatga ctttgctgat gacatctccc tgctgaagtg aggaggccca   1440
tgggcagaag atagagattc ccctggacca cactccgtg gttcactttg gtcacaagta    1500
ggagacacag atggcacctg tgccagagc acctcaggac cctccccacc caccaaatgc    1560
ctctgccttg atggagaagg aaaaggctgg caaggtgggt tccagggact gtacctgtag   1620
gaaacagaaa agagaagaaa gaagcactct gctggcggga atactcttgg tcacctcaaa   1680
tttaagtcgg gaaattctgc tgcttgaaac ttcagccctg aacctttgtc caccattcct   1740
ttaaattctc caacccaaag tattcttctt ttcttagttt cagaagtact ggcatcacac   1800
gcaggttacc ttggcgtgtg tccctgtggt accctggcag agaagagacc aagcttgttt   1860
ccctgctggc caaagtcagt aggagaggat gcacagtttg ctatttgctt tagagacagg   1920
gactgtataa acaagcctaa cattggtgca agattgcct  cttgaaaaaa aaaaaaa      1977
```

<210> SEQ ID NO 4
<211> LENGTH: 476
<212> TYPE: PRT
<213> ORGANISM: Homo sapiens

<400> SEQUENCE: 4

```
Met Ala Gln Ala Leu Pro Trp Leu Leu Leu Trp Met Gly Ala Gly Val
  1               5                  10                  15

Leu Pro Ala His Gly Thr Gln His Gly Ile Arg Leu Pro Leu Arg Ser
             20                  25                  30

Gly Leu Gly Gly Ala Pro Leu Gly Leu Arg Leu Pro Arg Glu Thr Asp
         35                  40                  45

Glu Glu Pro Glu Glu Pro Gly Arg Arg Gly Ser Phe Val Glu Met Val
     50                  55                  60

Asp Asn Leu Arg Gly Lys Ser Gly Gln Gly Tyr Tyr Val Glu Met Thr
 65                  70                  75                  80

Val Gly Ser Pro Pro Gln Thr Leu Asn Ile Leu Val Asp Thr Gly Ser
                 85                  90                  95

Ser Asn Phe Ala Val Gly Ala Ala Pro His Pro Phe Leu His Arg Tyr
            100                 105                 110

Tyr Gln Arg Gln Leu Ser Ser Thr Tyr Arg Asp Leu Arg Lys Gly Val
        115                 120                 125

Tyr Val Pro Tyr Thr Gln Gly Lys Trp Glu Gly Glu Leu Gly Thr Asp
    130                 135                 140

Leu Val Ser Ile Pro His Gly Pro Asn Val Thr Val Arg Ala Asn Ile
145                 150                 155                 160

Ala Ala Ile Thr Glu Ser Asp Lys Phe Phe Ile Asn Gly Ser Asn Trp
                165                 170                 175

Glu Gly Ile Leu Gly Leu Ala Tyr Ala Glu Ile Ala Arg Leu Cys Gly
            180                 185                 190

Ala Gly Phe Pro Leu Asn Gln Ser Glu Val Leu Ala Ser Val Gly Gly
        195                 200                 205

Ser Met Ile Ile Gly Gly Ile Asp His Ser Leu Tyr Thr Gly Ser Leu
    210                 215                 220

Trp Tyr Thr Pro Ile Arg Arg Glu Trp Tyr Tyr Glu Val Ile Ile Val
225                 230                 235                 240

Arg Val Glu Ile Asn Gly Gln Asp Leu Lys Met Asp Cys Lys Glu Tyr
                245                 250                 255
```

Asn Tyr Asp Lys Ser Ile Val Asp Ser Gly Thr Thr Asn Leu Arg Leu
            260                 265                 270

Pro Lys Lys Val Phe Glu Ala Ala Val Lys Ser Ile Lys Ala Ala Ser
        275                 280                 285

Ser Thr Glu Lys Phe Pro Asp Gly Phe Trp Leu Gly Glu Gln Leu Val
    290                 295                 300

Cys Trp Gln Ala Gly Thr Thr Pro Trp Asn Ile Phe Pro Val Ile Ser
305                 310                 315                 320

Leu Tyr Leu Met Gly Glu Val Thr Asn Gln Ser Phe Arg Ile Thr Ile
                325                 330                 335

Leu Pro Gln Gln Tyr Leu Arg Pro Val Glu Asp Val Ala Thr Ser Gln
            340                 345                 350

Asp Asp Cys Tyr Lys Phe Ala Ile Ser Gln Ser Ser Thr Gly Thr Val
        355                 360                 365

Met Gly Ala Val Ile Met Glu Gly Phe Tyr Val Val Phe Asp Arg Ala
    370                 375                 380

Arg Lys Arg Ile Gly Phe Ala Val Ser Ala Cys His Val His Asp Glu
385                 390                 395                 400

Phe Arg Thr Ala Ala Val Glu Gly Pro Phe Val Thr Leu Asp Met Glu
                405                 410                 415

Asp Cys Gly Tyr Asn Ile Pro Gln Thr Asp Glu Ser Thr Leu Met Thr
            420                 425                 430

Ile Ala Tyr Val Met Ala Ala Ile Cys Ala Leu Phe Met Leu Pro Leu
        435                 440                 445

Cys Leu Met Val Cys Gln Trp Arg Cys Leu Arg Cys Leu Arg Gln Gln
    450                 455                 460

His Asp Asp Phe Ala Asp Asp Ile Ser Leu Leu Lys
465                 470                 475

<210> SEQ ID NO 5
<211> LENGTH: 14
<212> TYPE: PRT
<213> ORGANISM: Artificial Sequence
<220> FEATURE:
<223> OTHER INFORMATION: Description of Artificial Sequence: synthetic
      peptide sequence

<400> SEQUENCE: 5

Lys Val Glu Ala Asn Tyr Glu Val Glu Gly Glu Arg Lys Lys
 1               5                  10

<210> SEQ ID NO 6
<211> LENGTH: 15
<212> TYPE: PRT
<213> ORGANISM: Artificial Sequence
<220> FEATURE:
<223> OTHER INFORMATION: Description of Artificial Sequence: synthetic
      peptide sequence

<400> SEQUENCE: 6

Lys Val Glu Ala Asn Tyr Glu Val Glu Gly Glu Arg Cys Lys Lys
 1               5                  10                  15

<210> SEQ ID NO 7
<211> LENGTH: 14
<212> TYPE: PRT
<213> ORGANISM: Artificial Sequence
<220> FEATURE:
<223> OTHER INFORMATION: Description of Artificial Sequence: synthetic
      peptide sequence

```
<400> SEQUENCE: 7

Lys Val Glu Ala Asn Tyr Ala Val Glu Gly Glu Arg Lys Lys
  1               5                  10

<210> SEQ ID NO 8
<211> LENGTH: 15
<212> TYPE: PRT
<213> ORGANISM: Artificial Sequence
<220> FEATURE:
<223> OTHER INFORMATION: Description of Artificial Sequence: synthetic
      peptide sequence

<400> SEQUENCE: 8

Lys Val Glu Ala Asn Tyr Ala Val Glu Gly Glu Arg Cys Lys Lys
  1               5                  10                  15

<210> SEQ ID NO 9
<211> LENGTH: 8
<212> TYPE: PRT
<213> ORGANISM: Artificial Sequence
<220> FEATURE:
<223> OTHER INFORMATION: Description of Artificial Sequence: synthetic
      peptide sequence

<400> SEQUENCE: 9

Glu Ala Asn Tyr Glu Val Glu Phe
  1               5

<210> SEQ ID NO 10
<211> LENGTH: 8
<212> TYPE: PRT
<213> ORGANISM: Artificial Sequence
<220> FEATURE:
<223> OTHER INFORMATION: Description of Artificial Sequence: synthetic
      peptide sequence

<400> SEQUENCE: 10

Gly Val Leu Leu Ala Ala Gly Trp
  1               5

<210> SEQ ID NO 11
<211> LENGTH: 8
<212> TYPE: PRT
<213> ORGANISM: Artificial Sequence
<220> FEATURE:
<223> OTHER INFORMATION: Description of Artificial Sequence: synthetic
      peptide sequence

<400> SEQUENCE: 11

Ile Ile Lys Met Asp Asn Phe Gly
  1               5

<210> SEQ ID NO 12
<211> LENGTH: 10
<212> TYPE: PRT
<213> ORGANISM: Artificial Sequence
<220> FEATURE:
<223> OTHER INFORMATION: Description of Artificial Sequence: synthetic
      peptide sequence

<400> SEQUENCE: 12

Asp Ser Ser Asn Leu Glu Met Thr His Ala
  1               5                  10

<210> SEQ ID NO 13
<211> LENGTH: 8
<212> TYPE: PRT
```

```
<213> ORGANISM: Artificial Sequence
<220> FEATURE:
<223> OTHER INFORMATION: Description of Artificial Sequence: synthetic
      peptide sequence
<220> FEATURE:
<221> NAME/KEY: SITE
<222> LOCATION: (7)
<223> OTHER INFORMATION: Xaa=cysteic acid

<400> SEQUENCE: 13

Thr His Gly Phe Gln Leu Xaa His
  1               5

<210> SEQ ID NO 14
<211> LENGTH: 8
<212> TYPE: PRT
<213> ORGANISM: Artificial Sequence
<220> FEATURE:
<223> OTHER INFORMATION: Description of Artificial Sequence: synthetic
      peptide sequence

<400> SEQUENCE: 14

Cys Tyr Thr His Ser Phe Ser Pro
  1               5

<210> SEQ ID NO 15
<211> LENGTH: 8
<212> TYPE: PRT
<213> ORGANISM: Artificial Sequence
<220> FEATURE:
<223> OTHER INFORMATION: Description of Artificial Sequence: synthetic
      peptide sequence
<220> FEATURE:
<221> NAME/KEY: SITE
<222> LOCATION: (4)
<223> OTHER INFORMATION: Xaa= any amino acid
<220> FEATURE:
<221> NAME/KEY: SITE
<222> LOCATION: (7)
<223> OTHER INFORMATION: Xaa= any amino acid

<400> SEQUENCE: 15

Ser Thr Phe Xaa Gly Ser Xaa Gly
  1               5

<210> SEQ ID NO 16
<211> LENGTH: 8
<212> TYPE: PRT
<213> ORGANISM: Artificial Sequence
<220> FEATURE:
<223> OTHER INFORMATION: Description of Artificial Sequence: synthetic
      peptide sequence
<220> FEATURE:
<221> NAME/KEY: SITE
<222> LOCATION: (1)
<223> OTHER INFORMATION: Xaa= any amino acid
<220> FEATURE:
<221> NAME/KEY: SITE
<222> LOCATION: (4)..(7)
<223> OTHER INFORMATION: Xaa= any amino acid

<400> SEQUENCE: 16

Xaa Phe Ala Xaa Xaa Xaa Xaa Asn
  1               5

<210> SEQ ID NO 17
<211> LENGTH: 8
<212> TYPE: PRT
<213> ORGANISM: Artificial Sequence
<220> FEATURE:
<223> OTHER INFORMATION: Description of Artificial Sequence: synthetic
``` peptide sequence
<220> FEATURE:
<221> NAME/KEY: SITE
<222> LOCATION: (1)..(2)
<223> OTHER INFORMATION: Xaa=any amino acid
<220> FEATURE:
<221> NAME/KEY: SITE
<222> LOCATION: (4)..(7)
<223> OTHER INFORMATION: Xaa= any amino acid

<400> SEQUENCE: 17

Xaa Xaa Gln Xaa Xaa Xaa Xaa Ser
 1               5

<210> SEQ ID NO 18
<211> LENGTH: 8
<212> TYPE: PRT
<213> ORGANISM: Artificial Sequence
<220> FEATURE:
<223> OTHER INFORMATION: Description of Artificial Sequence: synthetic
      peptide sequence
<220> FEATURE:
<221> NAME/KEY: SITE
<222> LOCATION: (1)..(2)
<223> OTHER INFORMATION: Xaa= any amino acid
<220> FEATURE:
<221> NAME/KEY: SITE
<222> LOCATION: (4)..(7)
<223> OTHER INFORMATION: Xaa= any amino acid

<400> SEQUENCE: 18

Xaa Xaa Glu Xaa Xaa Xaa Xaa Glu
 1               5

<210> SEQ ID NO 19
<211> LENGTH: 10
<212> TYPE: PRT
<213> ORGANISM: Artificial Sequence
<220> FEATURE:
<223> OTHER INFORMATION: Description of Artificial Sequence: synthetic
      peptide sequence

<400> SEQUENCE: 19

Ser Glu Val Asn Leu Asp Ala Glu Phe Arg
 1               5                  10

<210> SEQ ID NO 20
<211> LENGTH: 10
<212> TYPE: PRT
<213> ORGANISM: Artificial Sequence
<220> FEATURE:
<223> OTHER INFORMATION: Description of Artificial Sequence: synthetic
      peptide sequence

<400> SEQUENCE: 20

Ser Glu Val Lys Met Asp Ala Glu Phe Arg
 1               5                  10

<210> SEQ ID NO 21
<211> LENGTH: 10
<212> TYPE: PRT
<213> ORGANISM: Artificial Sequence
<220> FEATURE:
<223> OTHER INFORMATION: Description of Artificial Sequence: synthetic
      peptide sequence
<220> FEATURE:
<221> NAME/KEY: MOD_RES
<222> LOCATION: (5)
<223> OTHER INFORMATION: Nle

<400> SEQUENCE: 21

```
Ser Glu Val Asn Xaa Asp Ala Glu Phe Arg
  1               5                  10
```

<210> SEQ ID NO 22
<211> LENGTH: 15
<212> TYPE: PRT
<213> ORGANISM: Artificial Sequence
<220> FEATURE:
<223> OTHER INFORMATION: Description of Artificial Sequence: synthetic
      peptide sequence

<400> SEQUENCE: 22

```
Gly Ser Glu Ser Met Asp Ser Gly Ile Ser Leu Asp Asn Lys Trp
  1               5                  10                  15
```

<210> SEQ ID NO 23
<211> LENGTH: 17
<212> TYPE: PRT
<213> ORGANISM: Artificial Sequence
<220> FEATURE:
<223> OTHER INFORMATION: Description of Artificial Sequence: synthetic
      peptide sequence

<400> SEQUENCE: 23

```
Trp Lys Lys Gly Ala Ile Ile Gly Leu Met Val Gly Gly Val Val Lys
  1               5                  10                  15

Lys
```

<210> SEQ ID NO 24
<211> LENGTH: 11
<212> TYPE: PRT
<213> ORGANISM: Artificial Sequence
<220> FEATURE:
<223> OTHER INFORMATION: Description of Artificial Sequence: synthetic
      peptide sequence

<400> SEQUENCE: 24

```
Ala Asn Leu Ser Thr Phe Ala Gln Pro Arg Arg
  1               5                  10
```

<210> SEQ ID NO 25
<211> LENGTH: 20
<212> TYPE: PRT
<213> ORGANISM: Artificial Sequence
<220> FEATURE:
<223> OTHER INFORMATION: Description of Artificial Sequence: synthetic
      peptide sequence

<400> SEQUENCE: 25

```
Glu Phe Arg His Asp Ser Gly Tyr Glu Val His His Gln Lys Leu Val
  1               5                  10                  15

Phe Phe Ala Glu
            20
```

<210> SEQ ID NO 26
<211> LENGTH: 16
<212> TYPE: PRT
<213> ORGANISM: Artificial Sequence
<220> FEATURE:
<223> OTHER INFORMATION: Description of Artificial Sequence: synthetic
      peptide sequence

<400> SEQUENCE: 26

```
Leu Thr Gly Lys Thr Ile Thr Leu Glu Val Glu Pro Ser Asp Thr Ile
  1               5                  10                  15
```

<210> SEQ ID NO 27
<211> LENGTH: 30
<212> TYPE: PRT
<213> ORGANISM: Artificial Sequence
<220> FEATURE:
<223> OTHER INFORMATION: Description of Artificial Sequence: synthetic
      peptide sequence
<220> FEATURE:
<221> NAME/KEY: SITE
<222> LOCATION: (7)
<223> OTHER INFORMATION: Xaa= cysteic acid
<220> FEATURE:
<221> NAME/KEY: SITE
<222> LOCATION: (19)
<223> OTHER INFORMATION: Xaa = cysteic acid

<400> SEQUENCE: 27

Phe Val Asn Gln His Leu Xaa Gly Ser His Leu Val Glu Ala Leu Tyr
 1               5                  10                  15

Leu Val Xaa Gly Glu Arg Gly Phe Phe Tyr Thr Pro Lys Ala
            20                  25                  30

<210> SEQ ID NO 28
<211> LENGTH: 21
<212> TYPE: PRT
<213> ORGANISM: Artificial Sequence
<220> FEATURE:
<223> OTHER INFORMATION: Description of Artificial Sequence: synthetic
<220> FEATURE:
<221> NAME/KEY: SITE
<222> LOCATION: (6)
<223> OTHER INFORMATION: Xaa=cysteic acid
<220> FEATURE:
<221> NAME/KEY: SITE
<222> LOCATION: (7)
<223> OTHER INFORMATION: Xaa=cysteic acid
<220> FEATURE:
<221> NAME/KEY: SITE
<222> LOCATION: (11)
<223> OTHER INFORMATION: Xaa=cysteic acid
<220> FEATURE:
<221> NAME/KEY: SITE
<222> LOCATION: (20)
<223> OTHER INFORMATION: Xaa=cysteic acid

<400> SEQUENCE: 28

Gly Ile Val Glu Gln Xaa Xaa Ala Ser Val Xaa Ser Leu Tyr Gln Leu
 1               5                  10                  15

Glu Asn Tyr Xaa Asn
            20

<210> SEQ ID NO 29
<211> LENGTH: 23
<212> TYPE: PRT
<213> ORGANISM: Artificial Sequence
<220> FEATURE:
<223> OTHER INFORMATION: Description of Artificial Sequence: synthetic
      peptide sequence

<400> SEQUENCE: 29

Tyr Arg Tyr Gln Ser His Asp Tyr Ala Phe Ser Ser Val Glu Lys Leu
 1               5                  10                  15

Leu His Ala Leu Gly Gly Cys
            20

<210> SEQ ID NO 30
<211> LENGTH: 23
<212> TYPE: PRT
<213> ORGANISM: Artificial Sequence

```
<220> FEATURE:
<223> OTHER INFORMATION: Description of Artificial Sequence: synthetic
      peptide sequence

<400> SEQUENCE: 30

Tyr Arg Tyr Gln Ser His Asp Tyr Ala Phe Ser Ser Val Glu Lys Leu
1               5                   10                  15

Leu His Ala Leu Gly Gly Cys
            20

<210> SEQ ID NO 31
<211> LENGTH: 8
<212> TYPE: PRT
<213> ORGANISM: Artificial Sequence
<220> FEATURE:
<223> OTHER INFORMATION: Description of Artificial Sequence: synthetic
      peptide sequence

<400> SEQUENCE: 31

Leu Val Asn Met Ala Glu Gly Asp
1               5

<210> SEQ ID NO 32
<211> LENGTH: 8
<212> TYPE: PRT
<213> ORGANISM: Artificial Sequence
<220> FEATURE:
<223> OTHER INFORMATION: Description of Artificial Sequence: synthetic
      peptide sequence

<400> SEQUENCE: 32

Arg Gly Ser Met Ala Gly Val Leu
1               5

<210> SEQ ID NO 33
<211> LENGTH: 8
<212> TYPE: PRT
<213> ORGANISM: Artificial Sequence
<220> FEATURE:
<223> OTHER INFORMATION: Description of Artificial Sequence: synthetic
      peptide sequence

<400> SEQUENCE: 33

Gly Thr Gln His Gly Ile Arg Leu
1               5

<210> SEQ ID NO 34
<211> LENGTH: 8
<212> TYPE: PRT
<213> ORGANISM: Artificial Sequence
<220> FEATURE:
<223> OTHER INFORMATION: Description of Artificial Sequence: synthetic
      peptide sequence

<400> SEQUENCE: 34

Ser Ser Asn Phe Ala Val Gly Ala
1               5

<210> SEQ ID NO 35
<211> LENGTH: 8
<212> TYPE: PRT
<213> ORGANISM: Artificial Sequence
<220> FEATURE:
<223> OTHER INFORMATION: Description of Artificial Sequence: synthetic
      peptide sequence

<400> SEQUENCE: 35
```

```
Gly Leu Ala Tyr Ala Glu Ile Ala
  1               5

<210> SEQ ID NO 36
<211> LENGTH: 8
<212> TYPE: PRT
<213> ORGANISM: Artificial Sequence
<220> FEATURE:
<223> OTHER INFORMATION: Description of Artificial Sequence: synthetic
      peptide sequence

<400> SEQUENCE: 36

His Leu Cys Gly Ser His Leu Val
  1               5

<210> SEQ ID NO 37
<211> LENGTH: 8
<212> TYPE: PRT
<213> ORGANISM: Artificial Sequence
<220> FEATURE:
<223> OTHER INFORMATION: Description of Artificial Sequence: synthetic
      peptide sequence

<400> SEQUENCE: 37

Cys Gly Glu Arg Gly Phe Phe Tyr
  1               5

<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence: synthetic
      peptide sequence

<400> SEQUENCE: 38

Gly Val Leu Leu Ser Arg Lys
  1               5

<210> SEQ ID NO 39
<211> LENGTH: 7
<212> TYPE: PRT
<213> ORGANISM: Artificial Sequence
<220> FEATURE:
<223> OTHER INFORMATION: Description of Artificial Sequence: synthetic
      peptide sequence

<400> SEQUENCE: 39

Val Gly Ser Gly Val Leu Leu
  1               5

<210> SEQ ID NO 40
<211> LENGTH: 5
<212> TYPE: PRT
<213> ORGANISM: Artificial Sequence
<220> FEATURE:
<223> OTHER INFORMATION: Description of Artificial Sequence: synthetic
      peptide sequence

<400> SEQUENCE: 40

Val Gly Ser Gly Val
  1               5

<210> SEQ ID NO 41
<211> LENGTH: 12
<212> TYPE: PRT
<213> ORGANISM: Artificial Sequence
<220> FEATURE:
```

```
<223> OTHER INFORMATION: Description of Artificial Sequence: synthetic
      peptide sequence
<220> FEATURE:
<221> NAME/KEY: SITE
<222> LOCATION: (9)
<223> OTHER INFORMATION: Xaa= cysteic acid

<400> SEQUENCE: 41

Lys Val Glu Ala Leu Tyr Leu Val Xaa Gly Glu Arg
 1               5                  10

<210> SEQ ID NO 42
<211> LENGTH: 15
<212> TYPE: PRT
<213> ORGANISM: Artificial Sequence
<220> FEATURE:
<223> OTHER INFORMATION: Description of Artificial Sequence: synthetic
      peptide sequence

<400> SEQUENCE: 42

Trp Arg Arg Val Glu Ala Leu Tyr Leu Val Glu Gly Glu Arg Lys
 1               5                  10                  15

<210> SEQ ID NO 43
<211> LENGTH: 14
<212> TYPE: PRT
<213> ORGANISM: Artificial Sequence
<220> FEATURE:
<223> OTHER INFORMATION: Description of Artificial Sequence: synthetic
      peptide sequence

<400> SEQUENCE: 43

Lys Val Glu Ala Asn Tyr Leu Val Glu Gly Glu Arg Lys Lys
 1               5                  10

<210> SEQ ID NO 44
<211> LENGTH: 4
<212> TYPE: PRT
<213> ORGANISM: Artificial Sequence
<220> FEATURE:
<223> OTHER INFORMATION: Description of Artificial Sequence: synthetic
      peptide sequence

<400> SEQUENCE: 44

Met Leu Leu Leu
 1

<210> SEQ ID NO 45
<211> LENGTH: 6
<212> TYPE: PRT
<213> ORGANISM: Artificial Sequence
<220> FEATURE:
<223> OTHER INFORMATION: Description of Artificial Sequence: synthetic
      peptide sequence

<400> SEQUENCE: 45

Asp Ala Ala His Pro Gly
 1               5

<210> SEQ ID NO 46
<211> LENGTH: 14
<212> TYPE: PRT
<213> ORGANISM: Artificial Sequence
<220> FEATURE:
<223> OTHER INFORMATION: Description of Artificial Sequence: synthetic
      peptide sequence

<400> SEQUENCE: 46
```

```
Lys Val Glu Ala Asn Tyr Asp Val Glu Gly Glu Arg Lys Lys
  1               5                  10

<210> SEQ ID NO 47
<211> LENGTH: 14
<212> TYPE: PRT
<213> ORGANISM: Artificial Sequence
<220> FEATURE:
<223> OTHER INFORMATION: Description of Artificial Sequence: synthetic
      peptide sequence

<400> SEQUENCE: 47

Lys Val Glu Ala Asn Leu Ala Val Glu Gly Glu Arg Lys Lys
  1               5                  10

<210> SEQ ID NO 48
<211> LENGTH: 14
<212> TYPE: PRT
<213> ORGANISM: Artificial Sequence
<220> FEATURE:
<223> OTHER INFORMATION: Description of Artificial Sequence: synthetic
      peptide sequence

<400> SEQUENCE: 48

Lys Val Glu Ala Leu Tyr Ala Val Glu Gly Glu Arg Lys Lys
  1               5                  10

<210> SEQ ID NO 49
<211> LENGTH: 8
<212> TYPE: PRT
<213> ORGANISM: Artificial Sequence
<220> FEATURE:
<223> OTHER INFORMATION: Description of Artificial Sequence: synthetic
      peptide sequence
<220> FEATURE:
<221> NAME/KEY: SITE
<222> LOCATION: (1)
<223> OTHER INFORMATION: Xaa = E, G, I, D, T, cysteic acid or S

<400> SEQUENCE: 49

Xaa Ala Asn Tyr Glu Val Glu Phe
  1               5

<210> SEQ ID NO 50
<211> LENGTH: 8
<212> TYPE: PRT
<213> ORGANISM: Artificial Sequence
<220> FEATURE:
<223> OTHER INFORMATION: Description of Artificial Sequence: synthetic
      peptide sequence
<220> FEATURE:
<221> NAME/KEY: SITE
<222> LOCATION: (2)
<223> OTHER INFORMATION: Xaa= A, V, I, S, H, Y, T or F

<400> SEQUENCE: 50

Glu Xaa Asn Tyr Glu Val Glu Phe
  1               5

<210> SEQ ID NO 51
<211> LENGTH: 8
<212> TYPE: PRT
<213> ORGANISM: Artificial Sequence
<220> FEATURE:
<223> OTHER INFORMATION: Description of Artificial Sequence: synthetic
      peptide sequence
<220> FEATURE:
<221> NAME/KEY: SITE
<222> LOCATION: (3)
<223> OTHER INFORMATION: Xaa= N, L, K, S, G, T, D, A, Q, or E
```

```
<400> SEQUENCE: 51

Glu Ala Xaa Tyr Glu Val Glu Phe
 1               5

<210> SEQ ID NO 52
<211> LENGTH: 8
<212> TYPE: PRT
<213> ORGANISM: Artificial Sequence
<220> FEATURE:
<223> OTHER INFORMATION: Description of Artificial Sequence: synthetic
      peptide sequence
<220> FEATURE:
<221> NAME/KEY: SITE
<222> LOCATION: (4)
<223> OTHER INFORMATION: Xaa= Y, L, M, Nle, F or H

<400> SEQUENCE: 52

Glu Ala Asn Xaa Glu Val Glu Phe
 1               5

<210> SEQ ID NO 53
<211> LENGTH: 8
<212> TYPE: PRT
<213> ORGANISM: Artificial Sequence
<220> FEATURE:
<223> OTHER INFORMATION: Description of Artificial Sequence: synthetic
      peptide sequence
<220> FEATURE:
<221> NAME/KEY: SITE
<222> LOCATION: (5)
<223> OTHER INFORMATION: Xaa= E, A, D, M, Q, S or G

<400> SEQUENCE: 53

Glu Ala Asn Tyr Xaa Val Glu Phe
 1               5

<210> SEQ ID NO 54
<211> LENGTH: 8
<212> TYPE: PRT
<213> ORGANISM: Artificial Sequence
<220> FEATURE:
<223> OTHER INFORMATION: Description of Artificial Sequence: synthetic
      peptide sequence
<220> FEATURE:
<221> NAME/KEY: SITE
<222> LOCATION: (6)
<223> OTHER INFORMATION: Xaa= V, A, N, T, L, F or S

<400> SEQUENCE: 54

Glu Ala Asn Tyr Glu Xaa Glu Phe
 1               5

<210> SEQ ID NO 55
<211> LENGTH: 8
<212> TYPE: PRT
<213> ORGANISM: Artificial Sequence
<220> FEATURE:
<223> OTHER INFORMATION: Description of Artificial Sequence: synthetic
      peptide sequence
<220> FEATURE:
<221> NAME/KEY: SITE
<222> LOCATION: (7)
<223> OTHER INFORMATION: Xaa= E, G, F, H, cysteic acid or S

<400> SEQUENCE: 55

Glu Ala Asn Tyr Glu Val Xaa Phe
 1               5
```

```
<210> SEQ ID NO 56
<211> LENGTH: 8
<212> TYPE: PRT
<213> ORGANISM: Artificial Sequence
<220> FEATURE:
<223> OTHER INFORMATION: Description of Artificial Sequence: synthetic
      peptide sequence
<220> FEATURE:
<221> NAME/KEY: SITE
<222> LOCATION: (8)
<223> OTHER INFORMATION: Xaa= F, W, G, A, H, P, G, N, S or E

<400> SEQUENCE: 56

Glu Ala Asn Tyr Glu Val Glu Xaa
  1               5

<210> SEQ ID NO 57
<211> LENGTH: 8
<212> TYPE: PRT
<213> ORGANISM: Artificial Sequence
<220> FEATURE:
<223> OTHER INFORMATION: Description of Artificial Sequence: synthetic
      peptide sequence
<220> FEATURE:
<221> NAME/KEY: SITE
<222> LOCATION: (1)
<223> OTHER INFORMATION: Xaa= E, G, I, D, T, cyeteic acid or S

<400> SEQUENCE: 57

Xaa Val Leu Leu Ala Ala Gly Trp
  1               5

<210> SEQ ID NO 58
<211> LENGTH: 8
<212> TYPE: PRT
<213> ORGANISM: Artificial Sequence
<220> FEATURE:
<223> OTHER INFORMATION: Description of Artificial Sequence: synthetic
      peptide sequence
<220> FEATURE:
<221> NAME/KEY: SITE
<222> LOCATION: (2)
<223> OTHER INFORMATION: Xaa= A, V, I, S, H, Y, T or F

<400> SEQUENCE: 58

Gly Xaa Leu Leu Ala Ala Gly Trp
  1               5

<210> SEQ ID NO 59
<211> LENGTH: 8
<212> TYPE: PRT
<213> ORGANISM: Artificial Sequence
<220> FEATURE:
<223> OTHER INFORMATION: Description of Artificial Sequence: synthetic
      peptide sequence
<220> FEATURE:
<221> NAME/KEY: SITE
<222> LOCATION: (3)
<223> OTHER INFORMATION: Xaa= N, L, K, S, G, T, D, A, Q or E

<400> SEQUENCE: 59

Gly Val Xaa Leu Ala Ala Gly Trp
  1               5

<210> SEQ ID NO 60
<211> LENGTH: 8
<212> TYPE: PRT
<213> ORGANISM: Artificial Sequence
<220> FEATURE:
<223> OTHER INFORMATION: Description of Artificial Sequence: synthetic
      peptide sequence
```

```
<220> FEATURE:
<221> NAME/KEY: SITE
<222> LOCATION: (4)
<223> OTHER INFORMATION: Xaa= Y, L, M, Nle, F or H

<400> SEQUENCE: 60

Gly Val Leu Xaa Ala Ala Gly Trp
 1               5

<210> SEQ ID NO 61
<211> LENGTH: 8
<212> TYPE: PRT
<213> ORGANISM: Artificial Sequence
<220> FEATURE:
<223> OTHER INFORMATION: Description of Artificial Sequence: synthetic
      peptide sequence
<220> FEATURE:
<221> NAME/KEY: SITE
<222> LOCATION: (5)
<223> OTHER INFORMATION: Xaa= E, A, D, M, Q, S or G

<400> SEQUENCE: 61

Gly Val Leu Leu Xaa Ala Gly Trp
 1               5

<210> SEQ ID NO 62
<211> LENGTH: 8
<212> TYPE: PRT
<213> ORGANISM: Artificial Sequence
<220> FEATURE:
<223> OTHER INFORMATION: Description of Artificial Sequence: synthetic
      peptide sequence
<220> FEATURE:
<221> NAME/KEY: SITE
<222> LOCATION: (6)
<223> OTHER INFORMATION: Xaa= V, A, N, T, L, F or S

<400> SEQUENCE: 62

Gly Val Leu Leu Ala Xaa Gly Trp
 1               5

<210> SEQ ID NO 63
<211> LENGTH: 8
<212> TYPE: PRT
<213> ORGANISM: Artificial Sequence
<220> FEATURE:
<223> OTHER INFORMATION: Description of Artificial Sequence: synthetic
      peptide sequence
<220> FEATURE:
<221> NAME/KEY: SITE
<222> LOCATION: (7)
<223> OTHER INFORMATION: Xaa= E, G, F, H, cysteic acid or S

<400> SEQUENCE: 63

Gly Val Leu Leu Ala Ala Xaa Trp
 1               5

<210> SEQ ID NO 64
<211> LENGTH: 8
<212> TYPE: PRT
<213> ORGANISM: Artificial Sequence
<220> FEATURE:
<223> OTHER INFORMATION: Description of Artificial Sequence: synthetic
      peptide sequence
<220> FEATURE:
<221> NAME/KEY: SITE
<222> LOCATION: (8)
<223> OTHER INFORMATION: Xaa= F, W, G, A, H, P, G, N or S

<400> SEQUENCE: 64
```

Gly Val Leu Leu Ala Ala Gly Xaa
 1               5

<210> SEQ ID NO 65
<211> LENGTH: 8
<212> TYPE: PRT
<213> ORGANISM: Artificial Sequence
<220> FEATURE:
<223> OTHER INFORMATION: Description of Artificial Sequence: synthetic
      peptide sequence
<220> FEATURE:
<221> NAME/KEY: SITE
<222> LOCATION: (1)
<223> OTHER INFORMATION: Xaa= E, G, I, D, T, cysteic acid or S

<400> SEQUENCE: 65

Xaa Ile Lys Met Asp Asn Phe Gly
 1               5

<210> SEQ ID NO 66
<211> LENGTH: 8
<212> TYPE: PRT
<213> ORGANISM: Artificial Sequence
<220> FEATURE:
<223> OTHER INFORMATION: Description of Artificial Sequence: synthetic
      peptide sequence
<220> FEATURE:
<221> NAME/KEY: SITE
<222> LOCATION: (2)
<223> OTHER INFORMATION: Xaa= A, V, I, S, H, Y, T or F

<400> SEQUENCE: 66

Ile Xaa Lys Met Asp Asn Phe Gly
 1               5

<210> SEQ ID NO 67
<211> LENGTH: 8
<212> TYPE: PRT
<213> ORGANISM: Artificial Sequence
<220> FEATURE:
<223> OTHER INFORMATION: Description of Artificial Sequence: synthetic
      peptide sequence
<220> FEATURE:
<221> NAME/KEY: SITE
<222> LOCATION: (3)
<223> OTHER INFORMATION: Xaa= N, L, K, S, G, T, D, A, Q or E

<400> SEQUENCE: 67

Ile Ile Xaa Met Asp Asn Phe Gly
 1               5

<210> SEQ ID NO 68
<211> LENGTH: 8
<212> TYPE: PRT
<213> ORGANISM: Artificial Sequence
<220> FEATURE:
<223> OTHER INFORMATION: Description of Artificial Sequence: synthetic
      peptide sequence
<220> FEATURE:
<221> NAME/KEY: SITE
<222> LOCATION: (4)
<223> OTHER INFORMATION: Xaa= Y, L, M, Nle, F or H

<400> SEQUENCE: 68

Ile Ile Lys Xaa Asp Asn Phe Gly
 1               5

<210> SEQ ID NO 69
<211> LENGTH: 8
<212> TYPE: PRT

```
<213> ORGANISM: Artificial Sequence
<220> FEATURE:
<223> OTHER INFORMATION: Description of Artificial Sequence: synthetic
      peptide sequence
<220> FEATURE:
<221> NAME/KEY: SITE
<222> LOCATION: (5)
<223> OTHER INFORMATION: Xaa= E, A, D, M, Q, S or G

<400> SEQUENCE: 69

Ile Ile Lys Met Xaa Asn Phe Gly
  1               5

<210> SEQ ID NO 70
<211> LENGTH: 8
<212> TYPE: PRT
<213> ORGANISM: Artificial Sequence
<220> FEATURE:
<223> OTHER INFORMATION: Description of Artificial Sequence: synthetic
      peptide sequence
<220> FEATURE:
<221> NAME/KEY: SITE
<222> LOCATION: (6)
<223> OTHER INFORMATION: Xaa= V, A, N,T, L, F or S

<400> SEQUENCE: 70

Ile Ile Lys Met Asp Xaa Phe Gly
  1               5

<210> SEQ ID NO 71
<211> LENGTH: 8
<212> TYPE: PRT
<213> ORGANISM: Artificial Sequence
<220> FEATURE:
<223> OTHER INFORMATION: Description of Artificial Sequence: synthetic
      peptide sequence
<220> FEATURE:
<221> NAME/KEY: SITE
<222> LOCATION: (7)
<223> OTHER INFORMATION: Xaa= E, G, F, H, cysteic acid or S

<400> SEQUENCE: 71

Ile Ile Lys Met Asp Asn Xaa Gly
  1               5

<210> SEQ ID NO 72
<211> LENGTH: 8
<212> TYPE: PRT
<213> ORGANISM: Artificial Sequence
<220> FEATURE:
<223> OTHER INFORMATION: Description of Artificial Sequence: synthetic
      peptide sequence
<220> FEATURE:
<221> NAME/KEY: SITE
<222> LOCATION: (8)
<223> OTHER INFORMATION: Xaa= F, W, G, A, H, P, G, N or S

<400> SEQUENCE: 72

Ile Ile Lys Met Asp Asn Phe Xaa
  1               5

<210> SEQ ID NO 73
<211> LENGTH: 10
<212> TYPE: PRT
<213> ORGANISM: Artificial Sequence
<220> FEATURE:
<223> OTHER INFORMATION: Description of Artificial Sequence: synthetic
      peptide sequence
<220> FEATURE:
<221> NAME/KEY: SITE
<222> LOCATION: (1)
```

```
<223> OTHER INFORMATION: Xaa= E, G, I, D, T, cysteic acid or S

<400> SEQUENCE: 73

Xaa Ser Ser Asn Leu Glu Met Thr His Ala
 1               5                  10

<210> SEQ ID NO 74
<211> LENGTH: 10
<212> TYPE: PRT
<213> ORGANISM: Artificial Sequence
<220> FEATURE:
<223> OTHER INFORMATION: Description of Artificial Sequence: synthetic
      peptide sequence
<220> FEATURE:
<221> NAME/KEY: SITE
<222> LOCATION: (2)
<223> OTHER INFORMATION: Xaa= A, V, I, S, H, Y, T or F

<400> SEQUENCE: 74

Asp Xaa Ser Asn Leu Glu Met Thr His Ala
 1               5                  10

<210> SEQ ID NO 75
<211> LENGTH: 10
<212> TYPE: PRT
<213> ORGANISM: Artificial Sequence
<220> FEATURE:
<223> OTHER INFORMATION: Description of Artificial Sequence: synthetic
      peptide sequence
<220> FEATURE:
<221> NAME/KEY: SITE
<222> LOCATION: (3)
<223> OTHER INFORMATION: Xaa= N, L, K, S, G, T, D, A, Q or E

<400> SEQUENCE: 75

Asp Ser Xaa Asn Leu Glu Met Thr His Ala
 1               5                  10

<210> SEQ ID NO 76
<211> LENGTH: 8
<212> TYPE: PRT
<213> ORGANISM: Artificial Sequence
<220> FEATURE:
<223> OTHER INFORMATION: Description of Artificial Sequence: synthetic
      peptide sequence
<220> FEATURE:
<221> NAME/KEY: SITE
<222> LOCATION: (4)
<223> OTHER INFORMATION: Xaa= Y, L, M, Nle, F or H

<400> SEQUENCE: 76

Asp Ser Ser Xaa Met Thr His Ala
 1               5

<210> SEQ ID NO 77
<211> LENGTH: 10
<212> TYPE: PRT
<213> ORGANISM: Artificial Sequence
<220> FEATURE:
<223> OTHER INFORMATION: Description of Artificial Sequence: synthetic
      peptide sequence
<220> FEATURE:
<221> NAME/KEY: SITE
<222> LOCATION: (7)
<223> OTHER INFORMATION: Xaa= E, A, D, M, Q, S or G

<400> SEQUENCE: 77

Asp Ser Ser Asn Leu Glu Xaa Thr His Ala
 1               5                  10
```

```
<210> SEQ ID NO 78
<211> LENGTH: 10
<212> TYPE: PRT
<213> ORGANISM: Artificial Sequence
<220> FEATURE:
<223> OTHER INFORMATION: Description of Artificial Sequence: synthetic
      peptide sequence
<220> FEATURE:
<221> NAME/KEY: SITE
<222> LOCATION: (8)
<223> OTHER INFORMATION: Xaa= V, A, N, T, L, F or S

<400> SEQUENCE: 78

Asp Ser Ser Asn Leu Glu Met Xaa His Ala
 1               5                  10

<210> SEQ ID NO 79
<211> LENGTH: 9
<212> TYPE: PRT
<213> ORGANISM: Artificial Sequence
<220> FEATURE:
<223> OTHER INFORMATION: Description of Artificial Sequence: synthetic
      peptide sequence
<220> FEATURE:
<221> NAME/KEY: SITE
<222> LOCATION: (8)
<223> OTHER INFORMATION: Xaa= E, G, F, H, cysteic acid or S

<400> SEQUENCE: 79

Asp Ser Asn Leu Glu Met Thr Xaa Ala
 1               5

<210> SEQ ID NO 80
<211> LENGTH: 9
<212> TYPE: PRT
<213> ORGANISM: Artificial Sequence
<220> FEATURE:
<223> OTHER INFORMATION: Description of Artificial Sequence: synthetic
      peptide sequence
<220> FEATURE:
<221> NAME/KEY: SITE
<222> LOCATION: (9)
<223> OTHER INFORMATION: Xaa= F, W, G, A, H, P, G, N or S

<400> SEQUENCE: 80

Asp Ser Asn Leu Glu Met Thr His Xaa
 1               5

<210> SEQ ID NO 81
<211> LENGTH: 8
<212> TYPE: PRT
<213> ORGANISM: Artificial Sequence
<220> FEATURE:
<223> OTHER INFORMATION: Description of Artificial Sequence: synthetic
      peptide sequence
<220> FEATURE:
<221> NAME/KEY: SITE
<222> LOCATION: (1)
<223> OTHER INFORMATION: Xaa= E, G, I, D, T, cysteic acid or S
<220> FEATURE:
<221> NAME/KEY: SITE
<222> LOCATION: (7)
<223> OTHER INFORMATION: Xaa= cysteic acid

<400> SEQUENCE: 81

Xaa His Gly Phe Gln Leu Xaa His
 1               5

<210> SEQ ID NO 82
<211> LENGTH: 8
```

```
<212> TYPE: PRT
<213> ORGANISM: Artificial Sequence
<220> FEATURE:
<223> OTHER INFORMATION: Description of Artificial Sequence: synthetic
      peptide sequence
<220> FEATURE:
<221> NAME/KEY: SITE
<222> LOCATION: (2)
<223> OTHER INFORMATION: Xaa= A, V, I, S, H, Y, T or F
<220> FEATURE:
<221> NAME/KEY: SITE
<222> LOCATION: (7)
<223> OTHER INFORMATION: Xaa= cysteic acid

<400> SEQUENCE: 82

Thr Xaa Gly Phe Gln Leu Xaa His
  1               5

<210> SEQ ID NO 83
<211> LENGTH: 8
<212> TYPE: PRT
<213> ORGANISM: Artificial Sequence
<220> FEATURE:
<223> OTHER INFORMATION: Description of Artificial Sequence: synthetic
      peptide sequence
<220> FEATURE:
<221> NAME/KEY: SITE
<222> LOCATION: (3)
<223> OTHER INFORMATION: Xaa= N, L, K, S, G, T, D, A, Q or E
<220> FEATURE:
<221> NAME/KEY: SITE
<222> LOCATION: (7)
<223> OTHER INFORMATION: Xaa= cysteic acid

<400> SEQUENCE: 83

Thr His Xaa Phe Gln Leu Xaa His
  1               5

<210> SEQ ID NO 84
<211> LENGTH: 8
<212> TYPE: PRT
<213> ORGANISM: Artificial Sequence
<220> FEATURE:
<223> OTHER INFORMATION: Description of Artificial Sequence: synthetic
      peptide sequence
<220> FEATURE:
<221> NAME/KEY: SITE
<222> LOCATION: (4)
<223> OTHER INFORMATION: Xaa= Y, L, M, Nle, F or H
<220> FEATURE:
<221> NAME/KEY: SITE
<222> LOCATION: (7)
<223> OTHER INFORMATION: Xaa= cysteic acid

<400> SEQUENCE: 84

Thr His Gly Xaa Gln Leu Xaa His
  1               5

<210> SEQ ID NO 85
<211> LENGTH: 8
<212> TYPE: PRT
<213> ORGANISM: Artificial Sequence
<220> FEATURE:
<223> OTHER INFORMATION: Description of Artificial Sequence: synthetic
      peptide sequence
<220> FEATURE:
<221> NAME/KEY: SITE
<222> LOCATION: (5)
<223> OTHER INFORMATION: Xaa= E, A, D, M, Q, S or G
<220> FEATURE:
<221> NAME/KEY: SITE
<222> LOCATION: (7)
<223> OTHER INFORMATION: Xaa= cysteic acid
```

```
<400> SEQUENCE: 85

Thr His Gly Phe Xaa Leu Xaa His
 1               5

<210> SEQ ID NO 86
<211> LENGTH: 8
<212> TYPE: PRT
<213> ORGANISM: Artificial Sequence
<220> FEATURE:
<223> OTHER INFORMATION: Description of Artificial Sequence: synthetic
      peptide sequence
<220> FEATURE:
<221> NAME/KEY: SITE
<222> LOCATION: (6)
<223> OTHER INFORMATION: Xaa= V, A, N, T, L, F or S
<220> FEATURE:
<221> NAME/KEY: SITE
<222> LOCATION: (7)
<223> OTHER INFORMATION: Xaa= cysteic acid

<400> SEQUENCE: 86

Thr His Gly Phe Gln Xaa Xaa His
 1               5

<210> SEQ ID NO 87
<211> LENGTH: 8
<212> TYPE: PRT
<213> ORGANISM: Artificial Sequence
<220> FEATURE:
<223> OTHER INFORMATION: Description of Artificial Sequence: synthetic
      peptide sequence
<220> FEATURE:
<221> NAME/KEY: SITE
<222> LOCATION: (7)
<223> OTHER INFORMATION: Xaa= E, G, F, H, cysteic acid or S

<400> SEQUENCE: 87

Thr His Gly Phe Gln Leu Xaa His
 1               5

<210> SEQ ID NO 88
<211> LENGTH: 8
<212> TYPE: PRT
<213> ORGANISM: Artificial Sequence
<220> FEATURE:
<223> OTHER INFORMATION: Description of Artificial Sequence: synthetic
      peptide sequence
<220> FEATURE:
<221> NAME/KEY: SITE
<222> LOCATION: (7)
<223> OTHER INFORMATION: Xaa= cysteic acid
<220> FEATURE:
<221> NAME/KEY: SITE
<222> LOCATION: (8)
<223> OTHER INFORMATION: Xaa= F, W, G, A, H, P, G, N or S

<400> SEQUENCE: 88

Thr His Gly Phe Gln Leu Xaa Xaa
 1               5

<210> SEQ ID NO 89
<211> LENGTH: 8
<212> TYPE: PRT
<213> ORGANISM: Artificial Sequence
<220> FEATURE:
<223> OTHER INFORMATION: Description of Artificial Sequence: synthetic
      peptide sequence
<220> FEATURE:
<221> NAME/KEY: SITE
<222> LOCATION: (1)
```

```
<223> OTHER INFORMATION: Xaa= E, G, I, D, T, cysteic acid or S

<400> SEQUENCE: 89

Xaa Tyr Thr His Ser Phe Ser Pro
 1               5

<210> SEQ ID NO 90
<211> LENGTH: 8
<212> TYPE: PRT
<213> ORGANISM: Artificial Sequence
<220> FEATURE:
<223> OTHER INFORMATION: Description of Artificial Sequence: synthetic
      peptide sequence
<220> FEATURE:
<221> NAME/KEY: SITE
<222> LOCATION: (1)
<223> OTHER INFORMATION: Xaa= cysteic acid
<220> FEATURE:
<221> NAME/KEY: SITE
<222> LOCATION: (2)
<223> OTHER INFORMATION: Xaa= A, V, I, S, H, Y, T or F

<400> SEQUENCE: 90

Xaa Xaa Thr His Ser Phe Ser Pro
 1               5

<210> SEQ ID NO 91
<211> LENGTH: 8
<212> TYPE: PRT
<213> ORGANISM: Artificial Sequence
<220> FEATURE:
<223> OTHER INFORMATION: Description of Artificial Sequence: synthetic
      peptide sequence
<220> FEATURE:
<221> NAME/KEY: SITE
<222> LOCATION: (1)
<223> OTHER INFORMATION: Xaa= cysteic acid
<220> FEATURE:
<221> NAME/KEY: SITE
<222> LOCATION: (3)
<223> OTHER INFORMATION: Xaa= N, L, K, S, G, T, D, A, Q or E

<400> SEQUENCE: 91

Xaa Tyr Xaa His Ser Phe Ser Pro
 1               5

<210> SEQ ID NO 92
<211> LENGTH: 8
<212> TYPE: PRT
<213> ORGANISM: Artificial Sequence
<220> FEATURE:
<223> OTHER INFORMATION: Description of Artificial Sequence: synthetic
      peptide sequence
<220> FEATURE:
<221> NAME/KEY: SITE
<222> LOCATION: (1)
<223> OTHER INFORMATION: Xaa= cysteic acid
<220> FEATURE:
<221> NAME/KEY: SITE
<222> LOCATION: (4)
<223> OTHER INFORMATION: Xaa= Y, L, M, Nle, F or H

<400> SEQUENCE: 92

Xaa Tyr Thr Xaa Ser Phe Ser Pro
 1               5

<210> SEQ ID NO 93
<211> LENGTH: 8
<212> TYPE: PRT
<213> ORGANISM: Artificial Sequence
<220> FEATURE:
```

```
<223> OTHER INFORMATION: Description of Artificial Sequence: synthetic
      peptide sequence
<220> FEATURE:
<221> NAME/KEY: SITE
<222> LOCATION: (1)
<223> OTHER INFORMATION: Xaa= cysteic acid
<220> FEATURE:
<221> NAME/KEY: SITE
<222> LOCATION: (5)
<223> OTHER INFORMATION: Xaa= E, A, D, M, Q, S or G

<400> SEQUENCE: 93

Xaa Tyr Thr His Xaa Phe Ser Pro
 1               5

<210> SEQ ID NO 94
<211> LENGTH: 8
<212> TYPE: PRT
<213> ORGANISM: Artificial Sequence
<220> FEATURE:
<223> OTHER INFORMATION: Description of Artificial Sequence: synthetic
      peptide sequence
<220> FEATURE:
<221> NAME/KEY: SITE
<222> LOCATION: (1)
<223> OTHER INFORMATION: Xaa= cysteic acid
<220> FEATURE:
<221> NAME/KEY: SITE
<222> LOCATION: (6)
<223> OTHER INFORMATION: Xaa= V, A, N, T, L, F or S

<400> SEQUENCE: 94

Xaa Tyr Thr His Ser Xaa Ser Pro
 1               5

<210> SEQ ID NO 95
<211> LENGTH: 8
<212> TYPE: PRT
<213> ORGANISM: Artificial Sequence
<220> FEATURE:
<223> OTHER INFORMATION: Description of Artificial Sequence: synthetic
      peptide sequence
<220> FEATURE:
<221> NAME/KEY: SITE
<222> LOCATION: (1)
<223> OTHER INFORMATION: Xaa= cysteic acid
<220> FEATURE:
<221> NAME/KEY: SITE
<222> LOCATION: (7)
<223> OTHER INFORMATION: Xaa=E, G, F, H, cysteic acid or S

<400> SEQUENCE: 95

Xaa Tyr Thr His Ser Phe Xaa Pro
 1               5

<210> SEQ ID NO 96
<211> LENGTH: 8
<212> TYPE: PRT
<213> ORGANISM: Artificial Sequence
<220> FEATURE:
<223> OTHER INFORMATION: Description of Artificial Sequence: synthetic
      peptide sequence
<220> FEATURE:
<221> NAME/KEY: SITE
<222> LOCATION: (1)
<223> OTHER INFORMATION: Xaa=cysteic acid
<220> FEATURE:
<221> NAME/KEY: SITE
<222> LOCATION: (8)
<223> OTHER INFORMATION: Xaa= F, W, G, A, H, P, G, N or S

<400> SEQUENCE: 96
```

```
Xaa Tyr Thr His Ser Phe Ser Xaa
 1               5
```

<210> SEQ ID NO 97
<211> LENGTH: 8
<212> TYPE: PRT
<213> ORGANISM: Artificial Sequence
<220> FEATURE:
<223> OTHER INFORMATION: Description of Artificial Sequence: synthetic
      peptide sequence
<220> FEATURE:
<221> NAME/KEY: SITE
<222> LOCATION: (1)
<223> OTHER INFORMATION: Xaa= E, G, I, D, T, cysteic acid or S
<220> FEATURE:
<221> NAME/KEY: SITE
<222> LOCATION: (7)
<223> OTHER INFORMATION: Xaa= any amino acid
<220> FEATURE:
<221> NAME/KEY: SITE
<222> LOCATION: (4)
<223> OTHER INFORMATION: Xaa= any amino acid

<400> SEQUENCE: 97

```
Xaa Thr Asp Xaa Gly Ser Xaa Gly
 1               5
```

<210> SEQ ID NO 98
<211> LENGTH: 8
<212> TYPE: PRT
<213> ORGANISM: Artificial Sequence
<220> FEATURE:
<223> OTHER INFORMATION: Description of Artificial Sequence: synthetic
      peptide sequence
<220> FEATURE:
<221> NAME/KEY: SITE
<222> LOCATION: (2)
<223> OTHER INFORMATION: Xaa=A, V, I, S, H, Y, T or F
<220> FEATURE:
<221> NAME/KEY: SITE
<222> LOCATION: (4)
<223> OTHER INFORMATION: Xaa= any amino acid
<220> FEATURE:
<221> NAME/KEY: SITE
<222> LOCATION: (7)
<223> OTHER INFORMATION: Xaa= any amino acid

<400> SEQUENCE: 98

```
Ser Xaa Asp Xaa Gly Ser Xaa Gly
 1               5
```

<210> SEQ ID NO 99
<211> LENGTH: 8
<212> TYPE: PRT
<213> ORGANISM: Artificial Sequence
<220> FEATURE:
<223> OTHER INFORMATION: Description of Artificial Sequence: synthetic
      peptide sequence
<220> FEATURE:
<221> NAME/KEY: SITE
<222> LOCATION: (3)
<223> OTHER INFORMATION: Xaa= N, L, K, S, G, T, D, A, Q or E
<220> FEATURE:
<221> NAME/KEY: SITE
<222> LOCATION: (4)
<223> OTHER INFORMATION: Xaa= any amino acid
<220> FEATURE:
<221> NAME/KEY: SITE
<222> LOCATION: (7)
<223> OTHER INFORMATION: Xaa= any amino acid

<400> SEQUENCE: 99

Ser Thr Xaa Xaa Gly Ser Xaa Gly

<210> SEQ ID NO 100
<211> LENGTH: 8
<212> TYPE: PRT
<213> ORGANISM: Artificial Sequence
<220> FEATURE:
<223> OTHER INFORMATION: Description of Artificial Sequence: synthetic
      peptide sequence
<220> FEATURE:
<221> NAME/KEY: SITE
<222> LOCATION: (4)
<223> OTHER INFORMATION: Xaa= Y, L, M, Nle, F or H
<220> FEATURE:
<221> NAME/KEY: SITE
<222> LOCATION: (7)
<223> OTHER INFORMATION: Xaa= any amino acid

<400> SEQUENCE: 100

Ser Thr Asp Xaa Gly Ser Xaa Gly
 1               5

<210> SEQ ID NO 101
<211> LENGTH: 8
<212> TYPE: PRT
<213> ORGANISM: Artificial Sequence
<220> FEATURE:
<223> OTHER INFORMATION: Description of Artificial Sequence: synthetic
      peptide sequence
<220> FEATURE:
<221> NAME/KEY: SITE
<222> LOCATION: (4)
<223> OTHER INFORMATION: Xaa= any amino acid
<220> FEATURE:
<221> NAME/KEY: SITE
<222> LOCATION: (7)
<223> OTHER INFORMATION: Xaa= any amino acid
<220> FEATURE:
<221> NAME/KEY: SITE
<222> LOCATION: (5)
<223> OTHER INFORMATION: Xaa= E, A, D, M, Q, S or G

<400> SEQUENCE: 101

Ser Thr Asp Xaa Xaa Ser Xaa Gly
 1               5

<210> SEQ ID NO 102
<211> LENGTH: 8
<212> TYPE: PRT
<213> ORGANISM: Artificial Sequence
<220> FEATURE:
<223> OTHER INFORMATION: Description of Artificial Sequence: synthetic
      peptide sequence
<220> FEATURE:
<221> NAME/KEY: SITE
<222> LOCATION: (4)
<223> OTHER INFORMATION: Xaa= any amino acid
<220> FEATURE:
<221> NAME/KEY: SITE
<222> LOCATION: (7)
<223> OTHER INFORMATION: Xaa= any amino acid
<220> FEATURE:
<221> NAME/KEY: SITE
<222> LOCATION: (6)
<223> OTHER INFORMATION: Xaa= V, A, N, T, L, F or S

<400> SEQUENCE: 102

Ser Thr Asp Xaa Gly Xaa Xaa Gly
 1               5

<210> SEQ ID NO 103
<211> LENGTH: 8

```
<212> TYPE: PRT
<213> ORGANISM: Artificial Sequence
<220> FEATURE:
<223> OTHER INFORMATION: Description of Artificial Sequence: synthetic
      peptide sequence
<220> FEATURE:
<221> NAME/KEY: SITE
<222> LOCATION: (4)
<223> OTHER INFORMATION: Xaa= any amino acid
<220> FEATURE:
<221> NAME/KEY: SITE
<222> LOCATION: (7)
<223> OTHER INFORMATION: Xaa= E, G, F, H, cysteic acid or S

<400> SEQUENCE: 103

Ser Thr Asp Xaa Gly Ser Xaa Gly
  1               5

<210> SEQ ID NO 104
<211> LENGTH: 8
<212> TYPE: PRT
<213> ORGANISM: Artificial Sequence
<220> FEATURE:
<223> OTHER INFORMATION: Description of Artificial Sequence: synthetic
      peptide sequence
<220> FEATURE:
<221> NAME/KEY: SITE
<222> LOCATION: (4)
<223> OTHER INFORMATION: Xaa= any amino acid
<220> FEATURE:
<221> NAME/KEY: SITE
<222> LOCATION: (7)
<223> OTHER INFORMATION: Xaa= any amino acid
<220> FEATURE:
<221> NAME/KEY: SITE
<222> LOCATION: (8)
<223> OTHER INFORMATION: Xaa=  F, W, G, A, H, P, G, N or S

<400> SEQUENCE: 104

Ser Thr Asp Xaa Gly Ser Xaa Xaa
  1               5

<210> SEQ ID NO 105
<211> LENGTH: 8
<212> TYPE: PRT
<213> ORGANISM: Artificial Sequence
<220> FEATURE:
<223> OTHER INFORMATION: Description of Artificial Sequence: synthetic
      peptide sequence
<220> FEATURE:
<221> NAME/KEY: SITE
<222> LOCATION: (1)
<223> OTHER INFORMATION: Xaa= E, G, I, D, T, cysteic acid or S
<220> FEATURE:
<221> NAME/KEY: SITE
<222> LOCATION: (4)..(7)
<223> OTHER INFORMATION: Xaa= any amino acid

<400> SEQUENCE: 105

Xaa Phe Ala Xaa Xaa Xaa Xaa Asn
  1               5

<210> SEQ ID NO 106
<211> LENGTH: 8
<212> TYPE: PRT
<213> ORGANISM: Artificial Sequence
<220> FEATURE:
<223> OTHER INFORMATION: Description of Artificial Sequence: synthetic
      peptide sequence
<220> FEATURE:
<221> NAME/KEY: SITE
<222> LOCATION: (1)
<223> OTHER INFORMATION: Xaa= any amino acid
```

```
<220> FEATURE:
<221> NAME/KEY: SITE
<222> LOCATION: (2)
<223> OTHER INFORMATION: Xaa= A, V, I, S, H, Y, T or F
<220> FEATURE:
<221> NAME/KEY: SITE
<222> LOCATION: (4)..(7)
<223> OTHER INFORMATION: Xaa= any amino acid

<400> SEQUENCE: 106

Xaa Xaa Ala Xaa Xaa Xaa Xaa Asn
 1               5

<210> SEQ ID NO 107
<211> LENGTH: 8
<212> TYPE: PRT
<213> ORGANISM: Artificial Sequence
<220> FEATURE:
<223> OTHER INFORMATION: Description of Artificial Sequence: synthetic
      peptide sequence
<220> FEATURE:
<221> NAME/KEY: SITE
<222> LOCATION: (1)
<223> OTHER INFORMATION: Xaa= any amino acid
<220> FEATURE:
<221> NAME/KEY: SITE
<222> LOCATION: (3)
<223> OTHER INFORMATION: Xaa= N, L, K, S, G, T, D, A, Q or E
<220> FEATURE:
<221> NAME/KEY: SITE
<222> LOCATION: (4)..(7)
<223> OTHER INFORMATION: Xaa= any amino acid

<400> SEQUENCE: 107

Xaa Phe Xaa Xaa Xaa Xaa Xaa Asn
 1               5

<210> SEQ ID NO 108
<211> LENGTH: 8
<212> TYPE: PRT
<213> ORGANISM: Artificial Sequence
<220> FEATURE:
<223> OTHER INFORMATION: Description of Artificial Sequence: synthetic
      peptide sequence
<220> FEATURE:
<221> NAME/KEY: SITE
<222> LOCATION: (1)
<223> OTHER INFORMATION: Xaa= any amino acid
<220> FEATURE:
<221> NAME/KEY: SITE
<222> LOCATION: (4)
<223> OTHER INFORMATION: Xaa= Y, L, M, Nle, F or  H
<220> FEATURE:
<221> NAME/KEY: SITE
<222> LOCATION: (5)..(7)
<223> OTHER INFORMATION: Xaa= any amino acid

<400> SEQUENCE: 108

Xaa Phe Ala Xaa Xaa Xaa Xaa Asn
 1               5

<210> SEQ ID NO 109
<211> LENGTH: 8
<212> TYPE: PRT
<213> ORGANISM: Artificial Sequence
<220> FEATURE:
<223> OTHER INFORMATION: Description of Artificial Sequence: synthetic
      peptide sequence
<220> FEATURE:
<221> NAME/KEY: SITE
<222> LOCATION: (1)
<223> OTHER INFORMATION: Xaa= any amino acid
<220> FEATURE:
```

```
<221> NAME/KEY: SITE
<222> LOCATION: (4)
<223> OTHER INFORMATION: Xaa = any amino acid
<220> FEATURE:
<221> NAME/KEY: SITE
<222> LOCATION: (5)
<223> OTHER INFORMATION: Xaa= E, A, D, M, Q, S or G
<220> FEATURE:
<221> NAME/KEY: SITE
<222> LOCATION: (6)..(7)
<223> OTHER INFORMATION: Xaa= any amino acid

<400> SEQUENCE: 109

Xaa Phe Ala Xaa Xaa Xaa Xaa Asn
 1               5

<210> SEQ ID NO 110
<211> LENGTH: 8
<212> TYPE: PRT
<213> ORGANISM: Artificial Sequence
<220> FEATURE:
<223> OTHER INFORMATION: Description of Artificial Sequence: synthetic
      peptide sequence
<220> FEATURE:
<221> NAME/KEY: SITE
<222> LOCATION: (1)
<223> OTHER INFORMATION: Xaa= any amino acid
<220> FEATURE:
<221> NAME/KEY: SITE
<222> LOCATION: (4)..(5)
<223> OTHER INFORMATION: Xaa= any amino acid
<220> FEATURE:
<221> NAME/KEY: SITE
<222> LOCATION: (6)
<223> OTHER INFORMATION: Xaa= V, A, N, T, L, F  or S
<220> FEATURE:
<221> NAME/KEY: SITE
<222> LOCATION: (7)
<223> OTHER INFORMATION: Xaa= any amino acid

<400> SEQUENCE: 110

Xaa Phe Ala Xaa Xaa Xaa Xaa Asn
 1               5

<210> SEQ ID NO 111
<211> LENGTH: 8
<212> TYPE: PRT
<213> ORGANISM: Artificial Sequence
<220> FEATURE:
<223> OTHER INFORMATION: Description of Artificial Sequence: synthetic
      peptide sequence
<220> FEATURE:
<221> NAME/KEY: SITE
<222> LOCATION: (1)
<223> OTHER INFORMATION: Xaa= any amino acid
<220> FEATURE:
<221> NAME/KEY: SITE
<222> LOCATION: (4)..(6)
<223> OTHER INFORMATION: Xaa= any amino acid
<220> FEATURE:
<221> NAME/KEY: SITE
<222> LOCATION: (7)
<223> OTHER INFORMATION: Xaa= E, G, F, H, cysteic acid or S

<400> SEQUENCE: 111

Xaa Phe Ala Xaa Xaa Xaa Xaa Asn
 1               5

<210> SEQ ID NO 112
<211> LENGTH: 8
<212> TYPE: PRT
<213> ORGANISM: Artificial Sequence
<220> FEATURE:
```

```
<223> OTHER INFORMATION: Description of Artificial Sequence: synthetic
      peptide sequence
<220> FEATURE:
<221> NAME/KEY: SITE
<222> LOCATION: (1)
<223> OTHER INFORMATION: Xaa= any amino acid
<220> FEATURE:
<221> NAME/KEY: SITE
<222> LOCATION: (4)..(7)
<223> OTHER INFORMATION: Xaa= any amino acid
<220> FEATURE:
<221> NAME/KEY: SITE
<222> LOCATION: (8)
<223> OTHER INFORMATION: Xaa= F, W, G, A, H, P, G, N or  S

<400> SEQUENCE: 112

Xaa Phe Ala Xaa Xaa Xaa Xaa Xaa
 1               5

<210> SEQ ID NO 113
<211> LENGTH: 9
<212> TYPE: PRT
<213> ORGANISM: Artificial Sequence
<220> FEATURE:
<223> OTHER INFORMATION: Description of Artificial Sequence: synthetic
      peptide sequence

<400> SEQUENCE: 113

Glu Val Asn Leu Asp Ala Glu Phe Arg
 1               5

<210> SEQ ID NO 114
<211> LENGTH: 7
<212> TYPE: PRT
<213> ORGANISM: Artificial Sequence
<220> FEATURE:
<223> OTHER INFORMATION: Description of Artificial Sequence: synthetic
      peptide sequence

<400> SEQUENCE: 114

Asp Tyr Lys Asp Asp Asp Lys
 1               5

<210> SEQ ID NO 115
<211> LENGTH: 17
<212> TYPE: PRT
<213> ORGANISM: Artificial Sequence
<220> FEATURE:
<223> OTHER INFORMATION: Description of Artificial Sequence: synthetic
      peptide sequence

<400> SEQUENCE: 115

Ala Cys Gly Ser Glu Ser Met Asp Ser Gly Ile Ser Leu Asp Asn Lys
 1               5                  10                  15

Trp

<210> SEQ ID NO 116
<211> LENGTH: 17
<212> TYPE: PRT
<213> ORGANISM: Artificial Sequence
<220> FEATURE:
<223> OTHER INFORMATION: Description of Artificial Sequence: synthetic
      peptide sequence

<400> SEQUENCE: 116

Trp Lys Lys Gly Ala Ile Ile Gly Leu Met Val Gly Gly Val Val Lys
 1               5                  10                  15

Lys
```

<210> SEQ ID NO 117
<211> LENGTH: 11
<212> TYPE: PRT
<213> ORGANISM: Artificial Sequence
<220> FEATURE:
<223> OTHER INFORMATION: Description of Artificial Sequence: synthetic
      peptide sequence

<400> SEQUENCE: 117

Ala Asn Leu Ser Thr Phe Ala Gln Pro Arg Arg
 1               5                  10

<210> SEQ ID NO 118
<211> LENGTH: 22
<212> TYPE: PRT
<213> ORGANISM: Artificial Sequence
<220> FEATURE:
<223> OTHER INFORMATION: Description of Artificial Sequence: synthetic
      peptide sequence

<400> SEQUENCE: 118

Tyr Arg Tyr Gln Ser His Asp Tyr Ala Phe Ser Ser Val Glu Lys Leu
 1               5                  10                  15

Leu His Leu Gly Gly Cys
            20

<210> SEQ ID NO 119
<211> LENGTH: 22
<212> TYPE: PRT
<213> ORGANISM: Artificial Sequence
<220> FEATURE:
<223> OTHER INFORMATION: Description of Artificial Sequence: synthetic
      peptide sequence

<400> SEQUENCE: 119

Tyr Arg Tyr Gln Ser His Asp Tyr Ala Phe Ser Ser Val Glu Lys Leu
 1               5                  10                  15

Leu His Leu Gly Gly Cys
            20

<210> SEQ ID NO 120
<211> LENGTH: 10
<212> TYPE: PRT
<213> ORGANISM: Artificial Sequence
<220> FEATURE:
<223> OTHER INFORMATION: Description of Artificial Sequence: synthetic
      peptide sequence

<400> SEQUENCE: 120

Lys Thr Ile Thr Leu Glu Val Glu Pro Ser
 1               5                  10

<210> SEQ ID NO 121
<211> LENGTH: 12
<212> TYPE: PRT
<213> ORGANISM: Artificial Sequence
<220> FEATURE:
<223> OTHER INFORMATION: Description of Artificial Sequence: synthetic
      peptide sequence
<220> FEATURE:
<221> NAME/KEY: SITE
<222> LOCATION: (9)
<223> OTHER INFORMATION: Xaa= cysteic acid

<400> SEQUENCE: 121

Val Glu Ala Leu Tyr Leu Val Cys Xaa Gly Glu Arg

```
                1               5                    10
```

<210> SEQ ID NO 122
<211> LENGTH: 11
<212> TYPE: PRT
<213> ORGANISM: Artificial Sequence
<220> FEATURE:
<223> OTHER INFORMATION: Description of Artificial Sequence: synthetic
      peptide sequence

<400> SEQUENCE: 122

Val Glu Ala Leu Tyr Leu Val Glu Gly Glu Arg
 1               5                   10

<210> SEQ ID NO 123
<211> LENGTH: 363
<212> TYPE: PRT
<213> ORGANISM: Homo sapiens
<220> FEATURE:
<223> OTHER INFORMATION: galactosyltransferase

<400> SEQUENCE: 123

Met Ala Ser Lys Ser Trp Leu Asn Phe Leu Thr Phe Leu Cys Gly Ser
 1               5                   10                  15

Ala Ile Gly Phe Leu Leu Cys Ser Gln Leu Phe Ser Ile Leu Leu Gly
            20                  25                  30

Glu Lys Val Asp Thr Gln Pro Asn Val Leu His Asn Asp Pro His Ala
        35                  40                  45

Arg His Ser Asp Asp Asn Gly Gln Asn His Leu Glu Gly Gln Met Asn
    50                  55                  60

Phe Asn Ala Asp Ser Ser Gln His Lys Asp Glu Asn Thr Asp Ile Ala
65                  70                  75                  80

Glu Asn Leu Tyr Gln Lys Val Arg Ile Leu Cys Trp Val Met Thr Gly
                85                  90                  95

Pro Gln Asn Leu Glu Lys Lys Ala Lys His Val Lys Ala Thr Trp Ala
            100                 105                 110

Gln Arg Cys Asn Lys Val Leu Phe Met Ser Ser Glu Glu Asn Lys Asp
        115                 120                 125

Phe Pro Ala Val Gly Leu Lys Thr Lys Glu Gly Arg Asp Gln Leu Tyr
    130                 135                 140

Trp Lys Thr Ile Lys Ala Phe Gln Tyr Val His Glu His Tyr Leu Glu
145                 150                 155                 160

Asp Ala Asp Trp Phe Leu Lys Ala Asp Asp Thr Tyr Val Ile Leu
                165                 170                 175

Asp Asn Leu Arg Trp Leu Leu Ser Lys Tyr Asp Pro Glu Glu Pro Ile
            180                 185                 190

Tyr Phe Gly Arg Arg Phe Lys Pro Tyr Val Lys Gln Gly Tyr Met Ser
        195                 200                 205

Gly Gly Ala Gly Tyr Val Leu Ser Lys Glu Ala Leu Lys Arg Phe Val
    210                 215                 220

Asp Ala Phe Lys Thr Asp Lys Cys Thr His Ser Ser Ser Ile Glu Asp
225                 230                 235                 240

Leu Ala Leu Gly Arg Cys Met Glu Ile Met Asn Val Glu Ala Gly Asp
                245                 250                 255

Ser Arg Asp Thr Ile Gly Lys Glu Thr Phe His Pro Phe Val Pro Glu
            260                 265                 270

His His Leu Ile Lys Gly Tyr Leu Pro Arg Thr Phe Trp Tyr Trp Asn
        275                 280                 285

```
Tyr Asn Tyr Tyr Pro Val Glu Gly Pro Gly Cys Cys Ser Asp Leu
        290                 295                 300

Ala Val Ser Phe His Tyr Val Asp Ser Thr Thr Met Tyr Glu Leu Glu
305                 310                 315                 320

Tyr Leu Val Tyr His Leu Arg Pro Tyr Gly Tyr Leu Tyr Arg Tyr Gln
                325                 330                 335

Pro Thr Leu Pro Glu Arg Ile Leu Lys Glu Ile Ser Gln Ala Asn Lys
                340                 345                 350

Asn Glu Asp Thr Lys Val Lys Leu Gly Asn Pro
        355                 360

<210> SEQ ID NO 124
<211> LENGTH: 405
<212> TYPE: PRT
<213> ORGANISM: Homo sapiens
<220> FEATURE:
<223> OTHER INFORMATION: Homo sapiens sialylytransferase 1

<400> SEQUENCE: 124

Ile His Thr Asn Leu Lys Lys Lys Phe Ser Cys Cys Val Leu Val Phe
  1               5                  10                  15

Leu Leu Phe Ala Val Ile Cys Val Trp Lys Glu Lys Lys Lys Gly Ser
                 20                  25                  30

Tyr Tyr Asp Ser Phe Lys Leu Gln Thr Lys Glu Phe Gln Val Leu Lys
             35                  40                  45

Ser Leu Gly Lys Leu Ala Met Gly Ser Asp Ser Gln Ser Val Ser Ser
         50                  55                  60

Ser Ser Thr Gln Asp Pro His Arg Gly Arg Gln Thr Leu Gly Ser Leu
 65                  70                  75                  80

Arg Gly Leu Ala Lys Ala Lys Pro Glu Ala Ser Phe Gln Val Trp Asn
                 85                  90                  95

Lys Asp Ser Ser Lys Asn Leu Ile Pro Arg Leu Gln Lys Ile Trp
                100                 105                 110

Lys Asn Tyr Leu Ser Met Asn Lys Tyr Lys Val Ser Tyr Lys Gly Pro
            115                 120                 125

Gly Pro Gly Ile Lys Phe Ser Ala Glu Ala Leu Arg Cys His Leu Arg
        130                 135                 140

Asp His Val Asn Val Ser Met Val Glu Val Thr Asp Phe Pro Phe Asn
145                 150                 155                 160

Thr Ser Glu Trp Glu Gly Tyr Leu Pro Lys Glu Ser Ile Arg Thr Lys
                165                 170                 175

Ala Gly Pro Trp Gly Arg Cys Ala Val Val Ser Ser Ala Gly Ser Leu
            180                 185                 190

Lys Ser Ser Gln Leu Gly Arg Glu Ile Asp Asp His Asp Ala Val Leu
        195                 200                 205

Arg Phe Asn Gly Ala Pro Thr Ala Asn Phe Gln Gln Asp Val Gly Thr
    210                 215                 220

Lys Thr Thr Ile Arg Leu Met Asn Ser Gln Leu Val Thr Thr Glu Lys
225                 230                 235                 240

Arg Phe Leu Lys Asp Ser Leu Tyr Asn Glu Gly Ile Leu Ile Val Trp
                245                 250                 255

Asp Pro Ser Val Tyr His Ser Asp Ile Pro Lys Trp Tyr Gln Asn Pro
            260                 265                 270

Asp Tyr Asn Phe Phe Asn Asn Tyr Lys Thr Tyr Arg Lys Leu His Pro
        275                 280                 285
```

```
Asn Gln Pro Phe Tyr Ile Leu Lys Pro Gln Met Pro Trp Glu Leu Trp
    290                 295                 300
Asp Ile Leu Gln Glu Ile Ser Pro Glu Glu Ile Gln Pro Asn Pro Pro
305                 310                 315                 320
Ser Ser Gly Met Leu Gly Ile Ile Met Met Thr Leu Cys Asp Gln
                325                 330                 335
Val Asp Ile Tyr Glu Phe Leu Pro Ser Lys Arg Lys Thr Asp Val Cys
            340                 345                 350
Tyr Tyr Tyr Gln Lys Phe Phe Asp Ser Ala Cys Thr Met Gly Ala Tyr
        355                 360                 365
His Pro Leu Leu Tyr Glu Lys Asn Leu Val Lys His Leu Asn Gln Gly
    370                 375                 380
Thr Asp Glu Asp Ile Tyr Leu Leu Gly Lys Ala Thr Leu Pro Gly Phe
385                 390                 395                 400
Arg Thr Ile His Cys
            405

<210> SEQ ID NO 125
<211> LENGTH: 518
<212> TYPE: PRT
<213> ORGANISM: Homo sapiens
<220> FEATURE:
<223> OTHER INFORMATION: Homo sapiens aspartyl protease 1

<400> SEQUENCE: 125

Met Gly Ala Leu Ala Arg Ala Leu Leu Leu Pro Leu Leu Ala Gln Trp
1               5                   10                  15
Leu Leu Arg Ala Ala Pro Glu Leu Ala Pro Ala Pro Phe Thr Leu Pro
            20                  25                  30
Leu Arg Val Ala Ala Ala Thr Asn Arg Val Val Ala Pro Thr Pro Gly
        35                  40                  45
Pro Gly Thr Pro Ala Glu Arg His Ala Asp Gly Leu Ala Leu Ala Leu
    50                  55                  60
Glu Pro Ala Leu Ala Ser Pro Ala Gly Ala Ala Asn Phe Leu Ala Met
65                  70                  75                  80
Val Asp Asn Leu Gln Gly Asp Ser Gly Arg Gly Tyr Tyr Leu Glu Met
                85                  90                  95
Leu Ile Gly Thr Pro Pro Gln Lys Leu Gln Ile Leu Val Asp Thr Gly
            100                 105                 110
Ser Ser Asn Phe Ala Val Ala Gly Thr Pro His Ser Tyr Ile Asp Thr
        115                 120                 125
Tyr Phe Asp Thr Glu Arg Ser Ser Thr Tyr Arg Ser Lys Gly Phe Asp
    130                 135                 140
Val Thr Val Lys Tyr Thr Gln Gly Ser Trp Thr Gly Phe Val Gly Glu
145                 150                 155                 160
Asp Leu Val Thr Ile Pro Lys Gly Phe Asn Thr Ser Phe Leu Val Asn
                165                 170                 175
Ile Ala Thr Ile Phe Glu Ser Glu Asn Phe Phe Leu Pro Gly Ile Lys
            180                 185                 190
Trp Asn Gly Ile Leu Gly Leu Ala Tyr Ala Thr Leu Ala Lys Pro Ser
        195                 200                 205
Ser Ser Leu Glu Thr Phe Phe Asp Ser Leu Val Thr Gln Ala Asn Ile
    210                 215                 220
Pro Asn Val Phe Ser Met Gln Met Cys Gly Ala Gly Leu Pro Val Ala
225                 230                 235                 240
```

```
Gly Ser Gly Thr Asn Gly Gly Ser Leu Val Leu Gly Gly Ile Glu Pro
                245                 250                 255

Ser Leu Tyr Lys Gly Asp Ile Trp Tyr Thr Pro Ile Lys Glu Glu Trp
            260                 265                 270

Tyr Tyr Gln Ile Glu Ile Leu Lys Leu Glu Ile Gly Gly Gln Ser Leu
        275                 280                 285

Asn Leu Asp Cys Arg Glu Tyr Asn Ala Asp Lys Ala Ile Val Asp Ser
    290                 295                 300

Gly Thr Thr Leu Leu Arg Leu Pro Gln Lys Val Phe Asp Ala Val Val
305                 310                 315                 320

Glu Ala Val Ala Arg Ala Ser Leu Ile Pro Glu Phe Ser Asp Gly Phe
                325                 330                 335

Trp Thr Gly Ser Gln Leu Ala Cys Trp Thr Asn Ser Glu Thr Pro Trp
            340                 345                 350

Ser Tyr Phe Pro Lys Ile Ser Ile Tyr Leu Arg Asp Glu Asn Ser Ser
        355                 360                 365

Arg Ser Phe Arg Ile Thr Ile Leu Pro Gln Leu Tyr Ile Gln Pro Met
    370                 375                 380

Met Gly Ala Gly Leu Asn Tyr Glu Cys Tyr Arg Phe Gly Ile Ser Pro
385                 390                 395                 400

Ser Thr Asn Ala Leu Val Ile Gly Ala Thr Val Met Glu Gly Phe Tyr
                405                 410                 415

Val Ile Phe Asp Arg Ala Gln Lys Arg Val Gly Phe Ala Ala Ser Pro
            420                 425                 430

Cys Ala Glu Ile Ala Gly Ala Ala Val Ser Glu Ile Ser Gly Pro Phe
        435                 440                 445

Ser Thr Glu Asp Val Ala Ser Asn Cys Val Pro Ala Gln Ser Leu Ser
    450                 455                 460

Glu Pro Ile Leu Trp Ile Val Ser Tyr Ala Leu Met Ser Val Cys Gly
465                 470                 475                 480

Ala Ile Leu Leu Val Leu Ile Val Leu Leu Leu Pro Phe Arg Cys
                485                 490                 495

Gln Arg Arg Pro Arg Asp Pro Glu Val Val Asn Asp Glu Ser Ser Leu
            500                 505                 510

Val Arg His Arg Trp Lys
        515

<210> SEQ ID NO 126
<211> LENGTH: 255
<212> TYPE: PRT
<213> ORGANISM: Homo sapiens
<220> FEATURE:
<223> OTHER INFORMATION: Homo sapiens syntaxin 6

<400> SEQUENCE: 126

Met Ser Met Glu Asp Pro Phe Phe Val Val Lys Gly Glu Val Gln Lys
1               5                   10                  15

Ala Val Asn Thr Ala Gln Gly Leu Phe Gln Arg Trp Thr Glu Leu Leu
            20                  25                  30

Gln Asp Pro Ser Thr Ala Thr Arg Glu Glu Ile Asp Trp Thr Thr Asn
        35                  40                  45

Glu Leu Arg Asn Asn Leu Arg Ser Ile Glu Trp Asp Leu Glu Asp Leu
    50                  55                  60

Asp Glu Thr Ile Ser Ile Val Glu Ala Asn Pro Arg Lys Phe Asn Leu
65                  70                  75                  80
```

```
Asp Ala Thr Glu Leu Ser Ile Arg Lys Ala Phe Ile Thr Ser Thr Arg
                85                  90                  95

Gln Val Val Arg Asp Met Lys Asp Gln Met Ser Thr Ser Ser Val Gln
            100                 105                 110

Ala Leu Ala Glu Arg Lys Asn Arg Gln Ala Leu Leu Gly Asp Ser Gly
        115                 120                 125

Ser Gln Asn Trp Ser Thr Gly Thr Thr Asp Lys Tyr Gly Arg Leu Asp
    130                 135                 140

Arg Glu Leu Gln Arg Ala Asn Ser His Phe Ile Glu Glu Gln Gln Ala
145                 150                 155                 160

Gln Gln Gln Leu Ile Val Glu Gln Gln Asp Glu Gln Leu Glu Leu Val
            165                 170                 175

Ser Gly Ser Ile Gly Val Leu Lys Asn Met Ser Gln Arg Ile Gly Gly
            180                 185                 190

Glu Leu Glu Glu Gln Ala Val Met Leu Glu Asp Phe Ser His Glu Leu
        195                 200                 205

Glu Ser Thr Gln Ser Arg Leu Asp Asn Val Met Lys Lys Leu Ala Lys
    210                 215                 220

Val Ser His Met Thr Ser Asp Arg Arg Gln Trp Cys Ala Ile Ala Ile
225                 230                 235                 240

Leu Phe Ala Val Leu Leu Val Val Leu Ile Leu Phe Leu Val Leu
                245                 250                 255

<210> SEQ ID NO 127
<211> LENGTH: 1728
<212> TYPE: DNA
<213> ORGANISM: Artificial Sequence
<220> FEATURE:
<223> OTHER INFORMATION: Description of Artificial Sequence: nucleic
      acid encoding recombinant fusion protein

<400> SEQUENCE: 127
atgctgctgc tgctgctgct gctgggcctg aggctacagc tctccctggg catcatccca    60
gttgaggagg agaacccgga cttctggaac cgcgaggcag ccgaggccct gggtgccgcc   120
aagaagctgc agcctgcaca gacagccgcc aagaacctca tcatcttcct gggcgatggg   180
atggggtgt ctacggtgac agctgccagg atcctaaaag gcagaagaa ggacaaactg    240
gggcctgaga taccctggc catggaccgc ttcccatatg tggctctgtc aagacatac    300
aatgtagaca acatgtgcc agacagtgga gccacagcca cggcctacct gtgcggggtc    360
aagggcaact tccagaccat tggcttgagt gcagccgccc gctttaacca gtgcaacacg    420
acacgcggca cgaggtcat ctccgtgatg aatcgggcca agaaagcagg gaagtcagtg    480
ggagtggtaa ccaccacacg agtgcagcac gcctcgccag ccggcaccta cgcccacacg    540
gtgaaccgca actggtactc ggacgccgac gtgcctgcct cggcccgcca ggaggggtgc    600
caggacatcg ctacgcagct catctccaac atggacattg acgtgatcct aggtggaggc    660
cgaaagtaca tgtttcccat gggaacccca gaccctgagt acccagatga ctacagccaa    720
ggtgggacca ggctggacgg gaagaatctg gtgcaggaat ggctggcgaa gcgccagggt    780
gcccggtatg tgtggaaccg cactgagctc atgcaggctt ccctggaccc gtctgtgacc    840
catctcatgg gtctctttga gcctggagac atgaaatacg agatccaccg agactccaca    900
ctggaccccc ccctgatgga gatgacagag gctgccctgc gctgctgag caggaacccc    960
cgcggcttct tcctcttcgt ggagggtggt cgcatcgacc atggtcatca tgaaagcagg   1020
```

```
gcttaccggg cactgactga gacgatcatg ttcgacgacg ccattgagag ggcgggccag    1080
ctcaccagcg aggaggacac gctgagcctc gtcactgccg accactccca cgtcttctcc    1140
ttcggaggct accccctgcg agggagctcc atcttcgggc tggcccctgg caaggcccgg    1200
gacaggaagg cctacacggt cctcctatac ggaaacggtc caggctatgt gctcaaggac    1260
ggcgcccggc cggatgttac cgagagcgag agcgggagcc ccgagtatcg gcagcagtca    1320
gcagtgcccc tggacgaaga gacccacgca ggcgaggacg tggcggtgtt cgcgcgcggc    1380
ccgcaggcgc acctggttca cggcgtgcag gagcagacct tcatagcgca cgtcatggcc    1440
ttcgccgcct gcctggagcc ctacaccgcc tgcgacctgg cgcccccgc cggcaccacc     1500 gacgccgcgc acccaggtaa ctatgaagtt gaattccgaa gagcactcta cgtagagggt    1560
gaaagaggat tcttctacac tccaaaggca ctctacctcg tagagggtga aagaggattc    1620
ttctacacta gtctcatgac catagcctat gtcatggctg ccatctgcgc cctcttcatg    1680
ctgccactct gcctcatggt ggactacaag gatgatgatg acaagtag                 1728
```

<210> SEQ ID NO 128
<211> LENGTH: 575
<212> TYPE: PRT
<213> ORGANISM: Artificial Sequence
<220> FEATURE:
<223> OTHER INFORMATION: Description of Artificial Sequence: recombinant
      fusion protein sequence

<400> SEQUENCE: 128

```
Met Leu Leu Leu Leu Leu Leu Gly Leu Arg Leu Gln Leu Ser Leu
 1               5                   10                  15

Gly Ile Ile Pro Val Glu Glu Asn Pro Asp Phe Trp Asn Arg Glu
                20                  25                  30

Ala Glu Ala Leu Gly Ala Ala Lys Lys Leu Gln Pro Ala Gln Thr
            35                  40                  45

Ala Ala Lys Asn Leu Ile Ile Phe Leu Gly Asp Gly Met Gly Val Ser
    50                  55                  60

Thr Val Thr Ala Ala Arg Ile Leu Lys Gly Gln Lys Lys Asp Lys Leu
65                  70                  75                  80

Gly Pro Glu Ile Pro Leu Ala Met Asp Arg Phe Pro Tyr Val Ala Leu
                85                  90                  95

Ser Lys Thr Tyr Asn Val Asp Lys His Val Pro Asp Ser Gly Ala Thr
            100                 105                 110

Ala Thr Ala Tyr Leu Cys Gly Val Lys Gly Asn Phe Gln Thr Ile Gly
        115                 120                 125

Leu Ser Ala Ala Ala Arg Phe Asn Gln Cys Asn Thr Thr Arg Gly Asn
    130                 135                 140

Glu Val Ile Ser Val Met Asn Arg Ala Lys Lys Ala Gly Lys Ser Val
145                 150                 155                 160

Gly Val Val Thr Thr Thr Arg Val Gln His Ala Ser Pro Ala Gly Thr
                165                 170                 175

Tyr Ala His Thr Val Asn Arg Asn Trp Tyr Ser Asp Ala Asp Val Pro
            180                 185                 190

Ala Ser Ala Arg Gln Glu Gly Cys Gln Asp Ile Ala Thr Gln Leu Ile
        195                 200                 205

Ser Asn Met Asp Ile Asp Val Ile Leu Gly Gly Gly Arg Lys Tyr Met
    210                 215                 220

Phe Pro Met Gly Thr Pro Asp Pro Glu Tyr Pro Asp Asp Tyr Ser Gln
225                 230                 235                 240
```

```
Gly Gly Thr Arg Leu Asp Gly Lys Asn Leu Val Gln Glu Trp Leu Ala
                245                 250                 255
Lys Arg Gln Gly Ala Arg Tyr Val Trp Asn Arg Thr Glu Leu Met Gln
            260                 265                 270
Ala Ser Leu Asp Pro Ser Val Thr His Leu Met Gly Leu Phe Glu Pro
        275                 280                 285
Gly Asp Met Lys Tyr Glu Ile His Arg Asp Ser Thr Leu Asp Pro Ser
    290                 295                 300
Leu Met Glu Met Thr Glu Ala Ala Leu Arg Leu Leu Ser Arg Asn Pro
305                 310                 315                 320
Arg Gly Phe Phe Leu Phe Val Glu Gly Gly Arg Ile Asp His Gly His
                325                 330                 335
His Glu Ser Arg Ala Tyr Arg Ala Leu Thr Glu Thr Ile Met Phe Asp
                340                 345                 350
Asp Ala Ile Glu Arg Ala Gly Gln Leu Thr Ser Glu Glu Asp Thr Leu
            355                 360                 365
Ser Leu Val Thr Ala Asp His Ser His Val Phe Ser Phe Gly Gly Tyr
    370                 375                 380
Pro Leu Arg Gly Ser Ser Ile Phe Gly Leu Ala Pro Gly Lys Ala Arg
385                 390                 395                 400
Asp Arg Lys Ala Tyr Thr Val Leu Leu Tyr Gly Asn Gly Pro Gly Tyr
                405                 410                 415
Val Leu Lys Asp Gly Ala Arg Pro Asp Val Thr Glu Ser Glu Ser Gly
            420                 425                 430
Ser Pro Glu Tyr Arg Gln Gln Ser Ala Val Pro Leu Asp Glu Glu Thr
        435                 440                 445
His Ala Gly Glu Asp Val Ala Val Phe Ala Arg Gly Pro Gln Ala His
    450                 455                 460
Leu Val His Gly Val Gln Glu Gln Thr Phe Ile Ala His Val Met Ala
465                 470                 475                 480
Phe Ala Ala Cys Leu Glu Pro Tyr Thr Ala Cys Asp Leu Ala Pro Pro
                485                 490                 495
Ala Gly Thr Thr Asp Ala Ala His Pro Gly Asn Tyr Glu Val Glu Pro
            500                 505                 510
Arg Arg Ala Leu Tyr Val Glu Gly Glu Arg Gly Phe Phe Tyr Thr Pro
        515                 520                 525
Lys Ala Leu Tyr Leu Val Glu Gly Glu Arg Gly Phe Phe Tyr Thr Ser
    530                 535                 540
Leu Met Thr Ile Ala Tyr Val Met Ala Ala Ile Cys Ala Leu Phe Met
545                 550                 555                 560
Leu Pro Leu Cys Leu Met Val Asp Tyr Lys Asp Asp Asp Lys
                565                 570                 575

<210> SEQ ID NO 129
<211> LENGTH: 5
<212> TYPE: PRT
<213> ORGANISM: Artificial Sequence
<220> FEATURE:
<223> OTHER INFORMATION: Description of Artificial Sequence: synthetic
      peptide sequence

<400> SEQUENCE: 129

Lys Met Asp Ala Glu
 1               5
```

```
<210> SEQ ID NO 130
<211> LENGTH: 5
<212> TYPE: PRT
<213> ORGANISM: Artificial Sequence
<220> FEATURE:
<223> OTHER INFORMATION: Description of Artificial Sequence: synthetic
      peptide sequence

<400> SEQUENCE: 130

Gly Arg Arg Gly Ser
 1               5

<210> SEQ ID NO 131
<211> LENGTH: 10
<212> TYPE: PRT
<213> ORGANISM: Artificial Sequence
<220> FEATURE:
<223> OTHER INFORMATION: Description of Artificial Sequence: synthetic
      peptide sequence

<400> SEQUENCE: 131

Val Glu Ala Asn Tyr Glu Val Glu Gly Glu
 1               5                  10

<210> SEQ ID NO 132
<211> LENGTH: 10
<212> TYPE: PRT
<213> ORGANISM: Artificial Sequence
<220> FEATURE:
<223> OTHER INFORMATION: Description of Artificial Sequence: synthetic
      peptide sequence

<400> SEQUENCE: 132

Val Glu Ala Asn Tyr Ala Val Glu Gly Glu
 1               5                  10

<210> SEQ ID NO 133
<211> LENGTH: 10
<212> TYPE: PRT
<213> ORGANISM: Artificial Sequence
<220> FEATURE:
<223> OTHER INFORMATION: Description of Artificial Sequence: synthetic
      peptide sequence

<400> SEQUENCE: 133

Lys Thr Ile Asn Leu Glu Val Glu Pro Ser
 1               5                  10

<210> SEQ ID NO 134
<211> LENGTH: 10
<212> TYPE: PRT
<213> ORGANISM: Artificial Sequence
<220> FEATURE:
<223> OTHER INFORMATION: Description of Artificial Sequence: synthetic
      peptide sequence
<220> FEATURE:
<221> NAME/KEY: MOD_RES
<222> LOCATION: (5)
<223> OTHER INFORMATION: Nle

<400> SEQUENCE: 134

Lys Thr Ile Asn Xaa Glu Val Glu Pro Ser
 1               5                  10

<210> SEQ ID NO 135
<211> LENGTH: 10
<212> TYPE: PRT
<213> ORGANISM: Artificial Sequence
<220> FEATURE:
```

```
<221> NAME/KEY: MOD_RES
<222> LOCATION: (5)
<223> OTHER INFORMATION: Nle
<220> FEATURE:
<223> OTHER INFORMATION: Description of Artificial Sequence: synthetic
      peptide sequence

<400> SEQUENCE: 135

Lys Thr Ile Asn Xaa Glu Val Asp Pro Ser
 1               5                  10

<210> SEQ ID NO 136
<211> LENGTH: 10
<212> TYPE: PRT
<213> ORGANISM: Artificial Sequence
<220> FEATURE:
<221> NAME/KEY: MOD_RES
<222> LOCATION: (5)
<223> OTHER INFORMATION: Nle
<220> FEATURE:
<223> OTHER INFORMATION: Description of Artificial Sequence: synthetic
      peptide sequence

<400> SEQUENCE: 136

Lys Thr Ile Asn Xaa Asp Val Asp Pro Ser
 1               5                  10

<210> SEQ ID NO 137
<211> LENGTH: 10
<212> TYPE: PRT
<213> ORGANISM: Artificial Sequence
<220> FEATURE:
<223> OTHER INFORMATION: Description of Artificial Sequence: synthetic
      peptide sequence

<400> SEQUENCE: 137

Lys Thr Ile Ser Leu Asp Val Glu Pro Ser
 1               5                  10

<210> SEQ ID NO 138
<211> LENGTH: 10
<212> TYPE: PRT
<213> ORGANISM: Artificial Sequence
<220> FEATURE:
<223> OTHER INFORMATION: Description of Artificial Sequence: synthetic
      peptide sequence

<400> SEQUENCE: 138

Lys Thr Ile Ser Leu Asp Val Asp Pro Ser
 1               5                  10

<210> SEQ ID NO 139
<211> LENGTH: 4
<212> TYPE: PRT
<213> ORGANISM: Artificial Sequence
<220> FEATURE:
<223> OTHER INFORMATION: Description of Artificial Sequence: synthetic
      peptide sequence

<400> SEQUENCE: 139

Lys Met Asp Ala
 1

<210> SEQ ID NO 140
<211> LENGTH: 4
<212> TYPE: PRT
<213> ORGANISM: Artificial Sequence
<220> FEATURE:
<223> OTHER INFORMATION: Description of Artificial Sequence: synthetic
```

```
                              peptide sequence

<400> SEQUENCE: 140

Ser Tyr Glu Val
  1

<210> SEQ ID NO 141
<211> LENGTH: 10
<212> TYPE: PRT
<213> ORGANISM: Artificial Sequence
<220> FEATURE:
<223> OTHER INFORMATION: Description of Artificial Sequence: synthetic
      peptide sequence

<400> SEQUENCE: 141

Ser Glu Val Ser Tyr Glu Val Glu Phe Arg
  1               5                  10

<210> SEQ ID NO 142
<211> LENGTH: 4
<212> TYPE: PRT
<213> ORGANISM: Artificial Sequence
<220> FEATURE:
<223> OTHER INFORMATION: Description of Artificial Sequence: synthetic
      peptide sequence

<400> SEQUENCE: 142

Asn Leu Asp Ala
  1

<210> SEQ ID NO 143
<211> LENGTH: 10
<212> TYPE: PRT
<213> ORGANISM: Artificial Sequence
<220> FEATURE:
<223> OTHER INFORMATION: Description of Artificial Sequence: synthetic
      peptide sequence

<400> SEQUENCE: 143

Ser Glu Val Ser Tyr Asp Ala Glu Phe Arg
  1               5                  10

<210> SEQ ID NO 144
<211> LENGTH: 10
<212> TYPE: PRT
<213> ORGANISM: Artificial Sequence
<220> FEATURE:
<223> OTHER INFORMATION: Description of Artificial Sequence: synthetic
      peptide sequence

<400> SEQUENCE: 144

Ser Glu Val Ser Tyr Glu Ala Glu Phe Arg
  1               5                  10

<210> SEQ ID NO 145
<211> LENGTH: 25
<212> TYPE: PRT
<213> ORGANISM: Artificial Sequence
<220> FEATURE:
<223> OTHER INFORMATION: Description of Artificial Sequence: synthetic
      peptide sequence

<400> SEQUENCE: 145

Thr Arg Pro Gly Ser Gly Leu Thr Asn Ile Lys Thr Glu Glu Ile Ser
  1               5                  10                  15

Glu Val Ser Tyr Glu Val Glu Phe Arg
                 20                  25
```

```
<210> SEQ ID NO 146
<211> LENGTH: 20
<212> TYPE: PRT
<213> ORGANISM: Artificial Sequence
<220> FEATURE:
<223> OTHER INFORMATION: Description of Artificial Sequence: synthetic
      peptide sequence

<400> SEQUENCE: 146

Gly Leu Thr Asn Ile Lys Thr Glu Glu Ile Ser Glu Val Ser Tyr Glu
 1               5                  10                  15

Val Glu Phe Arg
            20

<210> SEQ ID NO 147
<211> LENGTH: 15
<212> TYPE: PRT
<213> ORGANISM: Artificial Sequence
<220> FEATURE:
<223> OTHER INFORMATION: Description of Artificial Sequence: synthetic
      peptide sequence

<400> SEQUENCE: 147

Lys Thr Glu Glu Ile Ser Glu Val Ser Tyr Glu Val Glu Phe Arg
 1               5                  10                  15

<210> SEQ ID NO 148
<211> LENGTH: 10
<212> TYPE: PRT
<213> ORGANISM: Artificial Sequence
<220> FEATURE:
<223> OTHER INFORMATION: Description of Artificial Sequence: synthetic
      peptide sequence

<400> SEQUENCE: 148

Thr Glu Val Ser Tyr Glu Val Glu Phe Arg
 1               5                  10

<210> SEQ ID NO 149
<211> LENGTH: 10
<212> TYPE: PRT
<213> ORGANISM: Artificial Sequence
<220> FEATURE:
<223> OTHER INFORMATION: Description of Artificial Sequence: synthetic
      peptide sequence

<400> SEQUENCE: 149

Ser Glu Val Asp Tyr Glu Val Glu Phe Arg
 1               5                  10

<210> SEQ ID NO 150
<211> LENGTH: 10
<212> TYPE: PRT
<213> ORGANISM: Artificial Sequence
<220> FEATURE:
<223> OTHER INFORMATION: Description of Artificial Sequence: synthetic
      peptide sequence

<400> SEQUENCE: 150

Thr Glu Val Asp Tyr Glu Val Glu Phe Arg
 1               5                  10

<210> SEQ ID NO 151
<211> LENGTH: 10
<212> TYPE: PRT
<213> ORGANISM: Artificial Sequence
```

```
<220> FEATURE:
<223> OTHER INFORMATION: Description of Artificial Sequence: synthetic
      peptide sequence

<400> SEQUENCE: 151

Thr Glu Ile Asp Tyr Glu Val Glu Phe Arg
 1               5                  10

<210> SEQ ID NO 152
<211> LENGTH: 10
<212> TYPE: PRT
<213> ORGANISM: Artificial Sequence
<220> FEATURE:
<223> OTHER INFORMATION: Description of Artificial Sequence: synthetic
      peptide sequence

<400> SEQUENCE: 152

Ser Glu Ile Ser Tyr Glu Val Glu Phe Arg
 1               5                  10

<210> SEQ ID NO 153
<211> LENGTH: 10
<212> TYPE: PRT
<213> ORGANISM: Artificial Sequence
<220> FEATURE:
<223> OTHER INFORMATION: Description of Artificial Sequence: synthetic
      peptide sequence

<400> SEQUENCE: 153

Ser Glu Ile Asp Tyr Glu Val Glu Phe Arg
 1               5                  10

<210> SEQ ID NO 154
<211> LENGTH: 13
<212> TYPE: PRT
<213> ORGANISM: Artificial Sequence
<220> FEATURE:
<221> NAME/KEY: SITE
<222> LOCATION: (11)
<223> OTHER INFORMATION: Xaa=tryptophan
<220> FEATURE:
<223> OTHER INFORMATION: Description of Artificial Sequence: synthetic
      peptide sequence

<400> SEQUENCE: 154

Ser Glu Ile Ser Tyr Glu Val Glu Phe Arg Xaa Lys Lys
 1               5                  10

<210> SEQ ID NO 155
<211> LENGTH: 18
<212> TYPE: PRT
<213> ORGANISM: Artificial Sequence
<220> FEATURE:
<221> NAME/KEY: SITE
<222> LOCATION: (16)
<223> OTHER INFORMATION: Xaa=tryptophan
<220> FEATURE:
<223> OTHER INFORMATION: Description of Artificial Sequence: synthetic
      peptide sequence

<400> SEQUENCE: 155

Lys Thr Glu Glu Ile Ser Glu Ile Ser Tyr Glu Val Glu Phe Arg Xaa
 1               5                  10                  15

Lys Lys

<210> SEQ ID NO 156
<211> LENGTH: 23
<212> TYPE: PRT
```

```
<213> ORGANISM: Artificial Sequence
<220> FEATURE:
<221> NAME/KEY: SITE
<222> LOCATION: (21)
<223> OTHER INFORMATION: Xaa=tryptophan
<220> FEATURE:
<223> OTHER INFORMATION: Description of Artificial Sequence: synthetic
      peptide sequence

<400> SEQUENCE: 156

Gly Leu Thr Asn Ile Lys Thr Glu Glu Ile Ser Glu Ile Ser Tyr Glu Val
  1               5                  10                  15

Glu Phe Arg Xaa Lys Lys
         20

<210> SEQ ID NO 157
<211> LENGTH: 28
<212> TYPE: PRT
<213> ORGANISM: Artificial Sequence
<220> FEATURE:
<223> OTHER INFORMATION: Description of Artificial Sequence: synthetic
      peptide sequence
<220> FEATURE:
<221> NAME/KEY: SITE
<222> LOCATION: (26)
<223> OTHER INFORMATION: Xaa=tryptophan

<400> SEQUENCE: 157

Thr Arg Pro Gly Ser Gly Leu Thr Asn Ile Lys Thr Glu Glu Ile Ser
  1               5                  10                  15

Glu Ile Ser Tyr Glu Val Glu Phe Arg Xaa Lys Lys
                 20                  25

<210> SEQ ID NO 158
<211> LENGTH: 13
<212> TYPE: PRT
<213> ORGANISM: Artificial Sequence
<220> FEATURE:
<221> NAME/KEY: SITE
<222> LOCATION: (11)
<223> OTHER INFORMATION: Xaa=tryptophan
<220> FEATURE:
<223> OTHER INFORMATION: Description of Artificial Sequence: synthetic
      peptide sequence

<400> SEQUENCE: 158

Ser Glu Ile Ser Tyr Glu Val Glu Phe Arg Xaa Lys Lys
  1               5                  10

<210> SEQ ID NO 159
<211> LENGTH: 18
<212> TYPE: PRT
<213> ORGANISM: Artificial Sequence
<220> FEATURE:
<223> OTHER INFORMATION: Description of Artificial Sequence: synthetic
      peptide sequence
<220> FEATURE:
<221> NAME/KEY: SITE
<222> LOCATION: (16)
<223> OTHER INFORMATION: Xaa=tryptophan

<400> SEQUENCE: 159

Lys Thr Glu Glu Ile Ser Glu Ile Ser Tyr Glu Val Glu Phe Arg
  1               5                  10                  15

Xaa Lys Lys

<210> SEQ ID NO 160
<211> LENGTH: 23
```

```
<212> TYPE: PRT
<213> ORGANISM: Artificial Sequence
<220> FEATURE:
<221> NAME/KEY: SITE
<222> LOCATION: (21)
<223> OTHER INFORMATION: Xaa=tryptophan
<220> FEATURE:
<223> OTHER INFORMATION: Description of Artificial Sequence: synthetic
      peptide

<400> SEQUENCE: 160

Gly Leu Thr Asn Ile Lys Thr Glu Glu Ile Ser Glu Ile Ser Tyr
 1               5                  10                  15

Glu Val Glu Phe Arg Xaa Lys Lys
                20

<210> SEQ ID NO 161
<211> LENGTH: 28
<212> TYPE: PRT
<213> ORGANISM: Artificial Sequence
<220> FEATURE:
<221> NAME/KEY: SITE
<222> LOCATION: (26)
<223> OTHER INFORMATION: Xaa=tryptophan
<220> FEATURE:
<223> OTHER INFORMATION: Description of Artificial Sequence: synthetic
      peptide sequence

<400> SEQUENCE: 161

Thr Arg Pro Gly Ser Gly Leu Thr Asn Ile Lys Thr Glu Glu Ile
 1               5                  10                  15

Ser Glu Ile Ser Tyr Glu Val Glu Phe Arg Xaa Lys Lys
                20                  25

<210> SEQ ID NO 162
<211> LENGTH: 13
<212> TYPE: PRT
<213> ORGANISM: Artificial Sequence
<220> FEATURE:
<221> NAME/KEY: SITE
<222> LOCATION: (11)
<223> OTHER INFORMATION: Xaa=oregon green
<220> FEATURE:
<223> OTHER INFORMATION: Description of Artificial Sequence: synthetic
      peptide sequence

<400> SEQUENCE: 162

Ser Glu Ile Ser Tyr Glu Val Glu Phe Arg Xaa Lys Lys
 1               5                  10

<210> SEQ ID NO 163
<211> LENGTH: 18
<212> TYPE: PRT
<213> ORGANISM: Artificial Sequence
<220> FEATURE:
<221> NAME/KEY: SITE
<222> LOCATION: (16)
<223> OTHER INFORMATION: Xaa=oregon green
<220> FEATURE:
<223> OTHER INFORMATION: Description of Artificial Sequence: synthetic
      peptide sequence

<400> SEQUENCE: 163

Lys Thr Glu Glu Ile Ser Glu Ile Ser Tyr Glu Val Glu Phe Arg Xaa
 1               5                  10                  15

Lys Lys

<210> SEQ ID NO 164
```

```
<211> LENGTH: 23
<212> TYPE: PRT
<213> ORGANISM: Artificial Sequence
<220> FEATURE:
<221> NAME/KEY: SITE
<222> LOCATION: (21)
<223> OTHER INFORMATION: Xaa=oregon green
<220> FEATURE:
<223> OTHER INFORMATION: Description of Artificial Sequence: synthetic
      peptide sequence

<400> SEQUENCE: 164

Gly Leu Thr Asn Ile Lys Thr Glu Glu Ile Ser Glu Ile Ser Tyr Glu
 1               5                  10                  15

Val Glu Phe Arg Xaa Lys Lys
            20

<210> SEQ ID NO 165
<211> LENGTH: 28
<212> TYPE: PRT
<213> ORGANISM: Artificial Sequence
<220> FEATURE:
<221> NAME/KEY: SITE
<222> LOCATION: (26)
<223> OTHER INFORMATION: Xaa=oregon green
<220> FEATURE:
<223> OTHER INFORMATION: Description of Artificial Sequence: synthetic
      peptide sequence

<400> SEQUENCE: 165

Thr Arg Pro Gly Ser Gly Leu Thr Asn Ile Lys Thr Glu Glu Ile Ser
 1               5                  10                  15

Glu Ile Ser Tyr Glu Val Glu Phe Arg Xaa Lys Lys
            20                  25

<210> SEQ ID NO 166
<211> LENGTH: 13
<212> TYPE: PRT
<213> ORGANISM: Artificial Sequence
<220> FEATURE:
<221> NAME/KEY: SITE
<222> LOCATION: (11)
<223> OTHER INFORMATION: Xaa=oregon green
<220> FEATURE:
<223> OTHER INFORMATION: Description of Artificial Sequence: synthetic
      peptide sequence

<400> SEQUENCE: 166

Ser Glu Ile Ser Tyr Glu Val Glu Phe Arg Xaa Lys Lys
 1               5                  10

<210> SEQ ID NO 167
<211> LENGTH: 18
<212> TYPE: PRT
<213> ORGANISM: Artificial Sequence
<220> FEATURE:
<221> NAME/KEY: SITE
<222> LOCATION: (16)
<223> OTHER INFORMATION: Xaa=oregon green
<220> FEATURE:
<223> OTHER INFORMATION: Description of Artificial Sequence: synthetic
      peptide sequence

<400> SEQUENCE: 167

Lys Thr Glu Glu Ile Ser Glu Ile Ser Tyr Glu Val Glu Phe Arg
 1               5                  10                  15

Xaa Lys Lys
```

<210> SEQ ID NO 168
<211> LENGTH: 23
<212> TYPE: PRT
<213> ORGANISM: Artificial Sequence
<220> FEATURE:
<221> NAME/KEY: SITE
<222> LOCATION: (21)
<223> OTHER INFORMATION: Xaa=oregon green
<220> FEATURE:
<223> OTHER INFORMATION: Description of Artificial Sequence: synthetic peptide sequence

<400> SEQUENCE: 168

Gly Leu Thr Asn Ile Lys Thr Glu Glu Ile Ser Glu Ile Ser Tyr
 1               5                  10                  15
Glu Val Glu Phe Arg Xaa Lys Lys
                 20

<210> SEQ ID NO 169
<211> LENGTH: 28
<212> TYPE: PRT
<213> ORGANISM: Artificial Sequence
<220> FEATURE:
<221> NAME/KEY: SITE
<222> LOCATION: (26)
<223> OTHER INFORMATION: Xaa=oregon green
<220> FEATURE:
<223> OTHER INFORMATION: Description of Artificial Sequence: synthetic peptide sequence

<400> SEQUENCE: 169

Thr Arg Pro Gly Ser Gly Leu Thr Asn Ile Lys Thr Glu Glu Ile
 1               5                  10                  15
Ser Glu Ile Ser Tyr Glu Val Glu Phe Arg Xaa Lys Lys
                 20                  25

<210> SEQ ID NO 170
<211> LENGTH: 10
<212> TYPE: PRT
<213> ORGANISM: Artificial Sequence
<220> FEATURE:
<223> OTHER INFORMATION: Description of Artificial Sequence: synthetic peptide sequence

<400> SEQUENCE: 170

Ser Glu Val Asn Tyr Glu Val Glu Phe Arg
 1               5                  10

<210> SEQ ID NO 171
<211> LENGTH: 47
<212> TYPE: DNA
<213> ORGANISM: Artificial Sequence
<220> FEATURE:
<223> OTHER INFORMATION: Description of Artificial Sequence: synthetic primer for site-directed mutagenesis of APP

<400> SEQUENCE: 171
gagatctctg aaattagtta tgaagtagaa ttccgacatg actcagg       47

<210> SEQ ID NO 172
<211> LENGTH: 48
<212> TYPE: DNA
<213> ORGANISM: Artificial Sequence
<220> FEATURE:
<223> OTHER INFORMATION: Description of Artificial Sequence: synthetic primer for site-directed mutagenesis of APP

<400> SEQUENCE: 172

-continued

```
tgagtcatgt cggaattcta cttcataact aatttcagag atctcctc        48
```

<210> SEQ ID NO 173
<211> LENGTH: 47
<212> TYPE: DNA
<213> ORGANISM: Artificial Sequence
<220> FEATURE:
<223> OTHER INFORMATION: Description of Artificial Sequence: synthetic
      primer for site-directed mutagenesis of APP

<400> SEQUENCE: 173

```
gagatctctg aaagtagtta tgaagtagaa ttccgacatg actcagg        47
```

<210> SEQ ID NO 174
<211> LENGTH: 48
<212> TYPE: DNA
<213> ORGANISM: Artificial Sequence
<220> FEATURE:
<223> OTHER INFORMATION: Description of Artificial Sequence: synthetic
      primer for site-directed mutagenesis of APP

<400> SEQUENCE: 174

```
tgagtcatgt cggaattcta cttcataact actttcagag atctcctc        48
```

<210> SEQ ID NO 175
<211> LENGTH: 47
<212> TYPE: DNA
<213> ORGANISM: Artificial Sequence
<220> FEATURE:
<223> OTHER INFORMATION: Description of Artificial Sequence: synthetic
      primer for site-directed mutagenesis of APP

<400> SEQUENCE: 175

```
gagatctctg aaattagtta tgaagcagaa ttccgacatg actcagg        47
```

<210> SEQ ID NO 176
<211> LENGTH: 48
<212> TYPE: DNA
<213> ORGANISM: Artificial Sequence
<220> FEATURE:
<223> OTHER INFORMATION: Description of Artificial Sequence: synthetic
      primer for site-directed mutagenesis of APP

<400> SEQUENCE: 176

```
tgagtcatgt cggaattctg cttcataact aatttcagag atctcctc        48
```

<210> SEQ ID NO 177
<211> LENGTH: 5
<212> TYPE: PRT
<213> ORGANISM: Artificial Sequence
<220> FEATURE:
<223> OTHER INFORMATION: Description of Artificial Sequence: synthetic
      peptide sequence

<400> SEQUENCE: 177

Val Ser Tyr Glu Val
 1               5

<210> SEQ ID NO 178
<211> LENGTH: 5
<212> TYPE: PRT
<213> ORGANISM: Artificial Sequence
<220> FEATURE:
<223> OTHER INFORMATION: Description of Artificial Sequence: synthetic
      peptide sequence

<400> SEQUENCE: 178

Val Ser Tyr Asp Ala
1               5

<210> SEQ ID NO 179
<211> LENGTH: 5
<212> TYPE: PRT
<213> ORGANISM: Artificial Sequence
<220> FEATURE:
<223> OTHER INFORMATION: Description of Artificial Sequence: synthetic
      peptide sequence

<400> SEQUENCE: 179

Ile Ser Tyr Glu Val
1               5

<210> SEQ ID NO 180
<211> LENGTH: 5
<212> TYPE: PRT
<213> ORGANISM: Artificial Sequence
<220> FEATURE:
<223> OTHER INFORMATION: Description of Artificial Sequence: synthetic
      peptide sequence

<400> SEQUENCE: 180

Val Lys Met Asp Ala
1               5

<210> SEQ ID NO 181
<211> LENGTH: 47
<212> TYPE: DNA
<213> ORGANISM: Artificial Sequence
<220> FEATURE:
<223> OTHER INFORMATION: Description of Artificial Sequence: synthetic
      primer for generating mutant construct named
      MBPC125-SYEV

<400> SEQUENCE: 181
gacatctctg aagtgagtta ttaggcagaa ttccgacatg actcagg                47

<210> SEQ ID NO 182
<211> LENGTH: 48
<212> TYPE: DNA
<213> ORGANISM: Artificial Sequence
<220> FEATURE:
<223> OTHER INFORMATION: Description of Artificial Sequence: synthetic
      primer for generating mutant construct named
      MBPC125-SYEV

<400> SEQUENCE: 182
tgagtcatgt cggaattctg cctaataact cacttcagag atctcctc                48

<210> SEQ ID NO 183
<211> LENGTH: 6
<212> TYPE: PRT
<213> ORGANISM: Artificial Sequence
<220> FEATURE:
<223> OTHER INFORMATION: Description of Artificial Sequence: synthetic
      peptide sequence

<400> SEQUENCE: 183

Lys Lys Ser Tyr Glu Val
1               5

<210> SEQ ID NO 184
<211> LENGTH: 10
<212> TYPE: PRT
<213> ORGANISM: Artificial Sequence
<220> FEATURE:

```
<223> OTHER INFORMATION: Description of Artificial Sequence: synthetic
      peptide sequence

<400> SEQUENCE: 184

Val Glu Ala Asn Tyr Glu Val Glu Gly Glu
  1               5                  10

<210> SEQ ID NO 185
<211> LENGTH: 10
<212> TYPE: PRT
<213> ORGANISM: Artificial Sequence
<220> FEATURE:
<223> OTHER INFORMATION: Description of Artificial Sequence: synthetic
      peptide sequence

<400> SEQUENCE: 185

Val Glu Ala Asn Tyr Ala Val Glu Gly Glu
  1               5                  10

<210> SEQ ID NO 186
<211> LENGTH: 8
<212> TYPE: PRT
<213> ORGANISM: Artificial Sequence
<220> FEATURE:
<223> OTHER INFORMATION: Description of Artificial Sequence: synthetic
      peptide sequence

<400> SEQUENCE: 186

Asp Tyr Lys Asp Asp Asp Asp Lys
  1               5

<210> SEQ ID NO 187
<211> LENGTH: 4
<212> TYPE: PRT
<213> ORGANISM: Artificial Sequence
<220> FEATURE:
<223> OTHER INFORMATION: Description of Artificial Sequence: synthetic
      peptide sequence

<400> SEQUENCE: 187

Ser Tyr Glu Ala
  1

<210> SEQ ID NO 188
<211> LENGTH: 4
<212> TYPE: PRT
<213> ORGANISM: Artificial Sequence
<220> FEATURE:
<223> OTHER INFORMATION: Description of Artificial Sequence: synthetic
      peptide sequence

<400> SEQUENCE: 188

Ser Tyr Ala Val
  1

<210> SEQ ID NO 189
<211> LENGTH: 5
<212> TYPE: PRT
<213> ORGANISM: Artificial Sequence
<220> FEATURE:
<223> OTHER INFORMATION: Description of Artificial Sequence: synthetic
      peptide sequence

<400> SEQUENCE: 189

Val Ser Tyr Glu Ala
  1               5
```

```
<210> SEQ ID NO 190
<211> LENGTH: 13
<212> TYPE: PRT
<213> ORGANISM: Artificial sequence
<220> FEATURE:
<223> OTHER INFORMATION: Description of artificial sequence: synthetic
      peptide sequence

<400> SEQUENCE: 190

Ser Glu Ile Ser Tyr Glu Val Glu Phe Arg Trp Lys Lys
1               5                   10

<210> SEQ ID NO 191
<211> LENGTH: 23
<212> TYPE: PRT
<213> ORGANISM: Artificial sequence
<220> FEATURE:
<223> OTHER INFORMATION: Description of artificial sequence: synthetic
      peptide sequence

<400> SEQUENCE: 191

Gly Leu Thr Asn Ile Lys Thr Glu Glu Ile Ser Glu Ile Ser Tyr Glu
1               5                   10                  15

Val Glu Phe Arg Trp Lys Lys
            20

<210> SEQ ID NO 192
<211> LENGTH: 15
<212> TYPE: PRT
<213> ORGANISM: Artificial sequence
<220> FEATURE:
<223> OTHER INFORMATION: Description of artificial sequence: synthetic
      peptide sequence
<220> FEATURE:
<221> NAME/KEY: SITE
<222> LOCATION: (1)..(1)
<223> OTHER INFORMATION: amino acid at position 1 is biotinylated
<220> FEATURE:
<221> NAME/KEY: SITE
<222> LOCATION: (14)..(14)
<223> OTHER INFORMATION: cys at position 14 is derivatized with an
      oregon green

<400> SEQUENCE: 192

Lys Glu Ile Ser Glu Ile Ser Tyr Glu Val Glu Phe Arg Lys Lys
1               5                   10                  15

<210> SEQ ID NO 193
<211> LENGTH: 22
<212> TYPE: PRT
<213> ORGANISM: Artificial sequence
<220> FEATURE:
<223> OTHER INFORMATION: Description of artificial sequence: synthetic
      peptide sequence
<220> FEATURE:
<221> NAME/KEY: SITE
<222> LOCATION: (1)..(1)
<223> OTHER INFORMATION: amino acid at position 1 is biotinylated
<220> FEATURE:
<221> NAME/KEY: SITE
<222> LOCATION: (21)..(21)
<223> OTHER INFORMATION: cys at position 21 is derivatized with an
      oregon green

<400> SEQUENCE: 193

Gly Leu Thr Asn Ile Lys Thr Glu Glu Ile Ser Glu Ile Ser Tyr Glu
1               5                   10                  15

Val Glu Phe Arg Lys Lys
            20
```

<210> SEQ ID NO 194
<211> LENGTH: 6806
<212> TYPE: DNA
<213> ORGANISM: Artificial sequence
<220> FEATURE:
<223> OTHER INFORMATION: Description of artificial sequence: synthetic
DNA sequence

<400> SEQUENCE: 194

| | |
|---|---|
| ccgacaccat cgaatggcgc aaaacctttc gcggtatggc atgatagcgc ccggaagaga | 60 |
| gtcaattcag ggtggtgaat gtgaaaccag taacgttata cgatgtcgca gagtatgccg | 120 |
| gtgtctctta tcagaccgtt tcccgcgtgg tgaaccaggc cagccacgtt tctgcgaaaa | 180 |
| cgcgggaaaa agtggaagcg gcgatggcgg agctgaatta cattcccaac cgcgtggcac | 240 |
| aacaactggc gggcaaacag tcgttgctga ttggcgttgc cacctccagt ctggccctgc | 300 |
| acgcgccgtc gcaaattgtc gcggcgatta atctcgcgc cgatcaactg ggtgccagcg | 360 |
| tggtggtgtc gatggtagaa cgaagcggcg tcgaagcctg taaagcggcg gtgcacaatc | 420 |
| ttctcgcgca acgcgtcagt gggctgatca ttaactatcc gctggatgac caggatgcca | 480 |
| ttgctgtgga agctgcctgc actaatgttc cggcgttatt tcttgatgtc tctgaccaga | 540 |
| cacccatcaa cagtattatt ttctcccatg aagacggtac gcgactgggc gtggagcatc | 600 |
| tggtcgcatt gggtcaccag caaatcgcgc tgttagcggg cccattaagt tctgtctcgg | 660 |
| cgcgtctgcg tctggctggc tggcataaat atctcactcg caatcaaatt cagccgatag | 720 |
| cggaacggga aggcgactgg agtgccatgt ccggttttca acaaaccatg caaatgctga | 780 |
| atgagggcat cgttcccact gcgatgctgg ttgccaacga tcagatggcg ctgggcgcaa | 840 |
| tgcgcgccat taccgagtcc gggctgcgcg ttggtgcgga tatctcggta gtgggatacg | 900 |
| acgataccga agacagctca tgttatatcc gccgttaac caccatcaaa caggattttc | 960 |
| gcctgctggg gcaaaccagc gtggaccgct tgctgcaact ctctcagggc caggcggtga | 1020 |
| agggcaatca gctgttgccc gtctcactgg tgaaaagaaa aaccacccctg cgcccaata | 1080 |
| cgcaaaccgc ctctccccgc gcgttggccg attcattaat gcagctggca cgacaggttt | 1140 |
| cccgactgga aagcgggcag tgagcgcaac gcaattaatg tgagttagct cactcattag | 1200 |
| gcacaattct catgtttgac agcttatcat cgactgcacg gtgcaccaat gcttctggcg | 1260 |
| tcaggcagcc atcggaagct gtggtatggc tgtgcaggtc gtaaatcact gcataattcg | 1320 |
| tgtcgctcaa ggcgcactcc cgttctggat aatgtttttt gcgccgacat cataacggtt | 1380 |
| ctggcaaata ttctgaaatg agctgttgac aattaatcat cggctcgtat aatgtgtgga | 1440 |
| attgtgagcg gataacaatt tcacacagga aacagccagt ccgtttaggt gttttcacga | 1500 |
| gcacttcacc aacaaggacc atagattatg aaaactgaag aaggtaaact ggtaatctgg | 1560 |
| attaacggcg ataaaggcta taacggtctc gctgaagtcg gtaagaaatt cgagaaagat | 1620 |
| accggaatta aagtcaccgt tgagcatccg gataaactgg aagagaaatt cccacaggtt | 1680 |
| gcggcaactg gcgatggccc tgacattatc ttctgggcac acgaccgctt ggtggctac | 1740 |
| gctcaatctg gcctgttggc tgaaatcacc ccggacaaag cgttccagga caagctgtat | 1800 |
| ccgtttacct gggatgccgt acgttacaac ggcaagctga ttgcttaccc gatcgctgtt | 1860 |
| gaagcgttat cgctgattta taacaaagat ctgctgccga acccgccaaa aacctgggaa | 1920 |
| gagatcccgg cgctggataa agaactgaaa gcgaaggta agagcgcgct gatgttcaac | 1980 |
| ctgcaagaac cgtacttcac ctggccgctg attgctgctg acgggggtta tgcgttcaag | 2040 |

-continued

```
tatgaaaacg gcaagtacga cattaaagac gtgggcgtgg ataacgctgg cgcgaaagcg    2100
ggtctgacct tcctggttga cctgattaaa aacaaacaca tgaatgcaga caccgattac    2160
tccatcgcag aagctgcctt taataaaggc gaaacagcga tgaccatcaa cggcccgtgg    2220
gcatggtcca acatcgacac cagcaaagtg aattatggtg taacggtact gccgaccttc    2280
aagggtcaac catccaaacc gttcgttggc gtgctgagcg caggtattaa cgccgccagt    2340
ccgaacaaag agctggcgaa agagttcctc gaaaactatc tgctgactga tgaaggtctg    2400
gaagcggtta ataaagacaa accgctgggt gccgtagcgc tgaagtctta cgaggaagag    2460
ttggcgaaag atccacgtat tgccgccacc atggaaaacg cccagaaagg tgaaatcatg    2520
ccgaacatcc cgcagatgtc cgctttctgg tatgccgtgc gtactgcggt gatcaacgcc    2580
gccagcggtc gtcagactgt cgatgaagcc ctgaaagacg cgcagactaa ttcgagctcg    2640
gtacccggcc ggggatccat cgagggtagg gccgaccgag gactgaccac tcgaccaggt    2700
tctgggttga caaatatcaa gacggaggag atctctgaag tgaatctgga tgcagaattc    2760
cgacatgact caggatatga agttcatcat caaaaattgg tgttctttgc agaagatgtg    2820
ggttcaaaca aagtgcaat cattggactc atggtgggcg tgttgtcat agcgacagtg    2880 atcgtcatca ccttggtgat gctgaagaag aaacagtaca catccattca tcatggtgtg    2940
gtggaggttg acgccgctgt caccccagag gagcgccacc tgtccaagat gcagcagaac    3000
ggctacgaaa atccaaccta caagttcttt gagcagatgc agaactagac ccccgccaca    3060
gcagcctctg aagttggaca gcaaaaccat tgcttcacta cccatcggtg tccatttata    3120
gaataatgtg ggaagaaaca aacccgtttt atgatttact cattatcgcc ttttgacagc    3180
tgtgctgtaa cacaagtaga tgcctgaact tgaattaatc cacacatcag taatgtattc    3240
tatctctctt tacattttgg tctctatact acattattaa tgggttttgt gtactgtaaa    3300
gaatttagct gtatcaaact agtaatagcc tgaattcagt aacctaaccc tcgatggatc    3360
ctctagagtc gacctgcagg caagcttggc actggccgtc gttttacaac gtcgtgactg    3420
ggaaaaccct ggcgttaccc aacttaatcg ccttgcagca catccccctt tcgccagctg    3480
gcgtaatagc gaagaggccc gcaccgatcg cccttcccaa cagttgcgca gcctgaatgg    3540
cgaatggcag cttggctgtt ttggcggatg agagaagatt ttcagcctga tacagattaa    3600
atcagaacgc agaagcggtc tgataaaaca gaatttgcct ggcggcagta gcgcggtggt    3660
cccacctgac cccatgccga actcagaagt gaaacgccgt agcgccgatg gtagtgtggg    3720
gtctccccat gcgagagtag ggaactgcca ggcatcaaat aaaacgaaag gctcagtcga    3780
aagactgggc ctttcgtttt atctgttgtt tgtcggtgaa cgctctcctg agtaggacaa    3840
atccgccggg agcggatttg aacgttgcga agcaacggcc cggagggtgg cgggcaggac    3900
gcccgccata aactgccagg catcaaatta agcagaaggc catcctgacg gatggccttt    3960
ttgcgtttct acaaactctt tttgtttatt tttctaaata cattcaaata tgtatccgct    4020
catgagacaa taaccctgat aaatgcttca ataatattga aaaggaaga gtatgagtat    4080 tcaacatttc cgtgtcgccc ttattccctt ttttgcggca ttttgccttc ctgtttttgc    4140
tcacccagaa acgctggtga agtaaaaga tgctgaagat cagttgggtg cacgagtggg    4200
ttacatcgaa ctggatctca acagcggtaa gatccttgag agttttcgcc ccgaagaacg    4260
ttttccaatg atgagcactt ttaaagttct gctatgtggc gcggtattat cccgtgttga    4320
cgccgggcaa gagcaactcg gtcgccgcat acactattct cagaatgact tggttgagta    4380
ctcaccagtc acagaaaagc atcttacgga tggcatgaca gtaagagaat tatgcagtgc    4440
```

```
tgccataacc atgagtgata acactgcggc caacttactt ctgacaacga tcggaggacc    4500
gaaggagcta accgcttttt tgcacaacat gggggatcat gtaactcgcc ttgatcgttg    4560
ggaaccggag ctgaatgaag ccataccaaa cgacgagcgt gacaccacga tgcctgtagc    4620
aatggcaaca acgttgcgca aactattaac tggcgaacta cttactctag cttcccggca    4680
acaattaata gactggatgg aggcggataa agttgcagga ccacttctgc gctcggccct    4740
tccggctggc tggtttattg ctgataaatc tggagccggt gagcgtgggt ctcgcggtat    4800
cattgcagca ctggggccag atggtaagcc ctcccgtatc gtagttatct acacgacggg    4860
gagtcaggca actatggatg aacgaaatag acagatcgct gagataggtg cctcactgat    4920
taagcattgg taactgtcag accaagttta ctcatatata ctttagattg atttaaaact    4980 tcattttaa tttaaaagga tctaggtgaa gatcctttt gataatctca tgaccaaaat    5040
cccttaacgt gagttttcgt tccactgagc gtcagacccc gtagaaaaga tcaaaggatc    5100
ttcttgagat cctttttttc tgcgcgtaat ctgctgcttg caaacaaaaa aaccaccgct    5160
accagcggtg gtttgtttgc cggatcaaga gctaccaact cttttccga aggtaactgg    5220 cttcagcaga gcgcagatac caaatactgt ccttctagtg tagccgtagt taggccacca    5280
cttcaagaac tctgtagcac cgcctacata cctcgctctg ctaatcctgt taccagtggc    5340
tgctgccagt ggcgataagt cgtgtcttac cgggttggac tcaagacgat agttaccgga    5400
taaggcgcag cggtcgggct gaacgggggg ttcgtgcaca cagcccagct tggagcgaac    5460
gacctacacc gaactgagat acctacagcg tgagctatga gaaagcgcca cgcttcccga    5520
agggagaaag gcggacaggt atccggtaag cggcagggtc ggaacaggag agcgcacgag    5580
ggagcttcca gggggaaacg cctggtatct ttatagtcct gtcgggtttc gccacctctg    5640
acttgagcgt cgatttttgt gatgctcgtc aggggggcgg agcctatgga aaaacgccag    5700
caacgcggcc ttttacggt tcctggcctt ttgctggcct tttgctcaca tgttctttcc    5760
tgcgttatcc cctgattctg tggataaccg tattaccgcc tttgagtgag ctgataccgc    5820
tcgccgcagc cgaacgaccg agcgcagcga gtcagtgagc gaggaagcgg aagagcgcct    5880
gatgcggtat tttctcctta cgcatctgtg cggtatttca caccgcatat ggtgcactct    5940
cagtacaatc tgctctgatg ccgcatagtt aagccagtat acactccgct atcgctacgt    6000
gactgggtca tggctgcgcc ccgacacccg ccaacacccg ctgacgcgcc ctgacgggct    6060
tgtctgctcc cggcatccgc ttacagacaa gctgtgaccg tctccgggag ctgcatgtgt    6120
cagaggtttt caccgtcatc accgaaacgc gcgaggcagc tgcggtaaag ctcatcagcg    6180
tggtcgtgaa gcgattcaca gatgtctgcc tgttcatccg cgtccagctc gttgagtttc    6240
tccagaagcg ttaatgtctg gcttctgata aagcgggcca tgttaagggc ggttttttcc    6300
tgtttggtca cttgatgcct ccgtgtaagg gggaatttct gttcatgggg gtaatgatac    6360
cgatgaaacg agagaggatg ctcacgatac gggttactga tgatgaacat gcccggttac    6420
tggaacgttg tgagggtaaa caactggcgg tatggatgcg gcgggaccag agaaaaatca    6480
ctcagggtca atgccagcgc ttcgttaata cagatgtagg tgttccacag ggtagccagc    6540
agcatcctgc gatgcagatc cggaacataa tggtgcaggg cgctgacttc cgcgtttcca    6600
gactttacga aacacggaaa ccgaagacca ttcatgttgt tgctcaggtc gcagacgttt    6660
tgcagcagca gtcgcttcac gttcgctcgc gtatcggtga ttcattctgc taaccagtaa    6720
ggcaaccccg ccagcctagc cgggtcctca acgacaggag cacgatcatg cgcacccgtg    6780
```

```
gccaggaccc aacgctgccc gaaatt                                         6806
```

<210> SEQ ID NO 195
<211> LENGTH: 13
<212> TYPE: PRT
<213> ORGANISM: Artificial sequence
<220> FEATURE:
<223> OTHER INFORMATION: Description of artificial sequence: synthetic
      peptide sequence
<220> FEATURE:
<221> NAME/KEY: MOD_RES
<222> LOCATION: (1)..(1)
<223> OTHER INFORMATION: ACETYLATION (MCA)
<220> FEATURE:
<221> NAME/KEY: SITE
<222> LOCATION: (11)..(11)
<223> OTHER INFORMATION: 2,4-dinitrophenyl group after the Lys at
      position 11

<400> SEQUENCE: 195

Ser Glu Val Asn Leu Asp Ala Glu Phe Arg Lys Arg Arg
1               5                   10

<210> SEQ ID NO 196
<211> LENGTH: 12
<212> TYPE: PRT
<213> ORGANISM: Artificial sequence
<220> FEATURE:
<223> OTHER INFORMATION: Description of artificial sequence: synthetic
      peptide sequence
<220> FEATURE:
<221> NAME/KEY: SITE
<222> LOCATION: (4)..(4)
<223> OTHER INFORMATION: amino acid at position 4 has been derivatized
      with a statine

<400> SEQUENCE: 196

Ser Glu Val Asn Val Ala Glu Phe Arg Gly Gly Cys
1               5                   10

<210> SEQ ID NO 197
<211> LENGTH: 10
<212> TYPE: PRT
<213> ORGANISM: synthetic peptide sequence
<220> FEATURE:
<221> NAME/KEY: SITE
<222> LOCATION: (4)..(4)
<223> OTHER INFORMATION: amino acid at position 4 has been derivatized
      with a statine
<220> FEATURE:
<221> NAME/KEY: SITE
<222> LOCATION: (10)..(10)
<223> OTHER INFORMATION: amino acid at position 10 has been derivatized
      with Bodipy FL

<400> SEQUENCE: 197

Ser Glu Val Asn Val Ala Glu Phe Arg Cys
1               5                   10

<210> SEQ ID NO 198
<211> LENGTH: 2043
<212> TYPE: DNA
<213> ORGANISM: Mus musculus

<400> SEQUENCE: 198

```
atggcccag cgctgcactg gctcctgcta tgggtgggct cgggaatgct gcctgcccag      60
ggaacccatc tcggcatccg gctgccccett cgcagcggcc tggcagggcc acccctgggc   120
ctgaggctgc cccgggagac tgacgaggaa tcggaggagc tggccggag aggcagctt      180
```

```
gtggagatgg tggacaacct gaggggaaag tccggccagg gctactatgt ggagatgacc    240
gtaggcagcc ccccacagac gctcaacatc ctggtggaca cgggcagtag taactttgca    300 gtggggctg ccccacaccc tttcctgcat cgctactacc agaggcagct gtccagcaca    360
tatcgagacc tccgaaaggg tgtgtatgtg ccctacaccc agggcaagtg ggaggggaa    420 ctgggcaccg acctggtgag catccctcat ggccccaacg tcactgtgcg tgccaacatt    480
gctgccatca ctgaatcgga caagttcttc atcaatggtt ccaactggga gggcatccta    540
gggctggcct atgctgagat tgccaggccc gacgactctt tggagccctt ctttgactcc    600
ctggtgaagc agacccacat tcccaacatc ttttccctgc agctctgtgg cgctggcttc    660
cccctcaacc agaccgaggc actggcctcg gtgggaggga gcatgatcat tggtggtatc    720
gaccactcgc tatacacggg cagtctctgg tacacaccca tccggcggga gtggtattat    780
gaagtgatca ttgtacgtgt ggaaatcaat ggtcaagatc tcaagatgga ctgcaaggag    840
tacaactacg acaagagcat tgtggacagt gggaccacca accttcgctt gcccaagaaa    900
gtatttgaag ctgccgtcaa gtccatcaag gcagcctcct cgacggagaa gttcccggat    960
ggcttttggc taggggagca gctggtgtgc tggcaagcag gcacgacccc ttggaacatt   1020
ttcccagtca tttcacttta cctcatgggt gaagtcacca atcagtcctt ccgcatcacc   1080
atccttcctc agcaatacct acggccggtg gaggacgtgg ccacgtccca agacgactgt   1140
tacaagttcg ctgtctcaca gtcatccacg ggcactgtta tgggagccgt catcatggaa   1200
ggtttctatg tcgtcttcga tcgagcccga aagcgaattg ctttgctgt cagcgcttgc   1260 catgtgcacg atgagttcag gacggcggca gtggaaggtc cgtttgttac ggcagacatg   1320
gaagactgtg gctacaacat tccccagaca gatgagtcaa cacttatgac catagcctat   1380
gtcatggcgg ccatctgcgc cctcttcatg ttgccactct gcctcatggt atgtcagtgg   1440
cgctgcctgc gttgcctgcg ccaccagcac gatgactttg ctgatgacat ctccctgctc   1500
aagtaaggag gctcgtgggc agatgatgga gacgccctg gaccacatct gggtggttcc   1560
ctttggtcac atgagttgga gctatggatg gtacctgtgg ccagagcacc tcaggaccct   1620
caccaacctg ccaatgcttc tggcgtgaca gaacagagaa atcaggcaag ctggattaca   1680
gggcttgcac ctgtaggaca caggagaggg aaggaagcag cgttctggtg caggaatat    1740 ccttaggcac cacaaacttg agttggaaat tttgctgctt gaagcttcag ccctgaccct   1800
ctgcccagca tcctttagag tctccaacct aaagtattct ttatgtcctt ccagaagtac   1860
tggcgtcata ctcaggctac ccggcatgtg tccctgtggt accctggcag agaaagggcc   1920
aatctcattc cctgctggcc aaagtcagca gaagaaggtg aagtttgcca gttgctttag   1980
tgatagggac tgcagactca agcctacact ggtacaaaga ctgcgtcttg agataaacaa   2040
gaa                                                                  2043
```

<210> SEQ ID NO 199
<211> LENGTH: 501
<212> TYPE: PRT
<213> ORGANISM: Mus musculus

<400> SEQUENCE: 199

```
Met Ala Pro Ala Leu His Trp Leu Leu Leu Trp Val Gly Ser Gly Met
1               5                   10                  15

Leu Pro Ala Gln Gly Thr His Leu Gly Ile Arg Leu Pro Leu Arg Ser
            20                  25                  30

Gly Leu Ala Gly Pro Pro Leu Gly Leu Arg Leu Pro Arg Glu Thr Asp
```

-continued

```
            35                  40                  45
Glu Glu Ser Glu Glu Pro Gly Arg Arg Gly Ser Phe Val Glu Met Val
 50                  55                  60

Asp Asn Leu Arg Gly Lys Ser Gly Gln Gly Tyr Tyr Val Glu Met Thr
 65                  70                  75                  80

Val Gly Ser Pro Pro Gln Thr Leu Asn Ile Leu Val Asp Thr Gly Ser
                 85                  90                  95

Ser Asn Phe Ala Val Gly Ala Ala Pro His Pro Phe Leu His Arg Tyr
                100                 105                 110

Tyr Gln Arg Gln Leu Ser Ser Thr Tyr Arg Asp Leu Arg Lys Gly Val
                115                 120                 125

Tyr Val Pro Tyr Thr Gln Gly Lys Trp Glu Gly Glu Leu Gly Thr Asp
            130                 135                 140

Leu Val Ser Ile Pro His Gly Pro Asn Val Thr Val Arg Ala Asn Ile
145                 150                 155                 160

Ala Ala Ile Thr Glu Ser Asp Lys Phe Phe Ile Asn Gly Ser Asn Trp
                165                 170                 175

Glu Gly Ile Leu Gly Leu Ala Tyr Ala Glu Ile Ala Arg Pro Asp Asp
            180                 185                 190

Ser Leu Glu Pro Phe Phe Asp Ser Leu Val Lys Gln Thr His Ile Pro
            195                 200                 205

Asn Ile Phe Ser Leu Gln Leu Cys Gly Ala Gly Phe Pro Leu Asn Gln
210                 215                 220

Thr Glu Ala Leu Ala Ser Val Gly Gly Ser Met Ile Ile Gly Gly Ile
225                 230                 235                 240

Asp His Ser Leu Tyr Thr Gly Ser Leu Trp Tyr Thr Pro Ile Arg Arg
                245                 250                 255

Glu Trp Tyr Tyr Glu Val Ile Ile Val Arg Val Glu Ile Asn Gly Gln
                260                 265                 270

Asp Leu Lys Met Asp Cys Lys Glu Tyr Asn Tyr Asp Lys Ser Ile Val
            275                 280                 285

Asp Ser Gly Thr Thr Asn Leu Arg Leu Pro Lys Lys Val Phe Glu Ala
            290                 295                 300

Ala Val Lys Ser Ile Lys Ala Ala Ser Ser Thr Glu Lys Phe Pro Asp
305                 310                 315                 320

Gly Phe Trp Leu Gly Glu Gln Leu Val Cys Trp Gln Ala Gly Thr Thr
                325                 330                 335

Pro Trp Asn Ile Phe Pro Val Ile Ser Leu Tyr Leu Met Gly Glu Val
            340                 345                 350

Thr Asn Gln Ser Phe Arg Ile Thr Ile Leu Pro Gln Gln Tyr Leu Arg
            355                 360                 365

Pro Val Glu Asp Val Ala Thr Ser Gln Asp Asp Cys Tyr Lys Phe Ala
        370                 375                 380

Val Ser Gln Ser Ser Thr Gly Thr Val Met Gly Ala Val Ile Met Glu
385                 390                 395                 400

Gly Phe Tyr Val Val Phe Asp Arg Ala Arg Lys Arg Ile Gly Phe Ala
                405                 410                 415

Val Ser Ala Cys His Val His Asp Glu Phe Arg Thr Ala Ala Val Glu
            420                 425                 430

Gly Pro Phe Val Thr Ala Asp Met Glu Asp Cys Gly Tyr Asn Ile Pro
            435                 440                 445

Gln Thr Asp Glu Ser Thr Leu Met Thr Ile Ala Tyr Val Met Ala Ala
        450                 455                 460
```

-continued

```
Ile Cys Ala Leu Phe Met Leu Pro Leu Cys Leu Met Val Cys Gln Trp
465                 470                 475                 480

Arg Cys Leu Arg Cys Leu Arg His Gln His Asp Asp Phe Ala Asp Asp
                485                 490                 495

Ile Ser Leu Leu Lys
                500
```